US012662530B2

(12) United States Patent
Sparwasser et al.

(10) Patent No.: US 12,662,530 B2
(45) Date of Patent: Jun. 23, 2026

(54) ANTI-ADM-ANTIBODIES BINDING TO THE FREE N-TERMINUS FOR ACCELERATED TRANSITION OF ADM-GLY TO BIO-ADM IN PATIENTS WITH ADM-GLY/ BIO-ADM RATIO ABOVE A THRESHOLD AND COMBINATION WITH VITAMIN C

(71) Applicant: SphingoTec GmbH, Hennigsdorf (DE)

(72) Inventors: Andrea Sparwasser, Hennigsdorf (DE); Paul Kaufmann, Berlin (DE); Joachim Struck, Berlin (DE)

(73) Assignee: SPHINGOTEC GMBH, Hennigsdorf (DE)

( * ) Notice: Subject to any disclaimer, the term of this patent is extended or adjusted under 35 U.S.C. 154(b) by 852 days.

(21) Appl. No.: 17/802,164

(22) PCT Filed: Feb. 25, 2021

(86) PCT No.: PCT/EP2021/054763
§ 371 (c)(1),
(2) Date: Aug. 25, 2022

(87) PCT Pub. No.: WO2021/170763
PCT Pub. Date: Sep. 2, 2021

(65) Prior Publication Data
US 2023/0357383 A1 Nov. 9, 2023

(30) Foreign Application Priority Data

Feb. 26, 2020 (EP) ..................................... 20159650

(51) Int. Cl.
| C07K 16/26 | (2006.01) |
| A61K 39/00 | (2006.01) |
| A61P 43/00 | (2006.01) |

(52) U.S. Cl.
CPC ...... *C07K 16/26* (2013.01); *A61K 39/001144* (2018.08); *A61P 43/00* (2018.01)

(58) Field of Classification Search
None
See application file for complete search history.

(56) References Cited

U.S. PATENT DOCUMENTS

| 5,580,717 | A | 12/1996 | Dower et al. |
| 5,585,089 | A | 12/1996 | Queen et al. |
| 5,656,500 | A | 8/1997 | Law et al. |
| 5,807,715 | A | 9/1998 | Morrison et al. |
| 5,910,416 | A | 6/1999 | Kitamura et al. |
| 5,969,108 | A | 10/1999 | Mccafferty et al. |
| 6,255,067 | B1 | 7/2001 | Keutmann et al. |
| 7,064,107 | B2 | 6/2006 | Ladner et al. |
| 7,968,681 | B2 | 6/2011 | Stemmer et al. |
| 8,278,262 | B2 | 10/2012 | Kolmar et al. |
| 8,748,351 | B2 | 6/2014 | Kunert et al. |
| 9,376,477 | B2 | 6/2016 | Grabulovski et al. |

| 10,232,014 | B2 | 3/2019 | Hohlbaum et al. |
| 10,556,933 | B2 | 2/2020 | Abrahmsen et al. |
| 2004/0023334 | A1 | 2/2004 | Prior |
| 2010/0028995 | A1 | 2/2010 | Graversen et al. |
| 2013/0117871 | A1 | 5/2013 | Kucherlapati et al. |
| 2015/0344539 | A1 | 12/2015 | Binz et al. |
| 2017/0334958 | A1 | 11/2017 | Lipovsek et al. |
| 2021/0302440 | A1 | 9/2021 | Melander |
| 2021/0311078 | A1 | 10/2021 | Bergmann |
| 2022/0227854 | A1 | 7/2022 | Bergmann |

FOREIGN PATENT DOCUMENTS

| DE | 2594587 | * | 5/2014 | ............. C07K 16/26 |
| JP | H03501205 | A | 3/1991 | |
| WO | 2009055669 | A2 | 4/2009 | |
| WO | 2013072510 | A1 | 5/2013 | |
| WO | 2013072511 | A1 | 5/2013 | |
| WO | 2013072513 | A1 | 5/2013 | |
| WO | 2013072514 | A1 | 5/2013 | |
| WO | WO 2018/109228 | * | 6/2018 | ............. C07K 16/22 |
| WO | 2019057992 | A2 | 3/2019 | |
| WO | 2019077082 | A1 | 4/2019 | |

(Continued)

OTHER PUBLICATIONS

Kayambankadzanja et al., BMJ Open 2022;12:e060972. doi:10.1136/ bmjopen-2022-060972 (Year: 2022).*
Piche-Nicholas et al., MAbs. 2018; 10: 81-94. doi: 10.1080/19420862.2017.1389355 (Year: 2018).*
Christopher Geven et al: "Vascular Effects of Adrenomedullin and the Anti-Adrenomedullin Antibody Adrecizumab in Sepsis :", Shock, vol. 50, No. 2, Aug. 1, 2018 (Aug. 1, 2018), US, pp. 132-140, XP055700172, ISSN: 1073-2322, DOI: 10.1097/SHK.0000000000001103.
Alpha A Fowler III et al: "Phase I safety trial of intravenous ascorbic acid in patients with severe sepsis", Journal of Translational Medicine, Biomed Central, vol. 12, No. 1, Jan. 31, 2014 (Jan. 31, 2014), p. 32, XP021178652, ISSN: 1479-5876, DOI: 10.1186/1479-5876-12-32.

(Continued)

*Primary Examiner* — Christina M Borgeest
(74) *Attorney, Agent, or Firm* — Millen, White, Zelano & Branigan P.C.; Ryan R. Pool

(57) ABSTRACT

Anti-adrenomedullin (ADM) antibody or an anti-ADM antibody fragment or anti-ADM non-Ig scaffold for the treatment of a critically ill patients suffering from an acute disease or condition resulting in the accelerated the conversion of ADM-Gly to ADM-NH$_2$ of circulating ADM-Gly in the patient. The patient has a ratio of pro-Adrenomedullin or a fragment thereof to ADM-NH$_2$ above a predetermined threshold in a sample of bodily fluid. The pro-Adrenomedullin or fragment thereof is PAMP, MR-proADM, ADM-Gly or CT-proADM and the anti-ADM antibody or anti-ADM fragment or anti-ADM non-Ig scaffold binds to the N-terminal and/or mid-regional part (amino acid 1-42) of ADM-Gly and/or ADM-NH$_2$: YRQSMNNFQGLRSFGCRFGTCTVQKLAHQIYQFTD KDKDNVA.

31 Claims, 18 Drawing Sheets

Figure 1B:
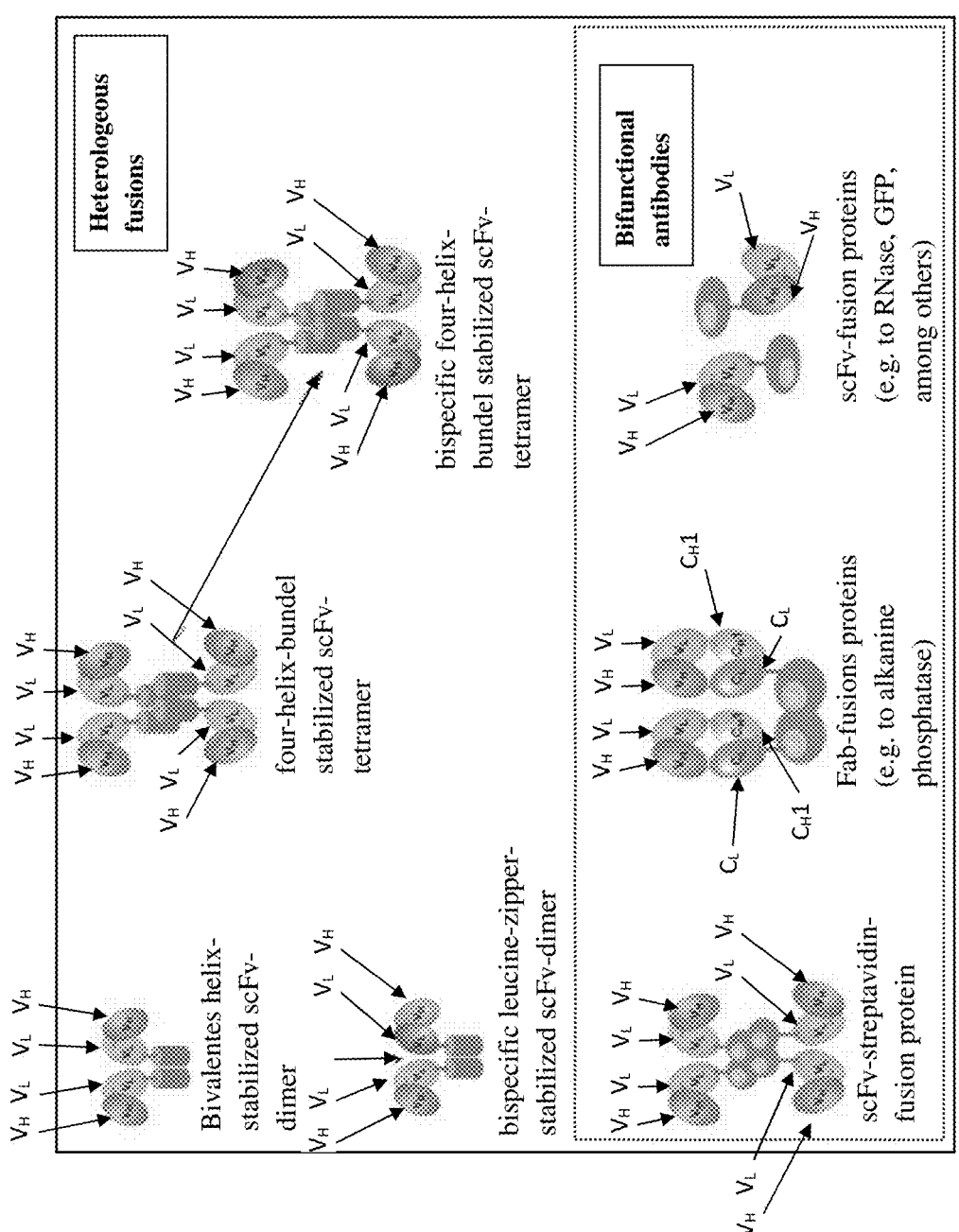

Specification includes a Sequence Listing.

(56)                    References Cited

FOREIGN PATENT DOCUMENTS

WO          2019154900 A1      8/2019
WO          2021038078 A1      3/2021

OTHER PUBLICATIONS

Alexandre Mebazaa et al: "Circulating adrenomedullin estimates survival and reversibility of organ failure in sepsis: the prospective observational multinational Adrenomedullin and Outcome in Sepsis and Septic Shock-1 (AdrenOSS-1) study", Critical Care, vol. 22, No. 1, Dec. 1, 2018 (Dec. 1, 2018), XP055718927, DOI: 10.1186/s13054-018-2243-2.

International Search Report PCT/EP2021/054763 dated Jun. 7, 2021 (pp. 1-7) and Written Opinion (pags 1-6).

European Search Report EP20159650 dated Jul. 31, 2020 (pp. 1-21).

Finkelstein A.V. et al: "Fizika belka", Protein Physics: Lecture course with color and stereoscopic illustrations and tasks: textbook, 4th ed., corrected and updated, Moscow: KDU, 524 pages, 2012, pp. 22-23.

Tobi Dror et al: "Structural changes involved in protein binding correlate with intrinsic motions of proteins in the unbound state", PNAS, Dec. 27, 2005, vol. 102, No. 52, pp. 18908-18913.

Abelev G.I. et al: "Monoclonal Antibodies", Sorosovsky Education Journal No. 1, 1998, pp. 16-20.

Filipovic et al: "Biochemical Foundations of Human Life", Moscow, Vlados, 2005, pp. 68-70.

Altshuler E.P. et al: "Production of recombinant antibodies and methods for increasing their affinity", Advances in Biological Chemistry, vol. 50, 2010, pp. 207-208.

Roitt A. et al: "Immunology", Moscow, Mir, 2000, p. 150; 158.

Asakawa Hiroshi et al: "Elevation of two molecular forms of adrenomedullin in plasma and urine in patients with acute myocardial infarction treated with early coronary angioplasty", Clinical Science, London, 2001, vol. 100, No. 1, pp. 117-126.

Bousquet-Moore Danielle et al: "Peptidylglycine a-amidating monooxygenase and copper: a gene-nutrient interaction critical to nervous system function", Journal of Neuroscience Research, Jul. 15, 2010, vol. 88, Issue 12, pp. 2535-2545.

Carr Anitra C. et al: "Ascorbate-dependent vasopressor synthesis: a rationale for vitamin C administration in severe sepsis and septic shock?", Critical Care, Dec. 1, 2015, vol. 19, No. 418, pp. 1-8.

Mitsuda Yuuichi et al: "Large-scale production of functional human adrenomedullin: expression, cleavage, amidation, and purification", Protein Expression and Purification, Aug. 2002, vol. 25, Issue 3, pp. 448-455.

Ohta Hideki et al: "A simple immunoradiometric assay for measuring the entire molecules of adrenomedullin in human plasma", Clinica Chimica Acta, Sep. 1999, vol. 287, Iss. 1-2, pp. 131-143.

* cited by examiner

Fig. 1a:

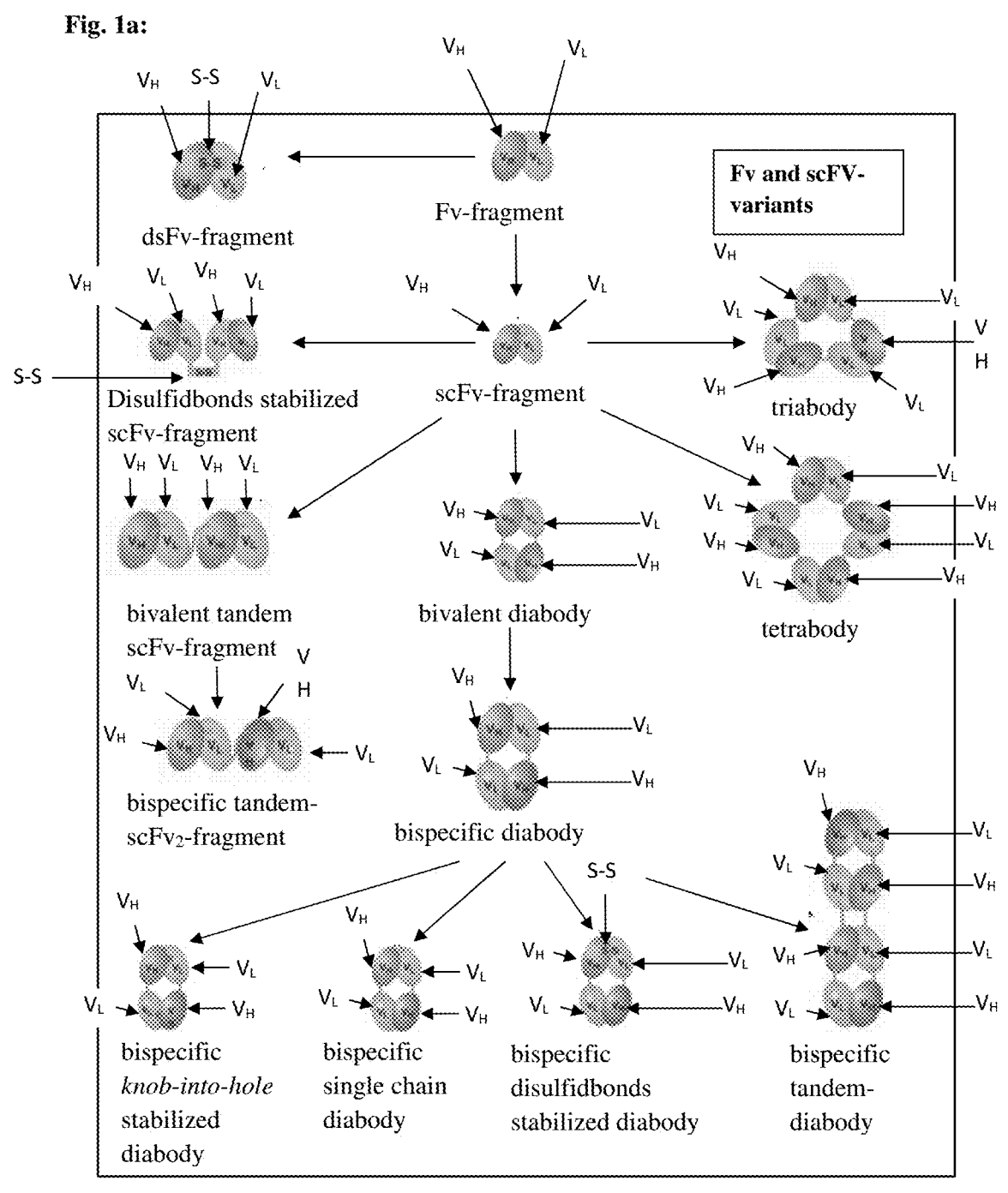

Fv and scFV-variants dsFv-fragment

Fv-fragment

Disulfidbonds stabilized scFv-fragment scFv-fragment triabody bivalent tandem scFv-fragment bivalent diabody tetrabody bispecific tandem-scFv₂-fragment bispecific diabody bispecific knob-into-hole stabilized diabody bispecific single chain diabody bispecific disulfidbonds stabilized diabody bispecific tandem-diabody Standard curve hADM Stability hADM

+ NT-H

- NT-H

Concentration [%]

Time [h]

Fig 5:

**IGHV1-69*11 (SEQ ID No.:36):**

QVQLVQSGAEVKKPGSSVKVSCKASGGTFSSYAISWVRQAPGQGLEWMGRIIPILGT
ANYAQKFQGRVTITADESTSTAYMELSSLRSEDTAVYYCARYYYYYGMDVWGQGT
TVTVSS

HB3:

QVQLQQSGAELMKPGASVKISCKATGYTFSRYWIEWVKQRPGHGLEWIGEILPGSGS
TNYNEKFKGKATITADTSSNTAYMQLSSLTSEDSAVYYCTEGYEYDGFDYWGQGTT
LTVSS

Alignment (ClustalW2): Identical amino acids are illustrated by stars; points indicate conservative changes.

```
IGHV1:

QVQLVQSGAEVKKPGSSVKVSCKASGGTFSSYAISWVRQAPGQGLEWMGRIIPILGTANYAQKFQGR
        VTITADESTSTAYMELSSLRSEDTAVYYCARYYYYYGMDVWGQGTTVTVSS
HB3:

QVQLQQSGAELMKPGASVKISCKATGYTFSRYWIEWVKQRPGHGLEWIGEILPGSGSTNYNEKFKGK
        ATITADTSSNTAYMQLSSLTSEDSAVYYCTEGYEYDGFDYWGQGTTLTVSS
        **** *****: ***:***:****:* *** * *.**:* **:****:*.*:*  *::** :**:*:
        .***** *:.****:**** ***:*****:. * * *:* ******:****
``` baseline bio-ADM [pg/mL]:

|  | placebo | 0.5 mg/kg | 2 mg/kg | 8 mg/kg |
|---|---|---|---|---|
| Median | 7.050 | 6.750 | 5.450 | 7.100 |

ANTI-ADM-ANTIBODIES BINDING TO THE FREE N-TERMINUS FOR ACCELERATED TRANSITION OF ADM-GLY TO BIO-ADM IN PATIENTS WITH ADM-GLY/ BIO-ADM RATIO ABOVE A THRESHOLD AND COMBINATION WITH VITAMIN C

FIELD OF THE INVENTION

Subject matter of the present invention is an anti-adrenomedullin (ADM) antibody or an anti-adrenomedullin antibody fragment or an anti-ADM non-Ig scaffold for use in a patient to accelerate the conversion of ADM-Gly to ADM-NH$_2$ in said patient, wherein said patient is characterized by having a ratio of pro-Adrenomedullin or a fragment thereof to ADM-NH$_2$ (SEQ ID No. 20) above a certain threshold in a sample of bodily fluid, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34) and wherein said anti-ADM antibody or anti-ADM fragment or anti-ADM non-Ig scaffold binds to the N-terminal and/or mid-regional part (amino acid 1-42) of ADM-Gly and/15 or ADM-NH$_2$: YRQSMNNFQGLRSFGCRFGTCTVQKLAHQIYQFTD KDKDNVA (SEQ ID No. 23).

BACKGROUND

The peptide adrenomedullin (ADM) was described for the first time in 1993 (Kitamura et al., 1993. *Biochem Biophys Res Comm* 192 (2): 553-560) as a novel hypotensive peptide comprising 52 amino acids, which had been isolated from a human pheochromocytoma cell line (SEQ ID No. 20). In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "pre-proadrenomedullin" (pre-proADM). In the present description, all amino acid positions specified usually relate to the pre-proADM, which comprises the 185 amino acids. Pre-proADM is subsequently converted into the 164 amino acid pro-ADM (SEQ ID No. 31) by cleavage of the N-terminal signal-peptide. Pro-ADM is further processed into pro-ADM N-terminal 20 peptide (PAMP; SEQ ID No. 32), midregional pro-ADM (MR-proADM; SEQ ID No. 33), adrenotensin pro-ADM 153-185 (CT-pro ADM; SEQ ID No. 34) and immature ADM, a C-terminally glycine-extended version of ADM (ADM-Gly; SEQ ID No. 21). This is converted into the mature bioactive form of ADM (bio-ADM; ADM-NH$_2$; SEQ ID No. 20) by enzymatic amidation of its C-terminus. More than half of the known neural and endocrine peptides require the formation of a C-terminal alpha-amide group to gain full biological activity (Guembe et al. 1999. *J Histochem Cytochem* 47(5): 623-36; Vishwanatha et al. 2013. *Handbook of Biologically Active Peptides Peptidylglycine Amidating Monoxygenase (PAM)*. Second Edi. Elsevier Inc.). This final step of peptide hormone biosynthesis involves the action of a bifunctional enzyme, the peptidylglycine alpha-amidating monooxygenase (PAM), that specifically recognizes C-terminal glycine (CT-Gly) residues in its substrates. PAM cleaves glyoxylate from the peptides CT-Gly residue in a two-step enzymatic reaction leading to the formation of c-terminally alpha-amidated peptide hormones, wherein the resulting alpha-amide group originates from the cleaved CT-Gly (Prigge et al. 2000.

*Cellular and Molecular Life Sciences* 57(8): 1236-59). This amidation reaction takes place in the lumen of secretory granules prior to exocytosis of the amidated product (Martinez et al. 1996. *Am J Pathol* 149(2): 707-16).

In humans, the PAM gene is located at chromosome 5q21.1 having a length of 160 kb containing 25 known exons (Gaier et al. 2014. *BMC Endocrine Disorders* 14). At least 6 isoforms are known to be generated by alternative splicing (SEQ ID No. 39-44). The PAM enzyme was found to be expressed at different levels in almost all mammalian cell types, with significant expression in airway epithelium, endothelial cells, ependymal cells in the brain, adult atrium, brain, kidney, pituitary, gastrointestinal tract and reproductive tissues (Chen et al. 2018. *Diabetes Obes Metab* 20 Suppl 2: 64-76; Oldham et al. 1992. *Biochem Biophys Res Commun* 184(1): 323-29; Schafer et al. 1992. *J Neurosci* 12(1): 222-34).

The largest known PAM isoform 1 (SEQ ID No. 39) is the precursor protein (1-973 amino acids). The N-terminal signal sequence (amino acids 1-20) assures direction of the nascent PAM polypeptide into the secretory lumen of endoplasmic reticulum and is subsequently cleaved co-translationally. Afterwards the PAM-pro-peptide is processed by the same machinery used for the biosynthesis of integral membrane proteins and secreted proteins including cleavage of the pro-region (amino acids 21-30), assuring proper folding, disulfide bond formation, phosphorylation and glycosylation (Bousquet-Moore et al. 2010. *J Neurosci Res* 88(12):2535-45). The PAM cDNA encodes two distinct enzymatic activities: the first enzymatic activity is named peptidyl-glycine alpha-hydroxylating monooxygenase (PHM; EC 1.14.17.3), is an enzyme, capable of catalyzing the conversion of a C-terminal glycine residue to an alpha-hydroxy-glycine; the second activity is named peptidyl-a-hydroxy-glycine alpha-amidating lyase (PAL; EC 4.3.2.5) and is an enzyme capable of catalyzing the conversion of an alpha-hydroxy-glycine to an alpha-amide with subsequent glyoxylate release. The sequential action of these separate enzymatic activities results in the overall peptidyl-glycine alpha amidating activity. The first enzymatic activity (PHM) is located directly upstream of the pro-region (within amino acids 31-494 of isoform 1 (SEQ ID No. 45)). The second catalytic activity (PAL) is located after exon 16 in isoform 1 within amino acids 495-817 (SEQ ID No. 46). Both activities may be encoded together within one polypeptide as a membrane-bound protein (isoforms 1, 2, 5, 6; corresponding to SEQ ID No. 39, 40, 43 and 44) as well within one polypeptide as a soluble protein lacking the transmembrane domain (TMD; isoforms 3 and 4; corresponding to SEQ ID No. 41 and 42). While isoforms 1, 2, 5 and 6 remain in the outer plasma membrane after fusion of secretory vesicles with the plasma membrane with subsequent endocytosis and recycling or degradation, soluble PAM isoforms lacking the TMD (isoforms 3 and 4) (amino acids 864-887) are co-secreted with the peptide hormones (Wand et al. 1985 *Metabolism* 34(11): 1044-52). Furthermore, prohormone convertases may convert membrane bound PAM protein into soluble PAM protein by cleavage within the flexible region (exons 25/26) connecting PAL with the TMD during the secretory pathway (Bousquet-Moore et al. 2010. *J Neurosci Res* 88(12): 2535-45). The PHM subunit may be cleaved from soluble or membrane bound PAM within the secretory pathway by prohormone convertases that address a double-basic cleavage-site in the exon 16 region. Furthermore, during endocytosis the full-length PAM protein may be also converted into a soluble form due to the action of alpha- and gamma secretases (Bousquet-Moore et al. 2010. *J Neurosci*

3

*Res* 88(12): 2535-45). Membrane bound PAM from late endosome can be further secreted in form of exosomal vesicles.

PHM and PAL activities, as well as the activity of the full-length PAM were determined in several human tissues and body fluids. However, the separated PHM and PAL activities in soluble forms will also lead to formation of c-terminally alpha amidated products from c-terminally glycinated substrates when allowed to perform their separate reactions in the same compartment, body fluid or in an in vitro experimental setup. How the transfer of the PHM hydroxylated product to the PAL takes place is not exactly understood to date. There is evidence that the hydroxylated product is released into solution and is not directly transferred from PHM to PAL (Yin et al. 2011. *PLoS One* 6(12): e28679). Also not clear to date is the source of PAM in circulation.

PHM is a copper dependent monooxygenase responsible for stereo-specific hydroxylation of the c-terminal glycine at the alpha-carbon atom. During the hydroxylation reaction ascorbate is believed to be the naturally occurring reducing agent, while the oxygen in the newly formed hydroxyl group was shown to originate from molecular oxygen. The catalytic action of PAL involves proton abstraction form the PHM-formed hydroxy-glycine by a protein-backbone derived base and a nucleophilic attack of hydroxyl-group oxygen to the divalent metal leading to a cleavage of glyoxylate and formation of a c-terminal amide.

Thus the term "amidating activity", "alpha-amidating activity", "peptidyl-glycine alpha-amidating activity" or "PAM activity" refers to the sequential enzymatic activities of PHM and PAL, independent of the present splice variant or mixtures of splice variants or post-translationally modified PAM enzymes or soluble, separated PHM or PAL activities or soluble PHM and membrane bound PAL or combinations of all mentioned forms leading to the formation of alpha-amidated products of peptide or non-peptide character from glycinated substrates of peptide or non-peptide character. In other words, the term "amidating activity", "alpha-amidating activity", "peptidyl-glycine alpha-amidating activity" or "PAM activity" may be described as the sequential action of enzymatic activities located within amino acids 31 to 817 in the propeptide encoded by the human PAM cDNA, independent of present splice-variants or mixtures thereof.

The discovery and characterization of ADM in 1993 triggered intensive research activity, the results of which have been summarized in various review articles, in the context of the present description, reference being made in particular to the articles to be found in an issue of "Peptides" devoted to ADM in particular (Takahashi 2001. *Peptides* 22: 1691; Eto 2001. *Peptides* 22: 1693-1711). A further review is Hinson et al. 2000 (Hinson et al. 2000. *Endocrine Reviews* 21(2): 138-167). In the scientific investigations to date, it has been found, inter alia, that ADM may be regarded as a polyfunctional regulatory peptide. As mentioned above, it is released into the circulation in an inactive form extended by glycine (Kitamura et al. 1998. *Biochem Biophys Res Commun* 244(2): 551-555). There is also a binding protein (Pio et al. 2001. *The Journal of Biological Chemistry* 276(15): 12292-12300), which is specific for ADM and probably likewise modulates the effect of ADM. Those physiological effects of ADM as well as of PAMP, which are of primary importance in the investigations to date, were the effects influencing blood pressure.

Hence, ADM is an effective vasodilator, and thus it is possible to associate the hypotensive effect with the particular peptide segments in the C-terminal part of ADM. It has furthermore been found that the above-mentioned physiologically active peptide PAMP formed from pre-proADM likewise exhibits a hypotensive effect, even if it appears to have an action mechanism differing from that of ADM (in addition to the mentioned review articles above, Eto et al. 2001 and Hinson et al. 2000 see also Kuwasaki et al. 1997. *FEBS Lett* 414(1): 105-110 Kuwasaki et al. 1999. *Ann. Clin. Biochem.* 36: 622-628; Tsuruda et al. 2001 *Life Sci.* 69(2): 239-245 and EP-A2 0 622 458). It has furthermore been found, that the concentrations of ADM, which can be measured in the circulation and other biological liquids, are in a number of pathological states, significantly above the concentrations found in healthy control subjects. Thus, the ADM level in patients with congestive heart failure, myocardial infarction, kidney diseases, hypertensive disorders, diabetes mellitus, in the acute phase of shock and in sepsis and septic shock are significantly increased, although to different extents. The PAMP concentrations are also increased in some of said pathological states, but the plasma levels are lower relative to ADM (Eto 2001. *Peptides* 22: 1693-1711). It was reported that high concentrations of ADM are observed in sepsis, and the highest concentrations in septic shock (Eto 2001. Peptides 22: 1693-1711; Hirata et al. *Journal of Clinical Endocrinology and Metabolism* 81(4): 1449-1453; Ehlenz et al. 1997. *Exp Clin Endocrinol Diabetes* 105: 156-162; Tomoda et al. 2001. *Peptides* 22: 1783-1794; Ueda et al. 1999. *Am. J. Respir. Crit. Care Med.* 160: 132-136 and Wang et al. 2001. *Peptides* 22: 1835-1840). Moreover, plasma concentrations of ADM are elevated in patients with heart failure and correlate with disease severity (Hirayama et al. 1999. *J Endocrinol* 160: 297-303; Yu et al. 2001. *Heart* 86: 155-160). High plasma ADM is an independent negative prognostic indicator in these subjects (Poyner et al. 2002. *Pharmacol Rev* 54: 233-246).

Kitamura and colleagues showed that the concentration of mature ADM and ADM-Gly was significantly elevated in plasma of hypertensive patients compared to healthy volunteers (Kitamura et al. 1998. *Biochem Biophys Res Comm* 244(2): 551-5). In both groups mature ADM was much lower than ADM-Gly. However, the ratio of mature ADM to ADM-Gly was not significantly different between hypertensive and non-hypertensive subjects.

It is reported for the early phase of sepsis, that ADM improves heart function and the blood supply in liver, spleen, kidney and small intestine. Anti-ADM-neutralizing antibodies neutralize the before mentioned effects during the early phase of sepsis (Wang et al. 2001. *Peptides* 22: 1835-1840). For other diseases, blocking of ADM may be beneficial to a certain extent. However, it might also be detrimental if ADM is totally neutralized, as a certain amount of ADM may be required for several physiological functions. In many reports it was emphasized, that the administration of ADM may be beneficial in certain diseases. In contrast thereto, in other reports ADM was reported as being life-threatening when administered in certain conditions.

WO2013/072510 describes a non-neutralizing N-terminal anti-ADM antibody for use in therapy of a severe chronical or acute disease or acute condition of a patient for the reduction of the mortality risk for said patient.

WO2013/072511 describes a non-neutralizing N-terminal anti-ADM antibody for use in therapy of a chronical or acute disease or acute condition of a patient for prevention or reduction of organ dysfunction or organ failure.

WO2013/072513 describes a N-terminal anti-ADM antibody for use in therapy of an acute disease or condition of a patient for stabilizing the circulation.

WO2013/072514 describes a N-terminal anti-ADM antibody for regulating the fluid balance in a patient having a chronic or acute disease or acute condition.

WO2019/154900 describes a non-neutralizing N-terminal anti-ADM antibody for use in therapy and prevention of dementia. Moreover, WO2019/154900 describes a method for diagnosing and monitoring a (preventive) therapy of dementia by determining a ratio of the level of mature ADM to the level of pro-Adrenomedullin or a fragment thereof.

WO2013/072512 describes a non-neutralizing N-terminal anti-ADM antibody that is an ADM stabilizing antibody enhancing the half-life ($t_{1/2}$ half retention time) of adrenomedullin in serum, blood, plasma.

The efficacy of non-neutralizing antibody targeted against the N-terminus of ADM was investigated in a survival study in CLP-induced sepsis in mice. Pre-treatment with the non-neutralizing antibody resulted in decreased catecholamine infusion rates, kidney dysfunction, and ultimately improved survival (Struck et al. 2013. *Intensive Care Med Exp* 1(1):22; Wagner et al. 2013. *Intensive Care Med Exp* 1(1):21). In addition, antibodies against the mid-regional part of ADM (MR-ADM antibodies) also significantly improved the survival in mice with CLP-induced sepsis, but to a lower extent when compared to N-terminal anti-ADM antibodies (Struck et al. 2013. *Intensive Care Med Exp* 1(1):22).

Due to these positive results, a humanized version of an N-terminal anti-ADM antibody, named Adrecizumab, has been developed for further clinical development. Beneficial effects of Adrecizumab on vascular barrier function and survival were recently demonstrated in preclinical models of systemic inflammation and sepsis (Geven et al. 2018. *Shock* 50(6): 648-654). In this study, pre-treatment with Adrecizumab attenuated renal vascular leakage in endotoxemic rats as well as in mice with CLP-induced sepsis, which coincided with increased renal expression of the protective peptide Ang-1 and reduced expression of the detrimental peptide vascular endothelial growth factor. Also, pre-treatment with Adrecizumab improved 7-day survival in CLP-induced sepsis in mice from 10 to 50% for single and from 0 to 40% for repeated dose administration. Moreover, in a phase I study, excellent safety and tolerability was demonstrated: no serious adverse events were observed, no signal of adverse events occurring more frequently in Adrecizumab-treated subjects was detected and no relevant changes in other safety parameters were found (Geven et al. 2017. *Intensive Care Med Exp* 5 (Suppl 2): 0427). Of particular interest is the proposed mechanism of action of Adrecizumab. Both, animal and human data reveal a potent, dose-dependent increase of circulating ADM following administration of this antibody. Based on pharmacokinetic data and the lack of an increase in MR-proADM (an inactive peptide fragment derived from the same prohormone as ADM), the higher circulating ADM levels cannot be explained by an increased production.

A mechanistic explanation for this increase could be that the excess of antibody in the circulation may drain ADM from the interstitium to the circulation, since ADM is small enough to cross the endothelial barrier, whereas the antibody is not (Geven et al. 2018. *Shock.* 50(2): 132-140). In addition, binding of the antibody to ADM leads to a prolongation of ADM's half-life. Even though NT-ADM antibodies partially inhibit ADM-mediated signalling, a large increase of circulating ADM results in an overall "net"

increase of ADM activity in the blood compartment, where it exerts beneficial effects on endothelial cells (ECs; predominantly barrier stabilization), whereas ADM's detrimental effects on vascular smooth muscle cells (VSMCs; vasodilation) in the interstitium are reduced.

Vitamin C (ascorbic acid) is a water-soluble vitamin with a variety of antioxidant, anti-inflammatory, and microvascular effects. Vitamin C levels are known to be decreased in critical illness and are associated with severity of illness. Supplemental vitamin C has shown promise in both animal models of sepsis and human trials in the intensive care unit (ICU) setting: Preclinical research in early sepsis revealed that vitamin C prevented sepsis-induced cytokine surges that activate and sequester neutrophils in lung, thus damaging alveolar capillaries (Fisher eta. 2012. *Physiol Lung Cell Mol Physiol.* 303(1): L20-L32; Fisher et al. 2011. *Crit Care Med.* 39 (6): 1454-1460). Vitamin C increased alveolar fluid clearance by preventing activated neutrophil accumulation in alveolar spaces, limiting alveolar epithelial water-channel damage, and promoting their increased expression (Fisher et al. 2011. *Crit Care Med.* 39 (6): 1454-1460. In addition, vitamin C prevented neutrophil extracellular trap formation, a biological event in activated neutrophils that promotes vascular injury (Mohammed et al. 2013 *Nutrients* 5(8): 3131-3151).

In a recent, phase I trial in 24 medical intensive care unit (ICU) patients with severe sepsis, high dose administration of vitamin C reduced the extent of multiple organ failure and attenuated circulating injury biomarker levels (Fowler et al. 2014. *J Transl Med* 12: 32). In a double-blinded randomized clinical trial, 28 adult surgical patients with septic shock had a significantly decreased vasopressor requirement, a faster weaning of vasopressors and a significantly lower 28-day mortality in the ascorbic acid, compared to the placebo group (Zhabet et al. 2016. *Res Pharm Pract* 5: 94-100). Moreover, intravenous vitamin C therapy reduced mortality in septic patients from 46% in the placebo group to almost 30% in the vitamin C group at day 28 (Fowler et al. 2019. *JAMA* 322(13): 1261-1270).

Surprisingly, the present invention shows that the ratio of ADM-Gly and bioactive ADM is highly variable although current literature describes that only 5-20% of ADM is ADM-Gly (Kitamura et al. 1998. *Biochemical and Biophysical Research Communications.* 244(2): 551-555). Moreover, our data show for the first time that the conversion of ADM-Gly to bioactive ADM also occurs within the circulation, notwithstanding that the amidation of peptides, especially ADM, is described so far as an intracellular rather than an intravascular process (Kumar, Mains, Eipper 2016. *Journal of Molecular Endocrinology.* 56(4): T63-T76). The present invention also clearly demonstrates that N-terminal and mid-regional anti-ADM antibodies, in addition to its effects described above, accelerate the conversion of ADM-Gly to bioactive ADM in critically ill patients with an acute disease or condition. Surprisingly, antibodies binding to the mid-regional part of ADM show a stronger effect than antibodies binding to the N-terminal part of ADM and/or ADM-Gly. In addition, the present invention clearly demonstrates that those N-terminal and mid-regional anti-ADM antibodies in combination with ascorbate significantly increase the enzymatic amidation of glycinated adrenomedullin to mature ADM catalyzed by PAM in plasma.

DESCRIPTION OF THE INVENTION

Subject-matter of the present application is an anti-adrenomedullin (ADM) antibody or an anti-adrenomedullin antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH₂ of circulating ADM-Gly in said patient, wherein said patient is characterized by having a ratio of pro-Adrenomedullin or a fragment thereof to ADM-NH₂ (SEQ ID No. 20) above a certain threshold in a sample of bodily fluid, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34) and wherein said anti-ADM antibody or anti-ADM fragment or anti-ADM non-Ig scaffold binds to the N-terminal and/or mid-regional part (amino acid 1-42) of ADM-Gly and/or ADM-NH₂:
YRQSMNNFQGLRSFGCRFGTCTVQKLAHQIYQFTD KDKDNVA (SEQ ID No. 23).

In one embodiment, an anti-adrenomedullin (ADM) antibody or an anti-adrenomedullin antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH₂ of circulating ADM-Gly in said patient, wherein said patient is characterized by having a ratio of pro-Adrenomedullin or a fragment thereof to ADM-NH₂ (SEQ ID No. 20) above a certain threshold in a sample of bodily fluid, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34) and wherein said anti-ADM antibody or anti-ADM fragment or anti-ADM non-Ig scaffold binds to the N-terminal and/or mid-regional part (amino acid 1-42) of ADM-Gly and/or ADM-NH₂:
YRQSMNNFQGLRSFGCRFGTCTVQKLAHQIYQFTDK DKDNVA (SEQ ID No. 23). and wherein the anti-adrenomedullin (ADM) antibody or an anti-adrenomedullin antibody fragment or anti-ADM non-Ig scaffold is used in combination with L-ascorbic acid.

One embodiment of the present application relates to an anti-adrenomedullin (ADM) antibody or an anti-adrenomedullin antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH₂ of circulating ADM-Gly in said patient, wherein said anti-ADM antibody or anti-ADM fragment or anti-ADM non-Ig scaffold binds to the N-terminal part (amino acid 1-21) of ADM-Gly and/or ADM-NH₂: YRQSMNNFQGLRSFGCRFGTC (SEQ ID No. 14).

One embodiment of the present application relates to an anti-adrenomedullin (ADM) antibody or an anti-adrenomedullin antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH₂ of circulating ADM-Gly in said patient, wherein said anti-ADM antibody or anti-ADM fragment or anti-ADM non-Ig scaffold binds to the N-terminal part (amino acid 1-21) of ADM-Gly and/or ADM-NH₂: YRQSMNNFQGLRSFGCRFGTC (SEQ ID No. 14). and wherein the anti-adrenomedullin (ADM) antibody or an anti-adrenomedullin antibody fragment or anti-ADM non-Ig scaffold is used in combination with L-ascorbic acid.

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH₂ of circulating ADM-Gly in said patient, wherein said anti-ADM antibody or anti-ADM antibody fragment or anti-ADM non-Ig scaffold recognizes and binds to the N-terminal end (amino acid 1) of ADM-Gly and/or ADM-NH₂.

Another preferred embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH₂ of circulating ADM-Gly in said patient, wherein said anti-ADM antibody or anti-ADM fragment or anti-ADM non-Ig scaffold binds to the mid-regional part (amino acid 21-42) of ADM-Gly and/or ADM-NH₂: CTVQKLAHQIYQFTDKDKDNVA (SEQ ID No. 48).

Another preferred embodiment of the present application relates to an anti-adrenomedullin (ADM) antibody or an anti-ADM antibody fragment or anti-ADM non-Ig scaffold for use in the treatment of a critically ill patient suffering from dementia in order to accelerate the conversion of ADM-Gly to ADM-NH₂ of circulating ADM-Gly in said patient, wherein said anti-ADM antibody or anti-ADM fragment or anti-ADM non-Ig scaffold binds to the mid-regional part (amino acid 21-42) of ADM-Gly and/or ADM-NH₂: CTVQKLAHQIYQFTDKDKDNVA (SEQ ID No. 48).

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH$_2$ of circulating ADM-Gly in said patient, wherein said anti-ADM antibody or anti-ADM fragment or anti-ADM non-Ig scaffold binds to the mid-regional part (amino acid 21-32) of ADM-Gly and/or ADM-NH$_2$: CTVQKLAHQIYQ (SEQ ID No.: 15).

Another embodiment of the present application relates to an anti-adrenomedullin (ADM) antibody or an anti-ADM antibody fragment or anti-ADM non-Ig scaffold for use in the treatment of a critically ill patient suffering from demen-tia in order to accelerate the conversion of ADM-Gly to ADM-NH$_2$ of circulating ADM-Gly in said patient, wherein said anti-ADM antibody or anti-ADM fragment or anti-ADM non-Ig scaffold binds to the mid-regional part (amino acid 21-32) of ADM-Gly and/or ADM-NH$_2$: CTVQKLAHQIYQ (SEQ ID No.: 15).

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH$_2$ of circulating ADM-Gly in said patient, wherein said anti-ADM antibody or anti-ADM fragment or anti-ADM non-Ig scaffold binds to the mid-regional part (amino acid 27-39) of ADM-Gly and/or ADM-NH$_2$: AHQIYQFTDKDKD (SEQ ID No.: 49).

Another embodiment of the present application relates to an anti-adrenomedullin (ADM) antibody or an anti-ADM antibody fragment or anti-ADM non-Ig scaffold for use in the treatment of a critically ill patient suffering from demen-tia in order to accelerate the conversion of ADM-Gly to ADM-NH$_2$ of circulating ADM-Gly in said patient, wherein said anti-ADM antibody or anti-ADM fragment or anti-ADM non-Ig scaffold binds to the mid-regional part (amino acid 27-39) of ADM-Gly and/or ADM-NH$_2$: AHQIYQFTDKDKD (SEQ ID No.: 49).

One embodiment of the present application relates to an anti-adrenomedullin (ADM) antibody or an anti-ADM anti-body fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein in a sample of bodily fluid of said patient the level of pro-Adrenomedullin or a fragment thereof consisting of the group of PAMP (SEQ ID No. 32), MR-proADM (SEQ ID No. 33), ADM-Gly (SEQ ID No. 21) and CT-proADM (SEQ ID No. 34) and ADM-NH$_2$ (SEQ ID No. 20) is determined.

One preferred embodiment of the present application relates to an Anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein in a sample of bodily fluid of said patient a ratio of the level of ADM-Gly (SEQ ID No. 21) and ADM-NH$_2$ (SEQ ID No. 20) is determined and the patient is treated with said anti-ADM antibody or an anti-ADM antibody fragment or anti-ADM non-Ig scaffold if the ratio is above a certain threshold, wherein the ADM-Gly/ADM-NH$_2$ ratio is in a range between 1 and 10, preferably between 1.5 and 7.5, preferably between 2 and 5, most preferred the threshold is 2.5.

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the sample of bodily fluid of said patient is selected from the group of blood, serum, plasma, urine, cerebrospinal fluid (CSF), and saliva.

A further embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein said sample is selected from the group comprising human citrate plasma, heparin plasma and EDTA plasma.

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the ratio of pro-Adrenomedullin or a fragment thereof and ADM-NH$_2$ of the patient is determined. In a most preferred embodiment, the ratio is measured using an immunoassay.

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein an immunoassay is used for determining the ratio of pro-Adrenomedullin or a fragment thereof and ADM-NH$_2$, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34).

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein said immunoassay is a sandwich immunoassay, preferably a fully automated assay.

One embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the assay sensitivity of said assay for the detection of ADM-NH$_2$ is able to quantify ADM-NH$_2$ of healthy subjects and is <70 pg/ml, preferably <40 pg/ml and more preferably <10 pg/ml.

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the assay sensitivity of said assay for ADM-Gly is able to quantify ADM-Gly of healthy subjects and is 20 pg/ml, preferably 15 pg/ml and more preferably 10 pg/ml.

One embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the assay sensitivity of said assay for the detection of MR-proADM is able to quantify MR-proADM of healthy subjects and is <0.5 nmol/L, preferably <0.4 nmol/L and more preferably <0.2 nmol/L.

Another embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the assay sensitivity of said assay for PAMP is able to quantify PAMP of healthy subjects and is <0.5 pmol/L, preferably <0.25 pmol/L and more preferably <0.1 pmol/L.

One embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the assay sensitivity of said assay for the detection of CT-proADM is able to quantify CT-proADM of healthy subjects and is <100 pmol/L, preferably <75 pmol/L and more preferably <50 pmol/L.

A further embodiment of the present application relates to an anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein the level of pro-Adrenomedullin or a fragment thereof and ADM-NH$_2$ (SEQ ID No. 20) is determined by using one binder to said pro-Adrenomedullin or a fragment thereof and a second binder to ADM-NH$_2$ (SEQ ID No. 20), wherein said proAdrenomedullin or a fragment thereof is selected from the group consisting of PAMP (SEQ ID No. 32), MR-proADM (SEQ ID No. 33), ADM-Gly (SEQ ID No. 21) and CT-proADM (SEQ ID No. 34) and wherein both binders are selected from the group comprising an antibody, an antibody fragment or a non-Ig-Scaffold binding to said pro-Adrenomedullin or a fragment thereof and ADM-NH$_2$.

Another embodiment of the present application relates to an anti-ADM antibody or an anti-ADM antibody fragment or anti-ADM non-Ig scaffold for use in therapy of a patient, wherein said anti-ADM antibody or anti-ADM fragment or anti-ADM non-Ig scaffold binds to the N-terminal and/or mid-regional part (amino acid 1-42) of ADM-Gly and/or ADM-NH$_2$:
YRQSMNNFQGLRSFGCRFGTCTVQKLAHQIYQFTD
KDKDNVA (SEQ ID No. 23), wherein in a sample of bodily fluid of said patient the level of PAM and/or its isoforms and/or fragments thereof is determined and the patient is treated with said anti-ADM antibody or an anti-ADM anti-body fragment or anti-ADM non-Ig scaffold, if the level of PAM is below a threshold.

Another embodiment of the present application relates to an anti-ADM antibody or an anti-ADM antibody fragment or anti-ADM non-Ig scaffold for use in therapy of a patient, wherein said level of PAM and/or its isoforms and/or fragments thereof is the total concentration of PAM and/or its isoforms and/or fragments thereof having at least 12 amino acids or the activity of PAM and/or its isoforms and/or fragments thereof comprising the sequences SEQ ID No. 39, SEQ ID No. 40, SEQ ID No. 41, SEQ ID No. 42, SEQ ID No. 43, SEQ ID No. 44, SEQ ID No. 45, SEQ ID No. 46 and SEQ ID No. 47.

It is to be understood by the skilled artisan, that the PAM isoform sequences (SEQ ID No. 39 to 44) as represented in the sequence list, contain an N-terminal signal sequence (amino acid 1-20), that is cleaved off prior to secretion of the protein. Therefore, in a preferred embodiment the PAM isoform sequences (SEQ ID No. 39 to 44) do not contain the N-terminal signal sequence.

Another embodiment of the present application relates to an anti-ADM antibody or an anti-ADM antibody fragment or anti-ADM non-Ig scaffold for use in therapy of a patient, wherein said anti-ADM antibody or anti-ADM fragment or anti-ADM non-Ig scaffold binds to the N-terminal and/or mid-regional part (amino acid 1-42) of ADM-Gly and/or ADM-NH$_2$:
YRQSMNNFQGLRSFGCRFGTCTVQKLAHQIYQFTD
KDKDNVA (SEQ ID No. 23) and is to be used in combination with L-ascorbic acid.

In a preferred embodiment, the anti-Adrenomedullin (ADM) antibody or anti-ADM antibody fragment or anti-ADM non-Ig scaffold in combination with L-ascorbic acid, a. for use in therapy of an acute disease or acute condition of a patient for stabilizing the systemic circulation of said patient wherein said patient is in need of stabilizing the systemic circulation and exhibits a heart rate of >100 beats/min and/or <65 mm Hg mean arterial pressure and wherein stabilizing the systemic circulation means increasing the mean arterial pressure over 65 mmHg, or b. for use in the prevention of a heart rate increase to >100 beats/min and/or a mean arterial pressure decrease to <65 mm Hg in patients having an acute disease or acute condition, or c. for use in therapy of an acute disease or acute condition of a patient that suffers from a chronic and/or acute disease or acute condition for prevention or reduction of organ dysfunction or prevention of organ failure in said patient and wherein said organ is selected from the group comprising heart, kidney, liver, lungs, pancreas, small intestines and spleen, or d. for use in therapy or prevention of SIRS, meningitis, sepsis, shock, e.g., septic shock in a patient e. for the reduction of the mortality risk in patient with SIRS, meningitis, sepsis, shock, e.g., septic shock.
    wherein said anti-ADM antibody or anti-ADM fragment or anti-ADM non-Ig scaffold binds to the N-terminal and/or mid-regional part (amino acid 1-42) of ADM-Gly and/or ADM-NH$_2$:

(SEQ ID No. 23)
YRQSMNNFQGLRSFGCRFGTCTVQKLAHQIYQFTDKDKDNVA.

Another preferred embodiment of the present application relates to an anti-ADM antibody or anti-ADM antibody fragment or anti-ADM non-Ig scaffold for use in intervention and therapy of a patient and its use in combination with L-ascorbic acid, wherein said L-ascorbic acid is a single enantiomer, a mixture of enantiomers, a mixture of diastereomers or a pharmaceutically acceptable salt, solvate, hydrate or prodrug thereof.

According to the present invention it has been found that the administration of an anti-ADM antibody or anti-ADM antibody fragment or anti-ADM non-Ig scaffold may be used in a patient to accelerate the conversion of ADM-Gly to ADM-NH$_2$, wherein said anti-ADM antibody or anti-ADM fragment or anti-ADM non-Ig scaffold binds to the N-terminal or mid-regional part (amino acid 1-42) of ADM-Gly and/or ADM-NH$_2$:

(SEQ ID No.: 23)
YRQSMNNFQGLRSFGCRFGTCTVQKLAHQIYQFTDKDKDNVA.

Throughout the specification the "antibodies", or "antibody fragments" or "non-Ig scaffolds" in accordance with the invention are capable to bind ADM, and thus are directed against ADM, and thus can be referred to as "anti-ADM antibodies", "anti-ADM antibody fragments", or "anti-ADM non-Ig scaffolds".

In one embodiment, the ascorbic acid compound is L-ascorbic acid or a pharmaceutically acceptable salt thereof; or a pharmaceutically acceptable solvate or hydrate thereof. L-Ascorbic acid is also known as vitamin C, L-xyloascorbic acid, 3-oxo-L-gulofuranolactone (enol form), L-3-ketothreohexuronic acid lactone, antiscorbutic vitamin, cevitamic acid, adenex, allercorb, ascorin, ascorteal, ascorvit, cantan, cantaxin, catavin C, cebicure, cebion, cecon, cegiolan, celaskon, celin, cenetone, cereon, cergona, cescorbat, cetamid, cetabe, cetemican, cevalin, cevatine, cevex, cevimin, ce-vi-sol, cevitan, cevitex, cewin, ciamin, cipca, concemin, C-vin, daviamon C, duoscorb, hybrin, laroscorbine, lemascorb, planavit C, proscorbin, redoxon, ribena, scorbacid, scorbu-C, testascorbic, vicelat, vitacee, vitacimin, vitacin, vitascorbol, and xitix.

In one embodiment, the ascorbic acid compound is L-ascorbic acid. In another embodiment, the ascorbic acid compound is a pharmaceutically acceptable salt of L-ascorbic acid, or a pharmaceutically acceptable solvate or hydrate thereof.

Suitable bases for forming a pharmaceutically acceptable salt of L-ascorbic acid include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, the ascorbic acid compound is an alkali or alkaline earth metal salt of L-ascorbic acid, or a pharmaceutically acceptable solvate or hydrate thereof. In another embodiment, the ascorbic acid compound is sodium, potassium, calcium, or magnesium L-ascorbate, or a pharmaceutically acceptable solvate or hydrate thereof. In yet another embodiment, the ascorbic acid compound is sodium L-ascorbate, or a pharmaceutically acceptable solvate or hydrate thereof. In yet another embodiment, the ascorbic acid compound is sodium L-ascorbate, which is also known as vitamin C sodium, ascorbin, sodascorbate, natrascorb, cenolate, ascorbicin, or cebitate. In yet another embodiment, the ascorbic acid compound is potassium L-ascorbate, or a pharmaceutically acceptable solvate or hydrate thereof. In yet another embodiment, the ascorbic acid compound is calcium L-ascorbate, or a ascorbic acid compound is calcium L-ascorbate. In yet another embodiment, the ascorbic acid compound is magnesium L-ascorbate, or a pharmaceutically acceptable solvate or hydrate thereof. In still another embodiment, the ascorbic acid compound is magnesium L-ascorbate.

In certain embodiments, the ascorbic acid compound is D-ascorbic acid or a pharmaceutically acceptable salt, or a pharmaceutically acceptable solvate or hydrate thereof.

In one embodiment, the ascorbic acid compound is D-ascorbic acid. In another embodiment, the ascorbic acid compound is a pharmaceutically acceptable salt of D-ascorbic acid, or a pharmaceutically acceptable solvate or hydrate thereof.

Suitable bases for forming a pharmaceutically acceptable salt of D-ascorbic acid include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In one embodiment, the ascorbic acid compound is an alkali or alkaline earth metal salt of D-ascorbic acid, or a pharmaceutically acceptable solvate or hydrate thereof. In another embodiment, the ascorbic acid compound is sodium, potassium, calcium, or magnesium D-ascorbate, or a pharmaceutically acceptable solvate or hydrate thereof. In yet another embodiment, the ascorbic acid compound is sodium D-ascorbate, or a pharmaceutically acceptable solvate or hydrate thereof. In yet another embodiment, the ascorbic acid compound is sodium D-ascorbate, which is also known as vitamin C sodium, ascorbin, sodascorbate, natrascorb, cenolate, ascorbicin, or cebitate. In yet another embodiment, the ascorbic acid compound is potassium D-ascorbate, or a pharmaceutically acceptable solvate or hydrate thereof. In yet another embodiment, the ascorbic acid compound is calcium D-ascorbate, or a ascorbic acid compound is calcium D-ascorbate. In yet another embodiment, the ascorbic acid compound is magnesium D-ascorbate, or a pharmaceutically acceptable solvate or hydrate thereof. In still another embodiment, the ascorbic acid compound is magnesium D-ascorbate.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a non-crystalline form. Where the solvent is water, the solvate is a hydrate. Examples of hydrates include, but are not limited to, a hemihydrate, monohydrate, dihydrate, trihydrate, tetrahydrate, and pentahydrate.

In one embodiment, the ascorbic acid compound in each of the pharmaceutical compositions is independently L-ascorbic acid or a pharmaceutically acceptable salt thereof, or a pharmaceutically acceptable solvate or hydrate thereof. In another embodiment, the ascorbic acid compound in each of the pharmaceutical compositions is independently an alkali or alkaline earth metal salt of L-ascorbic acid, or a pharmaceutically acceptable solvate or hydrate thereof; or a mixture thereof. In yet another embodiment, the ascorbic acid compound in each of the pharmaceutical compositions is independently sodium, potassium, calcium, or magnesium salt of L-ascorbic acid, or a pharmaceutically acceptable solvate or hydrate thereof; or a mixture thereof. In yet another embodiment, the ascorbic acid compound in each of the pharmaceutical compositions is independently sodium L-ascorbate. In yet another embodiment, the ascorbic acid compound in each of the pharmaceutical compositions is independently calcium L-ascorbate. In yet another embodiment, the ascorbic acid compound in each of the pharmaceutical compositions is independently magnesium L-ascorbate. In still another embodiment, the ascorbic acid compound in each of the pharmaceutical compositions is independently a mixture of two or three of sodium L-ascorbate, calcium L-ascorbate, and magnesium L-ascorbate.

In a specific embodiment said anti-ADM antibody or anti-ADM antibody fragment binding to ADM or anti-ADM non-Ig scaffold binding to ADM may be administered in a patient to accelerate the conversion of ADM-Gly to ADM-NH$_2$ with help of a diagnostic method. Said diagnostic method is described below.

Mature ADM, bio-ADM and ADM-NH$_2$ is used synonymously throughout this application and is a molecule according to SEQ ID No.: 20.

Said ratio level is determined that maybe the ratio of the level of pro-Adrenomedullin or a fragment thereof and ADM-NH$_2$ (SEQ ID No. 20), wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34) in a sample of bodily fluid of said subject to the level of bio-ADM determined in a sample of bodily fluid of said subject and said marker ratio is compared to a threshold ratio. If said ratio level of pro-Adrenomedullin or a fragment thereof to ADM-NH$_2$ is above a certain threshold level, the anti-ADM antibody or anti-ADM antibody fragment binding to ADM or anti-ADM non-Ig scaffold binding to ADM is administered as therapy or intervention to said patient.

This means that in a specific embodiment of the present invention said anti-ADM antibody or anti-ADM antibody fragment binding to ADM or anti-ADM non-Ig scaffold binding to ADM is for use in a patient to accelerate the conversion of ADM-Gly to ADM-NH$_2$, wherein a sample of bodily fluid taken from said patient exhibits an elevated level ratio of pro-Adrenomedullin or a fragment thereof to ADM-NH$_2$ above a certain threshold, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34).

Subject matter of the present invention is a diagnostic method, wherein the level of ADM-Gly and ADM-NH$_2$ is determined by using a binder to ADM-Gly and ADM-NH$_2$.

Subject matter of the present invention is a diagnostic method, wherein the binder is selected from the group comprising an antibody, an antibody fragment or a non-Ig-Scaffold binding to pro-Adrenomedullin or a fragment thereof and ADM-NH$_2$, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34).

The term "sample" as used herein refers to a sample of bodily fluid obtained for the purpose of diagnosis, prognosis, or evaluation of a subject of interest, such as a patient. Preferred test samples include blood, serum and plasma. In addition, one of skill in the art would realize that some test samples would be more readily analyzed following a fractionation or purification procedure, for example, separation of whole blood into serum or plasma components.

A bodily fluid according to the present invention is in one particular embodiment a blood sample. A blood sample may be selected from the group comprising whole blood, serum and plasma. In a specific embodiment of the diagnostic method said sample is selected from the group comprising human citrate plasma, heparin plasma and EDTA plasma.

In a specific embodiment of the present invention, an assay is used for determining the ratio of pro-Adrenomedullin or a fragment thereof and ADM-NH$_2$, wherein said level of pro-Adrenomedullin or a fragment thereof is selected from the group consisting of PAMP (SEQ ID No. 32), MR-proADM (SEQ ID No. 33), ADM-Gly (SEQ ID No. 21) and CT-proADM (SEQ ID No. 34), wherein the assay sensitivity of said assay for ADM-NH$_2$ is able to quantify the mature ADM-NH$_2$ of healthy subjects and is <70 pg/ml, preferably <40 pg/ml and more preferably <10 pg/ml.

In a specific embodiment of the present invention, an assay is used for determining the ratio of pro-Adrenomedullin or a fragment thereof and ADM-NH$_2$, wherein said level of pro-Adrenomedullin or a fragment thereof is ADM-Gly (SEQ ID No. 21) and wherein the assay sensitivity of said assay for ADM-Gly is able to quantify ADM-Gly of healthy subjects and is pg/ml, preferably 15 pg/ml and more preferably 10 pg/ml.

In a specific embodiment of the present invention, an assay is used for determining the ratio of pro-Adrenomedullin or a fragment thereof and ADM-NH$_2$, wherein said level of pro-Adrenomedullin or a fragment thereof is MR-proADM (SEQ ID No. 33) and wherein the assay sensitivity of said assay is able to quantify MR-proADM of healthy subjects and is <0.5 nmol/L, preferably <0.4 nmol/L and more preferably <0.2 nmol/L.

In a specific embodiment of the present invention, an assay is used for determining the ratio of pro-Adrenomedullin or a fragment thereof and ADM-NH$_2$, wherein said level of pro-Adrenomedullin or a fragment thereof is CT-proADM (SEQ ID No. 34) and wherein the assay sensitivity of said assay is able to quantify CT-proADM of healthy subjects and is <100 pmol/L, preferably <75 pmol/L and more preferably <50 pmol/L.

In a specific embodiment of the present invention, an assay is used for determining the ratio of pro-Adrenomedullin or a fragment thereof and ADM-NH$_2$, wherein said level of pro-Adrenomedullin or a fragment thereof is PAMP (SEQ ID No. 34) and wherein the assay sensitivity of said assay is able to quantify PAMP of healthy subjects and is <0.5 pmol/L, preferably <0.25 pmol/L and more preferably <0.1 pmol/L.

In one embodiment of the subject matter of the present invention the ratio threshold of ADM-Gly and ADM-NH$_2$ is in a range between 1 and 10, preferably between 1.5 and 7.5, preferably between 2 and 5, most preferred the threshold is 2.5.

For the calculation of the ratio, the concentration of the two markers has to be preferably expressed in the same unit (e.g., pg/ml).

Both marker levels are used to conduct a calculation which maybe either a ratio of both markers (e.g., ratio between ADM-Gly and ADM-NH$_2$ or ratio between ADM-NH$_2$ and ADM-Gly), or a mathematical formula in which both markers are introduced or a mathematical algorithm in which both markers are introduced. The outcome of such a ratio or mathematical formula or mathematical algorithm maybe a value that is then compared with a predetermined threshold value and this comparison is then used in a patient to accelerate the conversion of ADM-Gly to ADM-NH$_2$ with an anti-ADM antibody or anti-ADM antibody fragment binding to ADM or anti-ADM non-Ig scaffold binding to ADM.

Threshold levels can be obtained for instance from a Kaplan-Meier analysis, where the occurrence of a disease is correlated with the quartiles of the marker ratio in the population. According to this analysis, subjects with marker ratios above, e.g., the 75th percentile have a significantly increased risk, e.g., for getting the diseases or suffering from an adverse event (e.g., mortality) according to the invention.

Other preferred threshold values are for instance the 90th, 95th or 99th percentile of a normal population. By using a higher percentile than the 75th percentile, one reduces the number of false positive subjects identified, but one might miss to identify subjects, who are at moderate, albeit still increased risk. Thus, one might adopt the threshold value depending on whether it is considered more appropriate to identify most of the subjects at risk at the expense of also identifying "false positives", or whether it is considered more appropriate to identify mainly the subjects at high risk at the expense of missing several subjects at moderate risk.

The above-mentioned threshold values might be different when using other assays, if these have been calibrated differently from the assay systems used in the present invention. Therefore, the above-mentioned thresholds shall apply for such differently calibrated assays accordingly, taking into account the differences in calibration. One possibility of quantifying the difference in calibration is a method comparison analysis (correlation) of the assays in question (e.g., bio-ADM assay) with the respective biomarker assay used in the present invention by measuring the respective biomarker (e.g., bio-ADM) in samples using both methods. Another possibility is to determine with the assay in question, given this test has sufficient analytical sensitivity, the median biomarker level of a representative normal population, compare results with the median biomarker levels as described in the literature (e.g., Weber et al. 2017. *JALM* 2(2): 222-233) and recalculate the calibration based on the difference obtained by this comparison. With the calibration used in the present invention, samples from normal (healthy) subjects have been measured: median plasma bio-ADM (mature ADM-NH$_2$) was 13.7 pg/ml (inter quartile range [IQR] 9.6-18.7 pg/mL) (Weber et al. 2017. *JALM* 2(2): 222-233).

In a specific embodiment of the diagnostic method, said binder exhibits a binding affinity to pro-Adrenomedullin or a fragment thereof (which is not ADM-NH$_2$ according to SEQ ID No.: 20) and ADM-NH$_2$ of at least $10^7$ M$^{-1}$, preferred $10^8$ M$^{-1}$, preferred affinity is greater than $10^9$ M$^{-1}$, most preferred greater than $10^{10}$ M$^{-1}$. A person skilled in the art knows that it may be considered to compensate lower affinity by applying a higher dose of compounds and this measure would not lead out-of-the-scope of the invention.

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare), (Lorenz et al. 2011. *Antimicrob Agents Chemother.* 55 (1): 165-173).

In a specific embodiment of the diagnostic method, an assay is used for determining the level of pro-Adrenomedullin or a fragment thereof and ADM-NH$_2$, wherein said level of pro-Adrenomedullin or a fragment thereof is selected from the group consisting of PAMP (SEQ ID No. 32), MR-proADM (SEQ ID No. 33), ADM-Gly (SEQ ID No. 21) and CT-proADM (SEQ ID No. 34) and wherein such assay is a sandwich assay, preferably a fully automated assay.

In one embodiment of the invention, it may be a so-called POC-test (point-of-care) that is a test technology, which allows performing the test within less than 1 hour near the patient without the requirement of a fully automated assay system. One example for this technology is the immuno-chromatographic test technology.

In one embodiment of the diagnostic method such an assay is a sandwich immunoassay using any kind of detection technology including but not restricted to enzyme label, chemiluminescence label, electrochemiluminescence label, preferably a fully automated assay. In one embodiment of the diagnostic method such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, BiomerieuxVidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immuno-chromatography assays.

In a specific embodiment of the diagnostic method, at least one of said two binders is labeled in order to be detected.

Subject matter of the present invention is an anti-adrenomedullin (ADM) antibody or an anti-adrenomedullin antibody fragment or anti-ADM non-Ig scaffold for use in a patient to accelerate the conversion of ADM-Gly to ADM-NH$_2$, wherein said patient is a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia.

Heart failure (HF) is a cardiac condition that occurs, when a problem with the structure or function of the heart impairs its ability to supply sufficient blood flow to meet the body's needs. It can cause a large variety of symptoms, particularly shortness of breath (SOB) at rest or during exercise, signs of fluid retention such as pulmonary congestion or ankle swelling and objective evidence of an abnormality of the structure or function of the heart at rest.

Heart failure is a clinical syndrome characterized by a constellation of symptoms and signs caused by cardiac dysfunction. It is one of the major causes of morbidity and mortality in the developed countries, with a prevalence of 1-2%. Heart failure can be grouped into chronic HF and acute HF. Patients with chronic HF can be grouped into stable chronic HF, worsening signs and symptoms of chronic HF and acute decompensation of chronic HF. Acute heart failure (AHF) is defined as a rapid onset of signs and symptoms of heart failure resulting in the need for urgent therapy or hospitalization. AHF can present as acute de novo HF (new onset of AHF in a patient without previous cardiac dysfunction) or acute decompensation of chronic HF. AHF is the leading cause of hospitalization in adults older than 65 years of age. Despite marked improvements in the prognosis of chronic heart failure patients primarily related to therapeutic advances over the past few decades, both short- and long-term outcomes remain very poor once patients are hospitalized for decompensated heart failure. Nearly 25% of patients hospitalized for AHF need readmission within 30 days of hospital discharge while <50% survive beyond 5 years after hospitalization.

Heart failure comprises a wide range of patients, from those with normal left ventricular ejection fraction (LVEF) typically considered as ≥50%, also known as HF with preserved EF (HFpEF) to those with reduced LVEF, typically considered as <40%, also known as HF with reduced EF (HFrEF). Patients with an LVEF in the range of 40-49% represent a 'grey area', which is defined as HF with mid-range EF (HFmrEF) (Ponikowski et al. 2016. *European Heart Journal* 18(8): 891-975).

Symptoms/signs of congestion (left-sided) are defined as orthopnoea, paroxysmal nocturnal dyspnoea, pulmonary rales (bilateral), peripheral edema (bilateral). Symptoms/ signs of congestion (right-sided) are defined as jugular venous dilatation, peripheral edema (bilateral), congested hepatomegaly, hepatojugular reflux, ascites, symptoms of gut congestion (for review see table 12.2 in Ponikowski et al. 2016. *Eur Heart J.* ehw128).

Edema is an accumulation of fluid in the intercellular tissue that results from an abnormal expansion in interstitial fluid volume. The fluid between the interstitial and intravascular spaces is regulated by the capillary hydrostatic pressure gradient and the oncotic pressure gradient across the capillary (Trayes et al. 2013. *Am Fam Physician* 88(2): 102-110). The accumulation of fluid occurs when local or systemic conditions disrupt this equilibrium, leading to increased capillary hydrostatic pressure, increased plasma volume, decreased plasma oncotic pressure (hypoalbuminemia), increased capillary permeability, or lymphatic obstruction.

Clinically, edema manifests as swelling: the amount of interstitial fluid is determined by the balance of fluid homeostasis, and the increased secretion of fluid into the interstitium, or the impaired removal of the fluid can cause edema. A rise in hydrostatic pressure occurs in cardiac failure. Causes of edema which are generalized to the whole body can cause edema in multiple organs and peripherally. For example, severe heart failure can cause pulmonary edema, pleural effusions, ascites and peripheral edema.

Pulmonary edema is fluid accumulation in the air spaces and parenchyma of the lungs. It leads to impaired gas exchange and may cause respiratory failure. It is due to either failure of the left ventricle of the heart to adequately remove blood from the pulmonary circulation ("cardiogenic pulmonary edema"), or an injury to the lung parenchyma or vasculature of the lung ("noncardiogenic pulmonary edema") (Ware and Matthay 2005. *N. Engl. J. Med.* 353 (26): 2788-96). Treatment is focused on three aspects: firstly, improving respiratory function, secondly, treating the underlying cause, and thirdly avoiding further damage to the lung. Pulmonary edema, especially acute, can lead to fatal respiratory distress or cardiac arrest due to hypoxia. It is a cardinal feature of congestive heart failure.

The term "acute" is used to mean rapid onset and to describe exacerbated or decompensated heart failure, referring to episodes in which a patient can be characterized as having a change in heart failure signs and symptoms resulting in a need for urgent therapy or hospitalization.

The term "chronic" refers to long duration. Chronic heart failure is a long-term condition, usually kept stable by the treatment of symptoms (stable chronic HF).

Stable chronic HF is characterized by: the presence of structural or functional failure of the heart that impairs its ability to supply sufficient blood flow to meet body's needs, the absence of volume overload (manifested by pulmonary and/or systemic congestion) and/or profound depression of cardiac output (manifested by hypotension, renal insufficiency and/or a shock syndrome), and whereas the patient is not in need of urgent therapy or therapy adjustment and does not require hospitalization.

Chronic HF with worsening signs and symptoms is characterized by: the presence of structural or functional failure of the heart that impairs its ability to supply sufficient blood flow to meet body's needs, volume overload (manifested by pulmonary and/or systemic congestion) and/or profound depression of cardiac output (manifested by hypotension, renal insufficiency and/or a shock syndrome), and whereas the patient is not in need of urgent therapy and does not require hospitalization, but is in need of therapy adjustment.

Chronic heart failure may also decompensate (termed acute decompensated heart failure or acute decompensated chronic heart failure), which is most commonly the result from an intercurrent illness (such as pneumonia), myocardial infarction, arrhythmias, uncontrolled hypertension or a patient's failure to maintain fluid restriction, diet or medication. After treatment, patients with acute decompensated chronic HF may return to a stable chronic compensated status (stable chronic HF).

New onset acute HF and acute decompensated chronic HF are characterized by: the presence of structural or functional failure of the heart that impairs its ability to supply sufficient blood flow to meet body's needs, volume overload (manifested by pulmonary and/or systemic congestion) and/or profound depression of cardiac output (manifested by hypotension, renal insufficiency and/or a shock syndrome), and whereas the patient is in need of urgent therapy or therapy adjustment and does require hospitalization.

Sepsis is defined as life-threatening organ dysfunction caused by a dysregulated host response to infection (see Singer et al. 2016. *JAMA* 315(8): 801-810). Organ dysfunction can be identified as an acute change in total SOFA score ≥2 points consequent to the infection. The baseline SOFA score can be assumed to be zero in patients not known to have preexisting organ dysfunction. A SOFA score ≥2 reflects an overall mortality risk of approximately 10% in a general hospital population with suspected infection. Even patients presenting with modest dysfunction can deteriorate further, emphasizing the seriousness of this condition and the need for prompt and appropriate intervention, if not already being instituted. Sepsis is a life-threatening condition that arises when the body's response to an infection injures its own tissues and organs. Patients with suspected infection who are likely to have a prolonged ICU stay or to die in the hospital can be promptly identified at the bedside with qSOFA, i.e., alteration in mental status, systolic blood pressure ≤100 mm Hg, or respiratory rate ≥22/min.

Septic shock is a subset of sepsis in which underlying circulatory and cellular/metabolic abnormalities are profound enough to substantially increase mortality. Patients with septic shock can be identified with a clinical construct of sepsis with persisting hypotension requiring vasopressors to maintain mean arterial pressure (MAP)≥65 mm Hg and having a serum lactate level >2 mmol/L (18 mg/dL) despite adequate volume resuscitation. With these criteria, hospital mortality is in excess of 40%.

Dementia is a clinical syndrome characterized by a cluster of symptoms and signs manifested by difficulties in memory, disturbances in language, psychological and psychiatric changes, and impairments in activities of daily living. The different causes (sometimes referred to as subtyping) of dementia syndrome are Alzheimer's disease (about 50% of cases), vascular dementia (about 25%), mixed Alzheimer's disease and vascular dementia (included in the above, 25%), Lewy body dementia (15%) and others (about 5% combined) including frontotemporal dementia, focal dementias (such as progressive aphasia), subcortical dementias (such as Parkinson's disease dementia), and secondary causes of dementia syndrome (such as intracranial lesions).

Alzheimer's disease (AD) is the most prevalent form of dementia. AD is increasing rapidly in frequency as the world's population ages and more people enter the major risk period for this age-related disorder. From the 5.3 million US citizens affected now, the number of victims will increase to 13 million or more by 2050; worldwide the total number of affected individuals will increase to a staggering 100 million (*Alzheimer's Association*. 2015 *Alzheimer's disease facts and figures. Alzheimers Dement* 11: 332-84). Key molecular mechanisms and histopathological hallmarks in the AD brain comprise a dynamic cascade of biochemical events including the pathological amyloidogenic cleavage of the amyloid precursor protein (APP), the generation of various beta-amyloid species including the amyloid-beta peptide ($A\beta_{1-42}$), dimers, trimers, oligomers and subsequent amyloid aggregation and deposition in plaques, abnormal hyperphosphorylation and aggregation of tau protein, progressive intracellular neurofibrillary degeneration, changes within the innate immune system and inflammation.

About 5% of patients develop symptoms before age 65 and are characterized as patients with "early-onset Alzheimer's disease" (EOAD). Most of these patients have the sporadic form of the disease, but 10-15% have a genetic form that is generally inherited as an autosomal dominant fashion. Three genes have been suggested to be involved in the development of EOAD: Presenilin 1 and 2 and the amyloid precursor protein (APP) gene. Other candidate genes are also under investigation. Genetic forms tend to start at age 30 or 40 and have an aggressive course while sporadic EOAD tend to start after age 50 and have, in general, a temporal profile similar to the "late onset Alzheimer's disease" (LOAD) one.

Mental status testing evaluates memory, ability to solve simple problems and other thinking skills. Such tests give an overall sense of whether a person is aware of symptoms, knows the date, time, and where he or she is, can remember a short list of words, follow instructions and do simple calculations. The mini-mental state exam (MMSE) and the mini-cog test are two commonly used tests. The MMSE or Folstein test is a 30-point questionnaire that is used extensively in clinical and research settings to measure cognitive impairment (Pangman, et al. 2000. *Applied Nursing Research* 13 (4): 209-213; Folstein et al. 1975. *Journal of Psychiatric Research*. 12 (3): 189-98). During the MMSE, a health professional asks a patient a series of questions designed to test a range of everyday mental skills. The maximum MMSE score is 30 points. A score of 20 to 24 suggests mild dementia, 13 to 20 suggests moderate dementia, and less than 12 indicates severe dementia. On average, the MMSE score of a person with Alzheimer's declines about two to four points each year. Advantages to the MMSE include requiring no specialized equipment or training for administration, and has both validity and reliability for the diagnosis and longitudinal assessment of Alzheimer's disease. During the mini-cog, a person is asked to complete two tasks, remember and a few minutes later repeat the names of three common objects and draw a face of a clock showing all 12 numbers in the right places and a time specified by the examiner. The results of this brief test can help a physician determine if further evaluation is needed. Other tests are also used, such as the Hodkinson abbreviated mental test score (Hodkinson 1972. *Age and ageing*. 1 (4): 233-8) or the General Practitioner Assessment of Cognition, computerized tests such as CoPs and Mental Attributes Profiling System as well as longer formal tests for deeper analysis of specific deficits.

Mild cognitive impairment (MCI) is a heterogeneous clinical condition with several underlying causes. However, the large proportion of MCI represents a transitional state between healthy aging and very mild AD (DeCarli 2003. *Lancet Neurol*. 2: 15-21). Accordingly, studies suggest that MCI subjects tend to progress to clinically probable AD at a rate of approximately 10%-15% per year (Markesbery 2010. *J Alzheimers Dis*. 19: 221-228).

Alzheimer's disease is usually diagnosed based on the person's medical history, history from relatives, and behavioral observations. The presence of characteristic neurological and neuropsychological features and the absence of alternative conditions is supportive. Advanced medical imaging with computed tomography (CT) or magnetic resonance imaging (MRI), and with single-photon emission computed tomography (SPECT) or positron emission tomography (PET) can be used to help exclude other cerebral pathology or subtypes of dementia. Moreover, it may predict conversion from prodromal stages (mild cognitive impairment) to Alzheimer's disease. Assessment of intellectual functioning including memory testing can further characterize the state of the disease. Medical organizations have created diagnostic criteria to ease and standardize the diagnostic process for practicing physicians. The diagnosis can be confirmed with very high accuracy post-mortem when brain material is available and can be examined histologically.

To date, only symptomatic treatments exist for this disease, all trying to counterbalance the neurotransmitter disturbance. Three cholinesterase inhibitors are currently available and have been approved for the treatment of mild to moderate AD. A further therapeutic option available for moderate to severe AD is memantine, an N-methyl-D-aspartate receptor noncompetitive antagonist. Treatments capable of stopping or at least effectively modifying the course of AD, referred to as 'disease-modifying' drugs, are still under extensive research.

New therapies are urgently needed to treat affected patients and to prevent, defer, slow the decline, or improve the symptoms of AD. It has been estimated that the overall frequency of the disease would be decreased by nearly 50% if the onset of the disease could be delayed by 5 years. Symptomatic treatments are drugs aimed at cognitive enhancement or control of neuropsychiatric symptoms and typically work through neurotransmitter mechanisms; disease-modifying therapies or treatments (DMTs) are agents that prevent, delay, or slow progression and target the underlying pathophysiologic mechanisms of AD. Currently there are more than 100 agents in the AD treatment development pipeline (Cummings et al. 2017. *Alzheimer's & Dementia: Translational Research & Clinical Interventions* 3: 367-384).

Dementia with Lewy bodies (DLB) is a type of dementia that worsens over time. Additional symptoms may include fluctuations in alertness, visual hallucinations, slowness of movement, trouble walking, and rigidity. DLB is the most common cause of dementia after Alzheimer's disease and vascular dementia. It typically begins after the age of 50. About 0.1% of those over 65 are affected. Men appear to be more commonly affected than women. The underlying mechanism involves the formation of Lewy bodies in neurons, consisting of alpha-synuclein protein. A diagnosis may be suspected based on symptoms, with blood tests and medical imaging done to rule out other possible causes. At present no cure for DLB exists. Treatments are supportive and attempt to relieve some of the motor and psychological symptoms associated with the disease. Acetylcholinesterase inhibitors, such as donepezil, may provide some benefit. Some motor problems may improve with levodopa. For review see McKeith et al. 2017. *Neurology* 89: 88-100.

Vascular dementia (VaD), also known as multi-infarct dementia (MID) and vascular cognitive impairment (VCI), is dementia caused by problems in the supply of blood to the brain, typically a series of minor strokes, leading to worsening cognitive decline that occurs step by step. The term refers to a syndrome consisting of a complex interaction of cerebrovascular disease and risk factors that lead to changes in the brain structures due to strokes and lesions, and resulting changes in cognition. The temporal relationship between a stroke and cognitive deficits is needed to make the diagnosis. Differentiating the different dementia syndromes can be challenging, due to the frequently overlapping clinical features and related underlying pathology. In particular, Alzheimer's dementia often co-occurs with vascular dementia. People with vascular dementia present with progressive cognitive impairment, acutely or sub-acutely as in mild cognitive impairment, frequently step-wise, after multiple cerebrovascular events (strokes). For review see Venkat et al. 2015. *Exp Neurol* 272: 97-108.

Frontotemporal dementia (FTD) is the clinical presentation of frontotemporal lobar degeneration, which is characterized by progressive neuronal loss predominantly involving the frontal or temporal lobes, and typical loss of over 70% of spindle neurons, while other neuron types remain intact. FTD accounts for 20% of young-onset dementia cases. Signs and symptoms typically manifest in late adulthood, more commonly between the ages of 55 and 65, approximately equally affecting men and women. Common signs and symptoms include significant changes in social and personal behavior, apathy, blunting of emotions, and deficits in both expressive and receptive language. Currently, there is no cure for FTD, but there are treatments that help alleviate symptoms. For review see Bott et al. 2014. *Neurodegener Dis Manag* 4(6): 439-454.

In one specific embodiment, wherein said anti-ADM antibody or anti-ADM fragment or anti-ADM non-Ig scaffold binds to the N-terminal part (amino acid 1-21) of ADM-Gly and/or ADM-NH$_2$: YRQSMNNFQGLRSFGCRFGTC (SEQ ID No. 14), the patient is not suffering from the disease or condition dementia or Alzheimer's disease.

In another specific embodiment the present application relates to an anti-adrenomedullin (ADM) antibody or an anti-adrenomedullin antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) in order to accelerate the conversion of ADM-Gly to ADM-NH$_2$ of circulating ADM-Gly in said patient, wherein said anti-ADM antibody or anti-ADM fragment or anti-ADM non-Ig scaffold binds to the N-terminal part (amino acid 1-21) of ADM-Gly and/or ADM-NH$_2$: YRQSMNNFQGLRSFGCRFGTC (SEQ ID No. 14), wherein said disease or condition is not dementia or Alzheimer's disease.

As used herein, organ dysfunction denotes a condition or a state of health where an organ does not perform its expected function. "Organ failure" denotes an organ dysfunction to such a degree that normal homeostasis cannot be maintained without external clinical intervention. Said organ failure may pertain an organ selected from the group comprising kidney, liver, heart, lung, nervous system. By contrast, organ function represents the expected function of the respective organ within physiologic ranges. The person skilled in the art is aware of the respective function of an organ during medical examination.

Organ dysfunction may be defined by the sequential organ failure assessment score (SOFA-Score) or the components thereof. The SOFA score, previously known as the sepsis-related organ failure assessment score (Singer et al. 2016. *JAMA* 315(8): 801-10) is used to track a person's status during the stay in an intensive care unit (ICU) to determine the extent of a person's organ function or rate of failure. The score is based on six different scores, one each for the respiratory, cardiovascular, hepatic, coagulation, renal and neurological systems each scored from 0 to 4 with an increasing score reflecting worsening organ dysfunction. The criteria for assessment of the SOFA score are described for example in Lamden et al. (for review see Lambden et al. 2019. *Critical Care* 23: 374). SOFA score may traditionally be calculated on admission to ICU and at each 24-h period that follows. In particular, said organ dysfunction is selected from the group comprising renal decline, cardiac dysfunction, liver dysfunction or respiratory tract dysfunction.

The quick SOFA Score (quickSOFA or qSOFA) was introduced by the Sepsis-3 group in February 2016 as a simplified version of the SOFA Score as an initial way to identify patients at high risk for poor outcome with an infection (Angus et al. 2016. *Critical Care Medicine*. 44 (3): e113-e121). The qSOFA simplifies the SOFA score drastically by only including its 3 clinical criteria and by including "any altered mentation" instead of requiring a GCS<15. qSOFA can easily and quickly be repeated serially on patients. The score ranges from 0 to 3 points. One point is given for: low blood pressure (SBP≤100 mm Hg), high respiratory rate ((≥22 breaths/min) and altered mentation (GCS≤15). The presence of 2 or more qSOFA points near the onset of infection was associated with a greater risk of death or prolonged intensive care unit stay. These are outcomes that are more common in infected patients who may be septic than those with uncomplicated infection. Based upon these findings, the Third International Consensus Definitions for Sepsis recommends qSOFA as a simple prompt to identify infected patients outside the ICU who are likely to be septic (Seymour et al. 2016. *JAMA* 315(8): 762-774).

The term "to accelerate the conversion" is defined in the present application as an increased conversion of glycinated adrenomedullin (ADM-Gly) to mature ADM (ADM-NH$_2$) in presence of an anti-ADM antibody or an anti-adrenomedullin antibody fragment or an anti-ADM non-Ig scaffold within a certain period of time.

Furthermore, in one embodiment of the invention the anti-adrenomedullin (ADM) antibody or anti-adrenomedullin antibody fragment or anti-ADM non-Ig scaffold is monospecific.

Monospecific means that said antibody or antibody fragment or non-Ig scaffold binds to one specific region encompassing at least 4 amino acids within the target ADM. Monospecific antibodies or fragments or non-Ig scaffolds according to the invention are antibodies or fragments or non-Ig scaffolds that all have affinity for the same antigen. Monoclonal antibodies are monospecific, but monospecific antibodies may also be produced by other means than producing them from a common germ cell.

Said anti-ADM antibody or antibody fragment binding to ADM or non-Ig scaffold binding to ADM may be a non-neutralizing anti-ADM antibody or antibody fragment binding to ADM or non-Ig scaffold binding to ADM.

An antibody or fragment according to the present invention is a protein including one or more polypeptides substantially encoded by immunoglobulin genes that specifically binds an antigen. The recognized immunoglobulin genes include the kappa, lambda, alpha (IgA), gamma (IgG$_1$, IgG$_2$, IgG$_3$, IgG$_4$), delta (IgD), epsilon (IgE) and mu (IgM) constant region genes, as well as the myriad immunoglobulin variable region genes. Full-length immunoglobulin light chains are generally about 25 Kd or 214 amino acids in length.

Full-length immunoglobulin heavy chains are generally about 50 Kd or 446 amino acid in length. Light chains are encoded by a variable region gene at the NH$_2$-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al. 1987. *Eur. J. Immunol.* 17:105; Huston et al. 1988. *Proc. Natl. Acad. Sci. U.S.A.,* 85: 5879-5883; Bird et al. 1988. *Science* 242: 423-426; Hood et al. 1984, *Immunology*, Benjamin, N.Y., 2nd ed.; Hunkapiller and Hood 1986. *Nature* 323: 15-16). An immunoglobulin light or heavy chain variable region includes a framework region interrupted by three hypervariable regions, also called complementarity determining regions (CDR's) (see, *Sequences of Proteins of Immunological Interest*, E. Kabat et al. 1983, U.S. Department of Health and Human Services). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest Immortalization can be accomplished, for example, by EBV infection or by fusing a human B cell with a myeloma or hybridoma cell to produce a trioma cell. Human antibodies can also be produced by phage display methods (see, e.g., WO91/17271; WO92/001047; WO92/20791), or selected from a human combinatorial monoclonal antibody library (see the Morphosys website). Human antibodies can also be prepared by using transgenic animals carrying a human immunoglobulin gene (for example, see WO93/12227; WO 91/10741).

Thus, the anti-ADM antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as, e.g., IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')$_2$-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g., from a different class than G; single-domain antibodies, e.g. nanobodies derived from camelid or fish immunoglobulines and numerous others.

In addition to anti-ADM antibodies other biopolymer scaffolds are well known in the art to complex a target molecule and have been used for the generation of highly target specific biopolymers. Examples are aptamers, spiegelmers, anticalins and conotoxins. For illustration of antibody formats please see FIGS. 1*a*, 1*b* and 1*c*.

In a preferred embodiment the anti-ADM antibody format is selected from the group comprising Fv fragment, scFv fragment, Fab fragment, scFab fragment, F(ab)$_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Non-Ig scaffolds may be protein scaffolds and may be used as antibody mimics as they are capable to bind to ligands or antigens. Non-Ig scaffolds may be selected from the group comprising tetranectin-based non-Ig scaffolds (e.g., described in US 2010/0028995), fibronectin scaffolds (e.g., described in EP 1 266 025; lipocalin-based scaffolds (e.g. described in WO 2011/154420); ubiquitin scaffolds (e.g. described in WO 2011/073214), transferrin scaffolds (e.g., described in US 2004/0023334), protein A scaffolds (e.g. described in EP 2 231 860), ankyrin repeat based scaffolds (e.g., described in WO 2010/060748), micropro-teins preferably microproteins forming a cysteine knot) scaffolds (e.g. described in EP 2314308), Fyn SH3 domain based scaffolds (e.g., described in WO 2011/023685) EGFR-A-domain based scaffolds (e.g. described in WO 2005/040229) and Kunitz domain based scaffolds (e.g., described in EP 1 941 867).

In one embodiment of the invention anti-ADM antibodies according to the present invention may be produced as outlined in Example 1 by synthesizing fragments of ADM as antigens. Thereafter, binder to said fragments are identified using the below described methods or other methods as known in the art.

Humanization of murine antibodies may be conducted according to the following procedure: For humanization of an antibody of murine origin the antibody sequence is analyzed for structural interaction of framework regions (FR) with the complementary determining regions (CDR) and the antigen. Based on structural modelling an appropri-ate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modelling (Almagro and Fransson 2008. *Front Biosci.* 13: 1619-33).

In another preferred embodiment, the anti-ADM anti-body, anti-ADM antibody fragment, or anti-ADM non-Ig scaffold is a full-length antibody, antibody fragment, or non-Ig scaffold.

In a preferred embodiment, the anti-ADM antibody or anti-ADM antibody fragment or anti-ADM non-Ig scaffold is directed to and can bind to an epitope of preferably at least 4 or at least amino acids in length of the N-terminal and/or mid-regional part (amino acid 1-42) of ADM-Gly and/or ADM-NH$_2$:
YRQSMNNFQGLRSFGCRFGTCTVQKLAHQIYQFTD
KDKDNVA (SEQ ID No. 23).

An epitope, also known as antigenic determinant, is the part of an antigen (e.g., peptide or protein) that is recognized by the immune system, specifically by antibodies. For example, the epitope is the specific piece of the antigen to which an antibody binds. The part of an antibody that binds to the epitope is called a paratope. The epitopes of protein antigens are divided into two categories: conformational epitopes and linear epitopes, based on their structure and interaction with the paratope.

A linear or a sequential epitope is an epitope that is recognized by antibodies by its linear sequence of amino acids, or primary structure and is formed by the 3-D con-formation adopted by the interaction of contiguous amino acid residues. Conformational and linear epitopes interact with the paratope based on the 3-D conformation adopted by the epitope, which is determined by the surface features of the involved epitope residues and the shape or tertiary structure of other segments of the antigen. A conformational epitope is formed by the 3-D conformation adopted by the interaction of discontiguous amino acid residues.

In a specific embodiment, the anti-ADM antibody or anti-ADM antibody fragment or anti-ADM non-Ig scaffold is directed to and can bind to preferably at least 4, or at least 5 amino acids within the N-terminal and/or mid-regional part (amino acid 1-42) of ADM-Gly and/or ADM-NH$_2$:

```
                                    (SEQ ID No. 23)
  YRQSMNNFQGLRSFGCRFGTCTVQKLAHQIYQFTDKDKDNVA
``` and needs the free N-terminus (amino acid 1) of ADM and/or ADM-Gly for binding.

In another specific embodiment of the invention the anti-ADM antibody or anti-ADM antibody fragment or anti-ADM non-Ig scaffold is directed to and can bind to preferably at least 4, or at least 5 amino acids within the N-terminal and/or mid-regional part (amino acid 1-42) of ADM-Gly and/or ADM-NH$_2$:

```
                                    (SEQ ID No. 23)
  YRQSMNNFQGLRSFGCRFGTCTVQKLAHQIYQFTDKDKDNVA
``` and does not bind the free N-terminus (amino acid 1) of ADM and/or ADM-Gly.

In one specific embodiment of the invention the anti-ADM antibody or anti-ADM antibody fragment or anti-ADM non-Ig scaffold is directed to and can bind to prefer-ably at least 4, or at least 5 amino acids within the N-terminal part (amino acid 1-21) of ADM-Gly and/or ADM-NH$_2$: YRQSMNNFQGLRSFGCRFGTC (SEQ ID No.: 14).

In one specific embodiment of the invention the anti-ADM antibody or anti-ADM antibody fragment or anti-ADM non-Ig scaffold is directed to and can bind to prefer-ably at least 4, or at least 5 amino acids within the N-terminal part (amino acid 1-21) of ADM-Gly and/or ADM-NH$_2$: YRQSMNNFQGLRSFGCRFGTC (SEQ ID No.: 14) and needs the free N-terminus (amino acid 1) of ADM and/or ADM-Gly for binding.

In one specific embodiment of the invention the anti-ADM antibody or anti-ADM antibody fragment or anti-ADM non-Ig scaffold is directed to and can bind to prefer-ably at least 4, or at least 5 amino acids within the N-terminal part (amino acid 1-21) of ADM-Gly and/or ADM-NH$_2$: YRQSMNNFQGLRSFGCRFGTC (SEQ ID No.: 14) and does not bind the free N-terminus (amino acid 1) of ADM and/or ADM-Gly.

In another preferred embodiment said anti-ADM-anti-body or anti-ADM antibody fragment or anti-ADM non-Ig scaffold is directed to and can bind to preferably at least 4, or at least 5 amino acids within the N-terminal part (amino acid 1-14) of ADM-Gly and/or ADM-NH$_2$:

```
                                    (SEQ ID No.: 25)
                YRQSMNNFQGLRSF.
```

In another preferred embodiment said anti-ADM-anti-body or anti-ADM antibody fragment or anti-ADM non-Ig scaffold is directed to and can bind to preferably at least 4, or at least 5 amino acids within the N-terminal part (amino acid 1-14) of ADM-Gly and/or ADM-NH$_2$: YRQSMNNFQGLRSF (SEQ ID No.: 25) and needs the free N-terminus (amino acid 1) of ADM and/or ADM-Gly for binding.

In another preferred embodiment said anti-ADM-antibody or anti-ADM antibody fragment or anti-ADM non-Ig scaffold is directed to and can bind to preferably at least 4, or at least 5 amino acids within the N-terminal part (amino acid 1-14) of ADM-Gly and/or ADM-NH₂: YRQSMNNFQGLRSF (SEQ ID No.: 25) and does not bind the free N-terminus (amino acid 1) of ADM and/or ADM-Gly.

In another preferred embodiment said anti-ADM-antibody or anti-ADM antibody fragment or anti-ADM non-Ig scaffold is directed to and can bind to preferably at least 4, or at least 5 amino acids within the N-terminal part (amino acid 1-10) of ADM-Gly and/or ADM-NH₂:

(SEQ ID No.: 26)
YRQSMNNFQG.

In another preferred embodiment said anti-ADM-antibody or anti-ADM antibody fragment or anti-ADM non-Ig scaffold is directed to and can bind to preferably at least 4, or at least 5 amino acids within the N-terminal part (amino acid 1-10) of ADM-Gly and/or ADM-NH₂: YRQSMNNFQG (SEQ ID No.: 26) and needs the free N-terminus (amino acid 1) of ADM and/10 or ADM-Gly for binding.

In another preferred embodiment said anti-ADM-antibody or anti-ADM antibody fragment or anti-ADM non-Ig scaffold is directed to and can bind to preferably at least 4, or at least 5 amino acids within the N-terminal part (amino acid 1-10) of ADM-Gly and/or ADM-NH₂: YRQSMNNFQG (SEQ ID No.: 26) and does not bind the free N-terminus (amino acid 1) of ADM and/or ADM-Gly.

In a very specific embodiment said anti-ADM-antibody or anti-ADM antibody fragment or anti-ADM non-Ig scaffold is directed to and can bind to preferably at least 4, or at least 5 amino acids within the N-terminal part (amino acid 1-6) of ADM-Gly and/or ADM-NH₂: YRQSMN (SEQ ID No.: 27) and needs the free N-terminus (amino acid 1) of ADM and/or ADM-Gly for binding.

In another very specific embodiment of the invention the anti-ADM antibody or anti-adrenomedullin antibody fragment or anti-ADM non-Ig scaffold recognizes and binds to the N-terminal end (amino acid 1) of ADM-Gly and/or ADM-NH₂. N-terminal end means that the amino acid 1, that is "Y" of SEQ ID No. 14, 20, 22, 23, 25, 26, 27 is mandatory for antibody binding. The antibody or fragment or scaffold would neither bind N-terminal extended nor N-terminal modified ADM nor N-terminal degraded ADM-Gly and/or ADM-NH₂. This means that said anti-ADM-antibody or anti-ADM antibody fragment or anti-ADM non-Ig scaffold binds only to a region within the sequence of ADM-Gly and/or ADM-NH₂ if the N-terminal end of ADM is free. The anti-ADM antibody or anti-ADM antibody fragment or non-Ig scaffold would not bind to a region within the sequence of ADM-Gly and/or ADM-NH₂ if said sequence is, e.g., comprised within pro-ADM.

For the sake of clarity, the numbers in brackets for specific regions of ADM like "N-terminal part (amino acid 1-21)" is understood by a person skilled in the art that the N-terminal part of ADM consists of amino acids 1-21 of the ADM-Gly and/or ADM-NH₂ sequence.

In another specific embodiment said anti-ADM-antibody or anti-ADM antibody fragment or anti-ADM non-Ig scaffold is directed to and can bind to preferably at least 4, or at least 5 amino acids within the mid-regional part (amino acid 21-42) of ADM-Gly and/or ADM-NH₂.

In another specific embodiment said anti-ADM-antibody or anti-ADM antibody fragment or anti-ADM non-Ig scaffold is directed to and can bind to preferably at least 4, or at least 5 amino acids within the mid-regional part (amino acid 21-32) of ADM-Gly and/or ADM-NH₂:

(SEQ ID No.: 15)
CTVQKLAHQIYQ.

In another specific embodiment said anti-ADM-antibody or anti-ADM antibody fragment or anti-ADM non-Ig scaffold is directed to and can bind to preferably at least 4, or at least 5 amino acids within the mid-regional part (amino acid 27-39) of ADM-Gly and/or ADM-NH₂:

(SEQ ID No.: 49)
AHQIYQFTDKDKD.

In another specific embodiment pursuant to the invention the herein provided anti-ADM antibody or anti-ADM antibody fragment or anti-ADM non-Ig scaffold does not bind to the C-terminal portion of ADM, i.e., the aa 43-52 of ADM (SEQ ID No.: 24).

In one specific embodiment it is preferred to use an anti-ADM antibody or an anti-adrenomedullin antibody fragment or anti-ADM non-Ig scaffold according to the present invention, wherein said anti-adrenomedullin antibody or said anti-adrenomedullin antibody fragment or non-Ig scaffold leads to an increase of the ADM-NH₂ level or ADM-NH₂ immunoreactivity in serum, blood, plasma of at least 10%, preferably at least 50%, more preferably >50%, most preferably >100%.

An assay that may be used for the determination of the half-life (half retention time) of adrenomedullin in serum, blood, plasma is described in Example 3.

In a specific embodiment of the invention the antibody is a monoclonal antibody or a fragment thereof. In one embodiment of the invention the anti-ADM antibody or the anti-ADM antibody fragment is a human or humanized antibody or derived therefrom. In one specific embodiment one or more (murine) CDR's are grafted into a human antibody or antibody fragment ("humanization").

Subject matter of the present invention in one aspect is a humanized CDR-grafted antibody or antibody fragment thereof, wherein said antibody recognizes or binds to the N-terminal part of ADM-Gly and/or ADM-NH₂ and needs the free N-terminus (amino acid 1) of ADM-Gly and/10 or ADM-NH₂ for binding for use in a patient to accelerate the conversion of ADM-Gly to ADM-NH₂, wherein the humanized CDR-grafted antibody or antibody fragment thereof comprises an antibody heavy chain (H chain) comprising:

SEQ ID No.: 1
GYTFSRYW

SEQ ID No.: 2
ILPGSGST
and/or

SEQ ID No.: 3
TEGYEYDGFDY and/or further comprises an antibody light chain (L chain) comprising:

```
                                    SEQ ID No.: 4
QSIVYSNGNTY

SEQUENCE "RVS" (not part of the Sequencing
Listing):
RVS
and/or

SEQ ID No.: 5

FQGSHIPYT.
```

One specific embodiment of the invention is a humanized and/or human monoclonal antibody or an antibody fragment thereof, wherein said antibody recognizes or binds to the N-terminal part (amino acid 1-21) of ADM-Gly and/or ADM-NH$_2$: YRQSMNNFQGLRSFGCRFGTC (SEQ ID No.: 14) and needs the free N-terminus (amino acid 1) of ADM-Gly and/or ADM-NH$_2$ for binding for use in a patient to accelerate the conversion of ADM-Gly to ADM-NH$_2$ wherein the heavy chain comprises at least one CDR selected from the group comprising:

```
                                    SEQ ID No.: 1
        GYTFSRYW

SEQ ID No.: 2
        ILPGSGST

SEQ ID No.: 3
        TEGYEYDGFDY
``` and wherein the light chain comprises at least one CDR selected from the group comprising:

```
                                    SEQ ID No.: 4
QSIVYSNGNTY

SEQUENCE "RVS" (not part of the Sequencing
Listing):
RVS
and/or

SEQ ID No.: 5
FQGSHIPYT.
```

In a more specific embodiment of the invention subject matter of the invention is a humanized and/or human monoclonal antibody or antibody fragment thereof, wherein said antibody recognizes or binds to the N-terminal part (amino acid 1-21) of ADM-Gly and/or ADM-NH$_2$: YRQSMNNFQGLRSFGCRFGTC (SEQ ID No.: 14) and needs the free N-terminus (amino acid 1) of ADM-Gly and/or ADM-NH$_2$ for binding for use in a patient to accelerate the conversion of ADM-Gly to ADM-NH$_2$ wherein the heavy chain comprises the sequences:

```
                                    SEQ ID No.: 1
        GYTFSRYW

SEQ ID No.: 2
        ILPGSGST

SEQ ID No.: 3
        TEGYEYDGFDY
``` and wherein the light chain comprises the sequences:

```
                                    SEQ ID No.: 4
QSIVYSNGNTY
```

```
                             -continued
SEQUENCE "RVS" (not part of the Sequencing
Listing):
RVS
and/or SEQ ID No.: 5

FQGSHIPYT.
```

In a very specific embodiment, the anti-ADM antibody has a sequence selected from the group comprising: SEQ ID No. 6, 7, 8, 9, 10, 11, 12, 13, 35 and 36.

The anti-ADM antibody or anti-ADM antibody fragment or anti-ADM non-Ig scaffold according to the present invention exhibits an affinity towards human ADM-Gly and/or ADM-NH$_2$ in such that affinity constant is greater than $10^{-7}$ M, preferred $10^{-8}$ M, preferred affinity is greater than $10^{-9}$ M, most preferred higher than $10^{-10}$ M. A person skilled in the art knows that it may be considered to compensate lower affinity by applying a higher dose of compounds and this measure would not lead out-of-the-scope of the invention. The affinity constants may be determined according to the method as described in Example 1.

Subject matter of the present invention is a human or humanized monoclonal antibody or fragment that binds to ADM-Gly and/or ADM-NH$_2$, wherein said antibody or fragment binds to the N-terminal (amino acid 1-21) of ADM-Gly and/or ADM-NH$_2$: YRQSMNNFQGLRSFGCRFGTC (SEQ ID No.: 14) and needs the free N-terminus (amino acid 1) of ADM-Gly and/or ADM-NH$_2$ for binding, for use in a patient to accelerate the conversion of ADM-Gly to ADM-NH$_2$, wherein said antibody or fragment comprises a sequence selected from the group comprising:

```
(AM-VH-C)
                                    SEQ ID No.: 6
QVQLQQSGAELMKPGASVKISCKATGYTFSRYWIEWVKQRPGHGLEWIG

EILPGSGSTNYNEKFKGKATITADTSSNTAYMQLSSLTSEDSAVYYCTE

GYEYDGFDYWGQGTTLTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VH1)
                                    SEQ ID No.: 7
QVQLVQSGAEVKKPGSSVKVSCKASGYTFSRYWISWVRQAPGQGLEWMG

RILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VH2-E40)
                                    SEQ ID No.: 8
QVQLVQSGAEVKKPGSSVKVSCKASGYTFSRYWIEWVRQAPGQGLEWMG

RILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VH3-T26-E55)
                                    SEQ ID No.: 9
QVQLVQSGAEVKKPGSSVKVSCKATGYTFSRYWISWVRQAPGQGLEWMG
```

-continued

```
EILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK
```

(AM-VH4-T26-E40-E55)

SEQ ID No.: 10
```
QVQLVQSGAEVKKPGSSVKVSCKATGYTFSRYWIEWVRQAPGQGLEWMG

EILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK
```

(AM-VL-C)

SEQ ID No.: 11
```
DVLLSQTPLSLPVSLGDQATISCRSSQSIVYSNGNTYLEWYLQKPGQSP

KLLIYRVSNRFSGVPDRFSGSGSGTDFTLKISRVEAEDLGVYYCFQGSH

IPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

(AM-VL1)

SEQ ID No.: 12
```
DVVMTQSPLSLPVTLGQPASISCRSSQSIVYSNGNTYLNWFQQRPGQSP

RRLIYRVSNRDSGVPDRFSGSGSGTDFTLKISRVEAEDVGVYYCFQGSH

IPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

(AM-VL2-E40)

SEQ ID No.: 13
```
DVVMTQSPLSLPVTLGQPASISCRSSQSIVYSNGNTYLEWFQQRPGQSP

RRLIYRVSNRDSGVPDRFSGSGSGTDFTLKISRVEAEDVGVYYCFQGSH

IPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

(heavy chain HAM8101)

SEQ ID No.: 35
```
QVQLVQSGAEVKKPGSSVKVSCKASGYTFSRYWIEWVRQAPGQGLEWIG

EILPGSGSTNYNQKFQGRVTITADTSTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFScSVMHEALHNHYTQKS

LSLSPGK
```

-continued (light chain HAM 8101)

SEQ ID No.: 36
```
DVVLTQSPLSLPVTLGQPASISCRSSQSIVYSNGNTYLEWYLQRPGQSP

RLLIYRVSNRFSGVPDRFSGSGSGTDFTLKISRVEAEDVGVYYCFQGSH

IPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

Subject matter of the present invention is further a human and/or humanized monoclonal antibody or fragment that binds to ADM-Gly and/or ADM-NH$_2$, wherein said antibody or fragment binds to the N-terminal part (amino acid 1-21) of ADM-Gly and/or ADM-NH$_2$: YRQSMNNFQGLRSFGCRFGTC (SEQ ID No.: 14) and needs the free N-terminus (amino acid 1) of ADM-Gly and/or ADM-NH$_2$ for binding for use in a patient to accelerate the conversion of ADM-Gly to ADM-NH$_2$, wherein said antibody or fragment comprises the following sequence as a heavy chain:

SEQ ID No.: 35
```
QVQLVQSGAEVKKPGSSVKVSCKASGYTFSRYWIEWVRQAPGQGLEWIG

EILPGSGSTNYNQKFQGRVTITADTSTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFScSVMHEALHNHYTQKS

LSLSPGK
``` and comprises the following sequence as a light chain:

SEQ ID No.: 36
```
DVVLTQSPLSLPVTLGQPASISCRSSQSIVYSNGNTYLEWYLQRPGQSP

RLLIYRVSNRFSGVPDRFSGSGSGTDFTLKISRVEAEDVGVYYCFQGSH

IPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

In a specific embodiment of the invention the antibody comprises the following sequence as a heavy chain:

SEQ ID No.: 35
```
QVQLVQSGAEVKKPGSSVKVSCKASGYTFSRYWIEWVRQAPGQGLEWIG

EILPGSGSTNYNQKFQGRVTITADTSTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP
```

-continued
```
PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK
``` or a sequence that is >95% identical to it, preferably >98%, preferably >99% and comprises the following sequence as a light chain:

```
                                      SEQ ID No.: 36
DVVLTQSPLSLPVTLGQPASISCRSSQSIVYSNGNTYLEWYLQRPGQSP

RLLIYRVSNRFSGVPDRFSGSGSGTDFTLKISRVEAEDVGVYYCFQGSH

IPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
``` or a sequence that is >95% identical to it, preferably >98%, preferably >99%.

To assess the identity between two amino acid sequences, a pairwise alignment is performed. Identity defines the percentage of amino acids with a direct match in the alignment.

Subject matter of the present invention is a pharmaceutical formulation for use in intervention and therapy of congestion in a patient comprising an antibody or fragment or scaffold according to the present invention.

Subject matter of the present invention is a pharmaceutical formulation for use in a patient to accelerate the conversion of ADM-Gly to ADM-NH$_2$, comprising an antibody or fragment or scaffold according to the present invention, wherein said patient is a critically ill patient suffering from an acute disease or acute condition. Said acute disease or condition is selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms, e.g., congestion or edema), myocardial infarction, stroke, organ dysfunction (e.g., kidney, liver, heart, lung) or dementia.

Subject matter of the present invention is a pharmaceutical formulation for use in intervention and therapy of congestion in a patient according to the present invention wherein said pharmaceutical formulation is a solution, preferably a ready-to-use solution.

Subject matter of the present invention is a pharmaceutical formulation for use in intervention and therapy of congestion in a patient according to the present invention wherein said pharmaceutical formulation is in a freeze-dried state.

Subject matter of the present invention is a pharmaceutical formulation for use in intervention and therapy of congestion in a patient according to the present invention, wherein said pharmaceutical formulation is administered intra-muscular.

Subject matter of the present invention is a pharmaceutical formulation for use in intervention and therapy of congestion in a patient according to the present invention, wherein said pharmaceutical formulation is administered intra-vascular.

Subject matter of the present invention is a pharmaceutical formulation for use in intervention and therapy of congestion in a patient according to the present invention, wherein said pharmaceutical formulation is administered via infusion.

Subject matter of the present invention is a pharmaceutical formulation for use in intervention and therapy of congestion in a patient according to the present invention, wherein said pharmaceutical formulation is to be administered systemically.

With the above context, the following consecutively numbered embodiments provide further specific aspects of the invention:

1. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, wherein said patient is characterized by having a ratio of pro-Adrenomedullin or a fragment thereof to ADM-NH$_2$ (SEQ ID No. 20) above a certain threshold in a sample of bodily fluid, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34) and wherein said anti-ADM antibody or anti-ADM fragment or anti-ADM non-Ig scaffold binds to the N-terminal and/or mid-regional part (amino acid 1-42) of ADM-Gly and/or ADM-NH$_2$:

```
                                      (SEQ ID No. 23)
YRQSMNNFQGLRSFGCRFGTCTVQKLAHQIYQFTDKDKDNVA.
```

2. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiment 1, wherein said anti-ADM antibody or anti-ADM fragment or anti-ADM non-Ig scaffold binds to the N-terminal part (amino acid 1-21) of ADM-Gly and/or ADM-NH$_2$: YRQSMNNFQGLRSFGCRFGTC (SEQ ID No. 14).

3. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, according to embodiments 1 and 2, wherein said anti-ADM antibody or anti-ADM antibody fragment or anti-ADM non-Ig scaffold recognizes and binds to the N-terminal end (amino acid 1) of ADM-Gly and/or ADM-NH$_2$.

4. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, according to embodiment 1, wherein said anti-ADM antibody or anti-ADM fragment or anti-ADM non-Ig scaffold binds to the mid-regional part (amino acid 21-42) of ADM-Gly and/or ADM-NH$_2$: CTVQKLAHQIYQFTDKDKDNVA (SEQ ID No. 48).

5. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient, according to embodiment 4, wherein said anti-ADM antibody or anti-ADM fragment or anti-ADM non-Ig scaffold binds to the mid-regional part (amino acid 21-32) of ADM-Gly and/or ADM-NH$_2$: CTVQKLAHQIYQ (SEQ ID No.: 15).

6. Anti-adrenomedullin (ADM) antibody or anti-ADM antibody fragment or anti-ADM non-Ig scaffold for use in the treatment of a critically ill patient suffering from dementia in order to accelerate the conversion of ADM-Gly to ADM-NH$_2$ of circulating ADM-Gly in said patient, according to claim 1, wherein said anti-ADM antibody or anti-ADM fragment or anti-ADM non-Ig scaffold binds to the mid-regional part (amino acid 21-42) of ADM-Gly and/or ADM-NH$_2$: CTVQKLAHQIYQFTDKDKDNVA (SEQ ID No. 48).

7. Anti-adrenomedullin (ADM) antibody or anti-ADM antibody fragment or anti-ADM non-Ig scaffold for use in the treatment of a critically ill patient suffering from dementia in order to accelerate the conversion of ADM-Gly to ADM-NH$_2$ of circulating ADM-Gly in said patient according to claim 6, wherein said anti-ADM antibody or anti-ADM fragment or anti-ADM non-Ig scaffold binds to the mid-regional part (amino acid 21-32) of ADM-Gly and/or ADM-NH$_2$: CTVQKLAHQIYQ (SEQ ID No.: 15).

8. Anti-adrenomedullin (ADM) antibody or anti-ADM antibody fragment or anti-ADM non-Ig scaffold for use in the treatment of a critically ill patient suffering from dementia in order to accelerate the conversion of ADM-Gly to ADM-NH$_2$ of circulating ADM-Gly in said patient according to claim 6, wherein said anti-ADM antibody or anti-ADM fragment or anti-ADM non-Ig scaffold binds to the mid-regional part (amino acid 27-39) of ADM-Gly and/or ADM-NH$_2$: AHQIYQFTDKDKD (SEQ ID No.: 49).

9. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-8, wherein in a sample of bodily fluid of said patient the level of pro-Adrenomedullin or a fragment thereof consisting of the group of PAMP (SEQ ID No. 32), MR-proADM (SEQ ID No. 33), ADM-Gly (SEQ ID No. 21) and CT-proADM (SEQ ID No. 34) and ADM-NH$_2$ (SEQ ID No. 20) is determined.

10. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-9, wherein in a sample of bodily fluid of said patient a ratio of the level of ADM-Gly (SEQ ID No. 21) and ADM-NH$_2$ (SEQ ID No. 20) is determined and the patient is treated with said anti-ADM antibody or an anti-ADM antibody fragment or anti-ADM non-Ig scaffold if the ratio is above a certain threshold, wherein the ADM-Gly/ ADM-NH$_2$ ratio is in a range between 1 and 10, preferably between 1.5 and 7.5, preferably between 2 and 5, most preferred the threshold is 2.5.

11. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-9, wherein the sample of bodily fluid of said patient is selected from the group of blood, serum, plasma, urine, cerebrospinal fluid (CSF), and saliva.

12. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiment 11, wherein said sample is selected from the group comprising human citrate plasma, heparin plasma and EDTA plasma.

13. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-12, wherein an immunoassay is used for determining the ratio of pro-Adrenomedullin or a fragment thereof and ADM-NH$_2$, wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34).

14. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiment 13, wherein said immunoassay is a sandwich immunoassay, preferably a fully automated assay.

15. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-14, wherein the assay sensitivity of said assay for the detection of ADM-NH$_2$ is able to quantify ADM-NH$_2$ of healthy subjects and is <70 pg/ml, preferably <40 pg/ml and more preferably <10 pg/ml.

16. Anti-adrenomedullin (ADM) antibody or an anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-14, wherein the assay sensitivity of said assay for ADM-Gly is able to quantify ADM-Gly of healthy subjects and is 20 pg/ml, preferably 15 pg/ml and more preferably 10 pg/ml.

17. Anti-adrenomedullin (ADM) antibody or anti-ADM antibody fragment or anti-ADM non-Ig scaffold for use in the treatment of a critically ill patient suffering from an acute disease or condition selected from the group comprising: severe infections (e.g., meningitis, systemic inflammatory response syndrome (SIRS), sepsis), shock (e.g., septic shock, cardiogenic shock), acute heart failure (including acute decompensated heart failure, chronic heart failure with worsening signs and symptoms), myocardial infarction, stroke, organ dysfunction (e.g., kidney, liver, heart, lung) or dementia in order to accelerate the conversion of ADM-Gly to ADM-NH$_2$ of circulating ADM-Gly in said patient according to embodiments 1-16, wherein the level of pro-Adrenomedullin or a fragment thereof and ADM-NH$_2$ (SEQ ID No. 20) is determined by using one binder to said pro-Adrenomedullin or a fragment thereof and a second binder to ADM-NH$_2$ (SEQ ID No. 20), wherein said proAdrenomedullin or a fragment thereof is selected from the group consisting of PAMP (SEQ ID No. 32), MR-proADM (SEQ ID No. 33), ADM-Gly (SEQ ID No. 21) and CT-proADM (SEQ ID No. 34), and wherein both binders are selected from the group comprising an antibody, an antibody fragment or a non-Ig-Scaffold binding to said pro-Adrenomedullin or a fragment thereof and ADM-NH$_2$.

18. Anti-ADM antibody or anti-ADM antibody fragment or anti-ADM non-Ig scaffold for use in therapy of a patient, wherein said anti-ADM antibody or anti-ADM fragment or anti-ADM non-Ig scaffold binds to the N-terminal and/or mid-regional part (amino acid 1-42) of ADM-Gly and/or ADM-NH$_2$: YRQSMNNFQGLRSFGCRFGTCTVQKLAHQIYQ FTDKDKDNVA (SEQ ID No. 23), wherein in a sample of bodily fluid of said patient the level of peptidylglycine alpha-amidating monooxygenase (PAM) and/or its isoforms and/or fragments thereof is determined and the patient is treated with said anti-ADM antibody or an anti-ADM antibody fragment or anti-ADM non-Ig scaffold, if the level of peptidylglycine alpha-amidating monooxygenase (PAM) is below a threshold.

19. Anti-ADM antibody or anti-ADM antibody fragment or anti-ADM non-Ig scaffold for use in therapy of a patient according to embodiment 19, wherein said level of PAM and/or its isoforms and/or fragments thereof is the total concentration of PAM and/or its isoforms and/or fragments thereof having at least 12 amino acids or the activity of PAM and/or its isoforms and/or fragments thereof comprising the sequences SEQ ID No. 39, SEQ ID No. 40, SEQ ID No. 41, SEQ ID No. 42, SEQ ID No. 43, SEQ ID No. 44, SEQ ID No. 45, SEQ ID No. 46 and SEQ ID No. 47.

20. Anti-ADM antibody or anti-ADM antibody fragment or anti-ADM non-Ig scaffold for use in therapy of a patient according to any of the embodiments 1-19, wherein the anti-adrenomedullin (ADM) antibody or an anti-adrenomedullin antibody fragment or anti-ADM non-Ig scaffold is used in combination with L-ascorbic acid.

21. Anti-Adrenomedullin (ADM) antibody or anti-ADM antibody fragment or anti-ADM non-Ig scaffold in combination with L-ascorbic acid, a. for use in therapy of an acute disease or acute condition of a patient for stabilizing the systemic circulation of said patient wherein said patient is in need of stabilizing the systemic circulation and exhibits a heart rate of >100 beats/min and/or <65 mm Hg mean arterial pressure and wherein stabilizing the systemic circulation means increasing the mean arterial pressure over 65 mmHg, or b. for use in the prevention of a heart rate increase to >100 beats/min and/or a mean arterial pressure decrease to <65 mm Hg in patients having an acute disease or acute condition, or c. for use in therapy of an acute disease or acute condition of a patient that suffers from a chronic and/or acute disease or acute condition for prevention or reduction of organ dysfunction or prevention of organ failure in said patient and wherein said organ is selected from the group comprising heart, kidney, liver, lungs, pancreas, small intestines and spleen, or d. for use in therapy or prevention of SIRS, meningitis, sepsis, shock, e.g., septic shock in a patient e. for the reduction of the mortality risk in a patient with SIRS, meningitis, sepsis, shock, e.g., septic shock, wherein said anti-ADM antibody or anti-ADM fragment or anti-ADM non-Ig scaffold binds to the N-terminal and/or mid-regional part (amino acid 1-42) of ADM-Gly and/or ADM-NH$_2$:

(SEQ ID No. 23)
YRQSMNNFQGLRSFGCRFGTCTVQKLAHQIYQFTDKDKDNVA.

22. Anti-Adrenomedullin (ADM) antibody or anti-ADM antibody fragment or anti-ADM non-Ig scaffold in combination with L-ascorbic acid according to embodiment 21, wherein said L-ascorbic acid is a single enantiomer, a mixture of enantiomers, a mixture of diastereomers or a pharmaceutically acceptable salt, solvate, hydrate or prodrug thereof.

FIGURE DESCRIPTION

FIG. 1a: Illustration of antibody formats—Fv and scFv-Variants

Figure 1C:
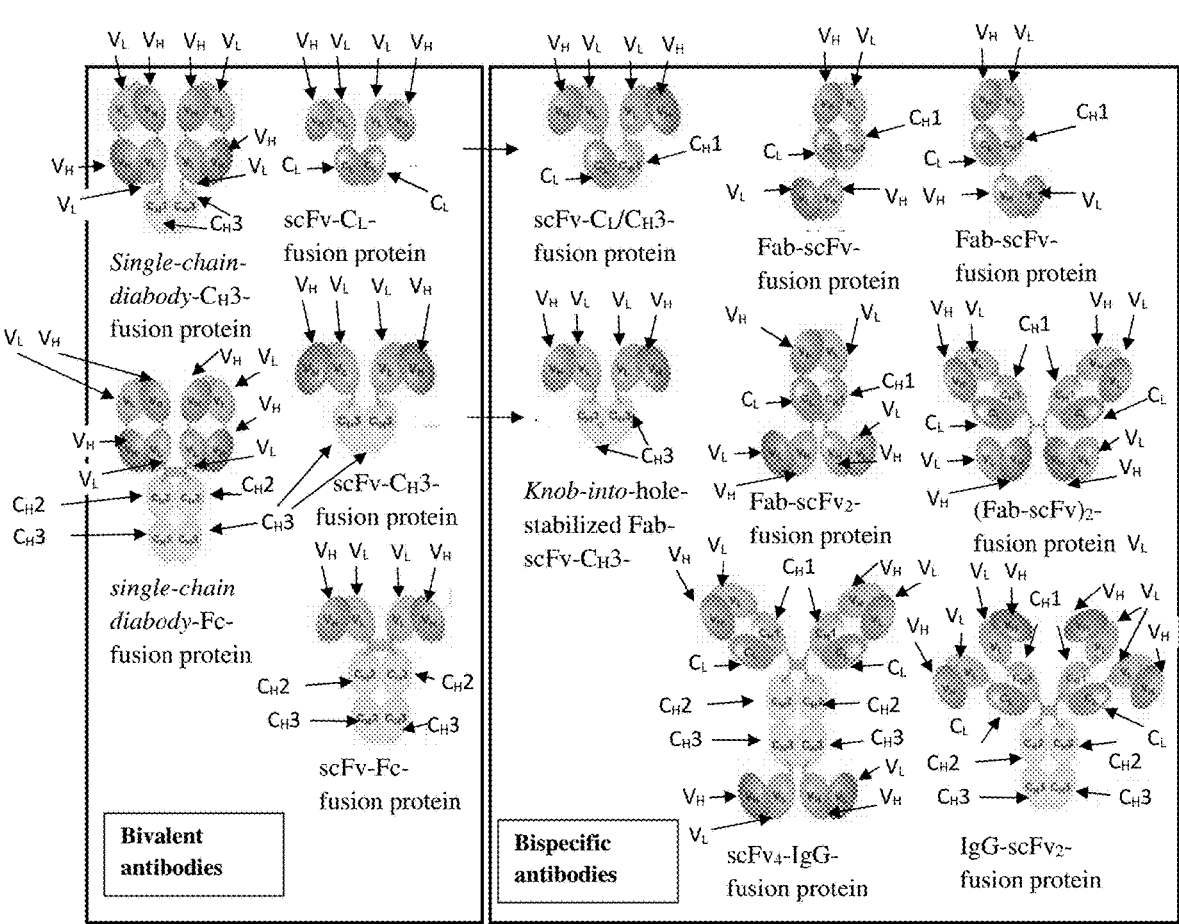

FIG. 1b: Illustration of antibody formats—heterologous fusions and bifunctional antibodies FIG. 1c: Illustration of antibody formats—bivalent antibodies and bispecific antibodies

FIG. 2:

a: Dose response curve of human ADM. Maximal cAMP stimulation was adjusted to 100% activation b: Dose/inhibition curve of human ADM 22-52 (ADM-receptor antagonist) in the presence of 5.63 nM hADM.

c: Dose/inhibition curve of CT-H in the presence of 5.63 nM hADM d: Dose/inhibition curve of MR-H in the presence of 5.63 nM hADM e: Dose/inhibition curve of NT-H in the presence of 5.63 nM hADM f: Dose response curve of mouse ADM. Maximal cAMP stimulation was adjusted to 100% activation g: Dose/inhibition curve of human ADM 22-52 (ADM-receptor antagonist) in the presence of 0.67 nM mADM h: Dose/inhibition curve of CT-M in the presence of 0.67 nM mADM i: Dose/inhibition curve of MR-M in the presence of 0.67 nM mADM j: Dose/inhibition curve of NT-M in the presence of 0.67 nM mADM k: Shows the inhibition of ADM by F(ab)$_2$ NT-M and by Fab NT-M l: shows the inhibition of ADM by F(ab)$_2$ NT-M and by Fab NT-M FIG. 3: This figure shows a typical hADM dose/signal curve. And an hADM dose signal curve in the presence of 100 µg/mL antibody NT-H.

Figure 4:

FIG. 4: This figure shows the stability of hADM in human plasma (citrate) in absence and in the presence of NT-H antibody.

FIG. 5: Alignment of the Fab with homologous human framework sequences.

Figure 6:
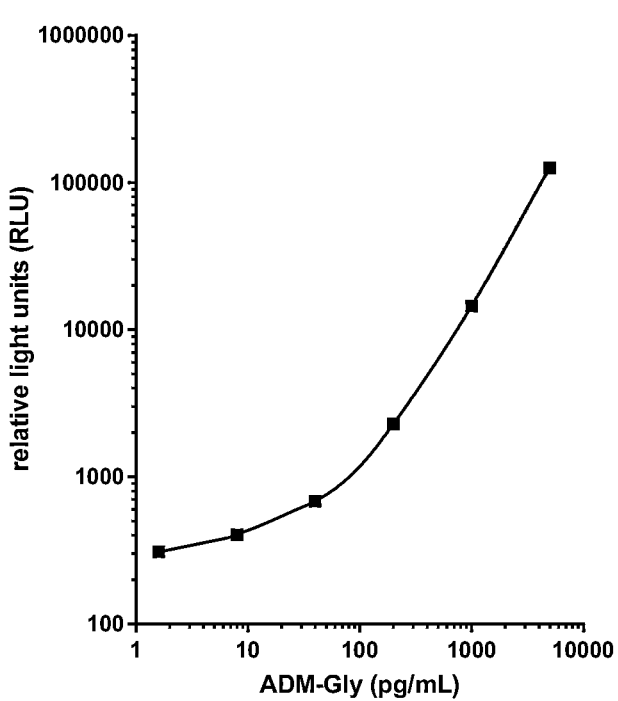

FIG. 6: This figure shows a typical ADM-Gly dose/signal curve.

Figure 7:
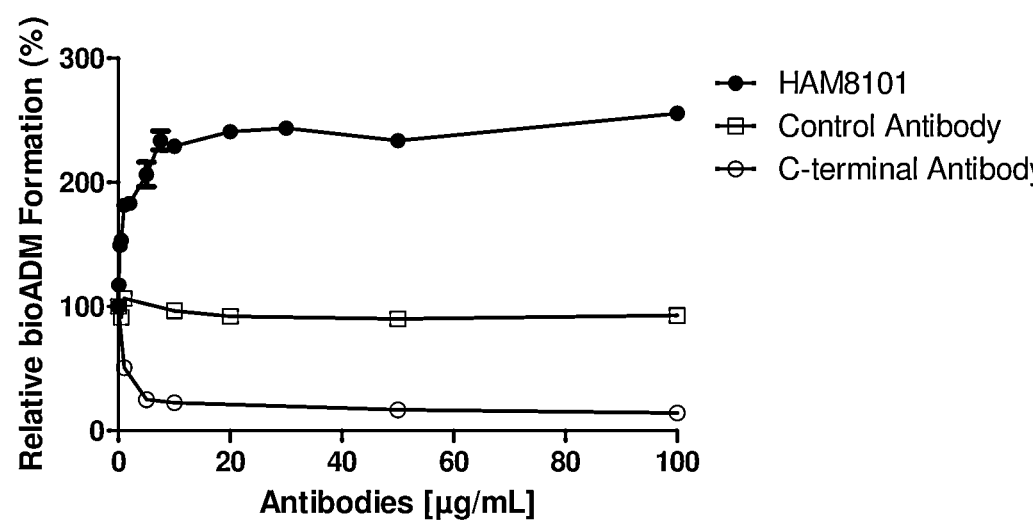

FIG. 7: Influence of HAM8101 on the formation of bio-ADM by human recombinant PAM. The change of the bio-ADM signal per minute (RLU/min) is expressed in %. The relative bio-ADM signal for the antibody concentration of 0 µg/mL was set as 100%.

Figure 8:
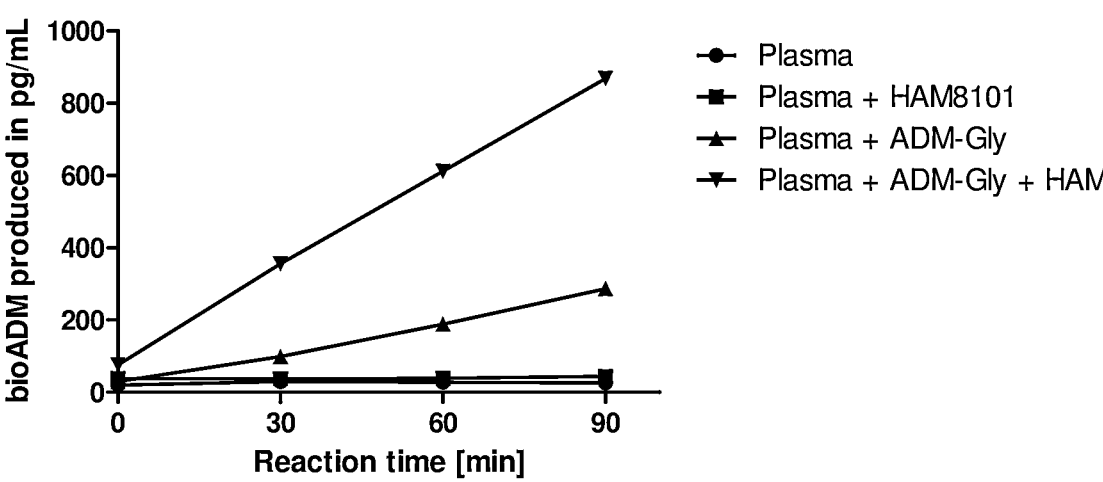

FIG. 8: Influence of HAM8101 on the formation of bio-ADM by human native PAM (with and without exogenous ADM-Gly as substrate).

Figure 9:
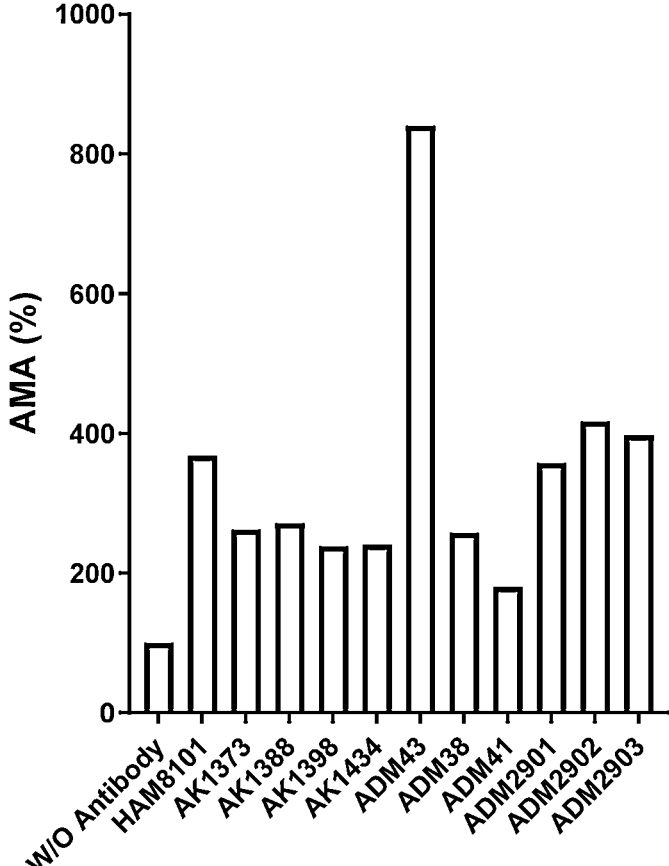

FIG. 9: Influence of NT- and MR-anti-ADM antibodies on native human adrenomedullin maturation activity (AMA).

Figure 10:
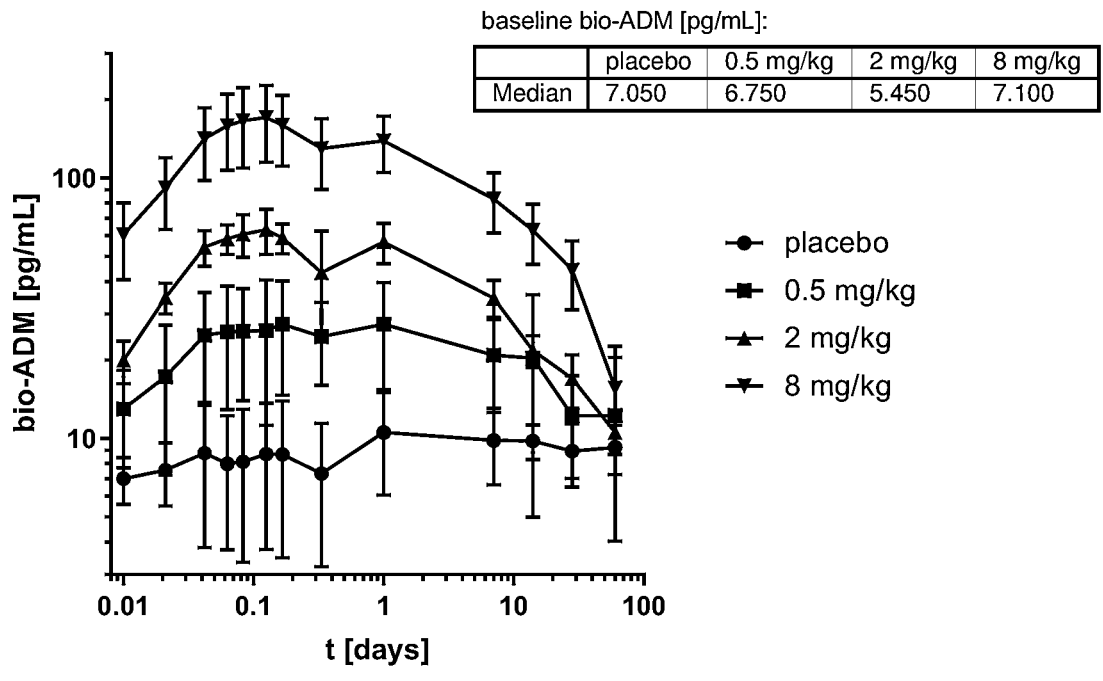

FIG. 10: ADM-concentration in healthy human subjects after NT-H application at different doses up to 60 days.

Figure 11:
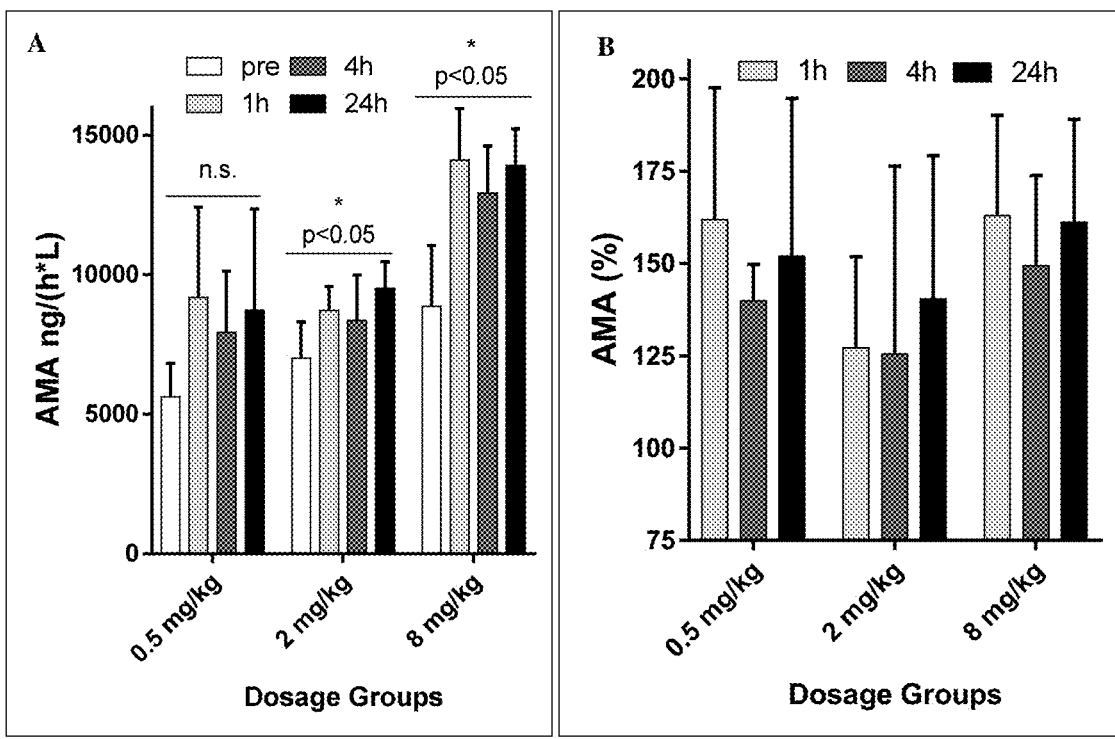

FIG. 11: ADM maturation activities (AMA) for subjects before and after administration of HAM8101 (average of activities from n=3 samples).

Figure 12:
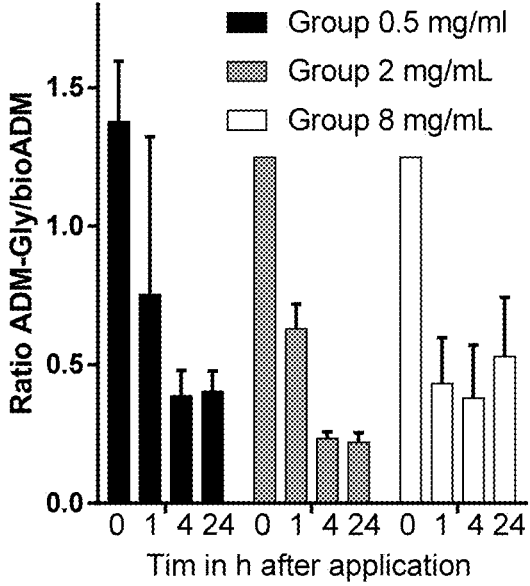

FIG. 12: Ratio ADM-Gly/bioADM in Phase1A clinical trial samples at different time-points (pre application and 1 h, 4 h, 24 h after application of HAM 8101).

Figure 13:
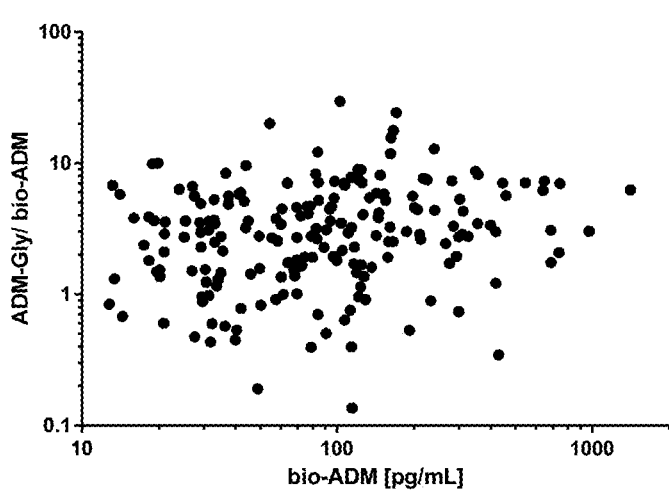

FIG. 13: Correlation between bio-ADM and ADM-Gly/bio-ADM ratio in sepsis and septic shock patients (AdrenOSS-1) (r=0.21, p=0.003).

Figure 14:
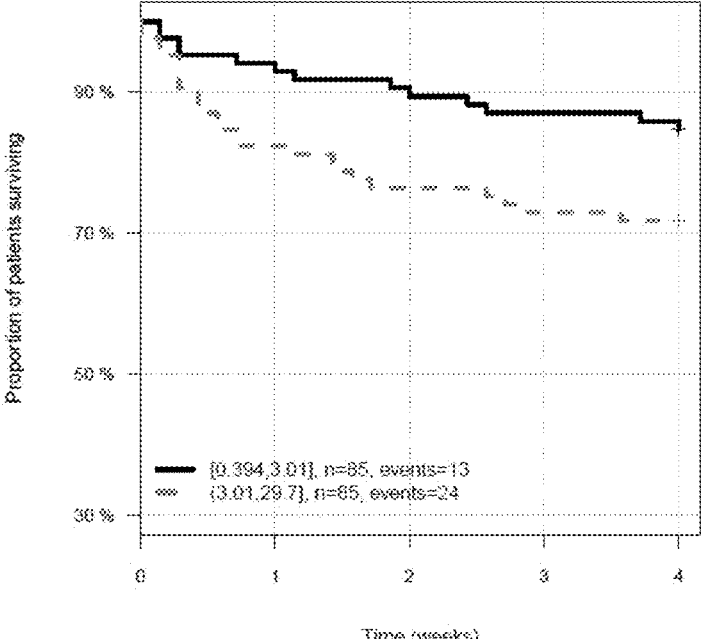

FIG. 14: Kaplan-Meier-Plot of ADM-Gly/bio-ADM ratio for sepsis and septic shock patients (AdrenOSS-1) for 28-day survival outcome.

Figure 15:
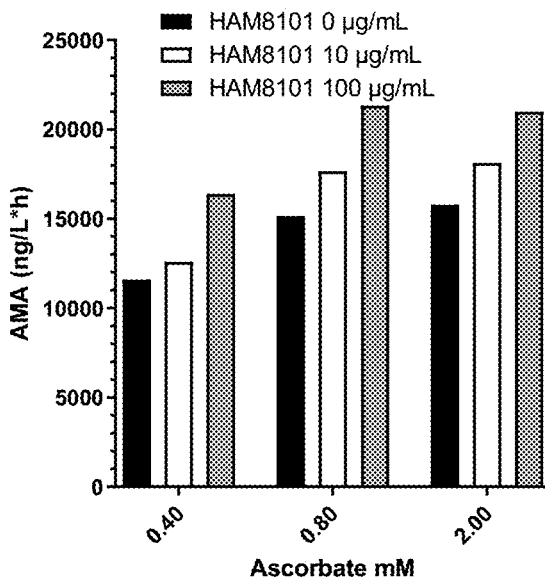

FIG. 15: ADM maturation activities (AMA) in plasma with HAM8101 and different concentrations of ascorbate.

EXAMPLES

It should be emphasized that the antibodies, antibody fragments and non-Ig scaffolds of the example portion in accordance with the invention are binding to ADM, and thus should be considered as anti-ADM antibodies/antibody fragments/non-Ig scaffolds.

Example 1—Generation of Antibodies and Determination of their Affinity Constants Several anti-human and anti-murine ADM antibodies were produced and their affinity constants were determined (see tables 1 and 2).

Peptides/Conjugates for Immunization:

Peptides for immunization were synthesized, see Table 1, (JPT Technologies, Berlin, Germany) with an additional N-terminal Cystein (if no Cystein is present within the selected ADM-sequence) residue for conjugation of the peptides to Bovine Serum Albumin (BSA). The peptides were covalently linked to BSA by using Sulfolink-coupling gel (Perbio-science, Bonn, Germany). The coupling procedure was performed according to the manual of Perbio.

Mouse Monoclonal Antibody Production:

A Balb/c mouse was immunized with 100 µg Peptide-BSA-Conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intra-venous injection. Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting, the selected cultures were cloned and re-cloned using the limiting-dilution technique and the isotypes were determined (see also Lane, R. D.

1985. *J. Immunol. Meth.* 81: 223-228; Ziegler et al. 1996. *Horm. Metab. Res.* 28: 11-15).

Antibodies were produced via standard antibody production methods (Marx et al, 1997. *Monoclonal Antibody Production, ATLA* 25, 121) and purified via Protein A. The antibody purities were >95% based on SDS gel electrophoresis analysis.

Human Antibody Production by Means of Phage Display:

The human naive antibody gene libraries HALT/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see also Hust et al. 2011. *Journal of Biotechnology* 152, 159-170; Schütte et al. 2009. *PLoS One* 4, e6625).

Positive clones have been selected based on positive ELISA signal for antigen and negative for streptavidin coated micro titer plates. For further characterizations the scFv open reading frame has been cloned into the expression plasmid pOPE107 (Hust et al., *J. Biotechn.* 2011), captured from the culture supernatant via immobilized metal ion affinity chromatography and purified by a size exclusion chromatography.

Affinity Constants:

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare). (Lorenz et al. 2011. *Antimicrob Agents Chemother.* 55(1): 165-173).

The monoclonal antibodies were raised against the below depicted ADM regions of human and murine ADM, respectively. The following table represents a selection of obtained antibodies used in further experiments. Selection was based on target region:

TABLE 1

| Sequence Number | Antigen/Immunogen | ADM Region | Designation | Affinity constants Kd (M) |
|---|---|---|---|---|
| SEQ ID: 14 | YRQSMNNFQGLRSFGCRFGTC | 1-21 | NT-H | $5.9 \times 10^{-9}$ |
| SEQ ID: 15 | CTVQKLAHQIYQ | 21-32 | MR-H | $2 \times 10^{-9}$ |
| SEQ ID: 16 | CAPRSKISPQGY-NH$_2$ | C-42-52 | CT-H | $1.1 \times 10^{-9}$ |
| SEQ ID: 17 | YRQSMNQGSRSNGCRFGTC | 1-19 | NT-M | $3.9 \times 10^{-9}$ |
| SEQ ID: 18 | CTFQKLAHQIYQ | 19-31 | MR-M | $4.5 \times 10^{-10}$ |
| SEQ ID: 19 | CAPRNKISPQGY-NH$_2$ | C-40-50 | CT-M | $9 \times 10^{-9}$ |
| SEQ ID: 49 | AHQIYQFTDKDKDC | 27-39-C | MR-CT-H | — |

The following is a list of further obtained monoclonal antibodies:

TABLE 2

| Target | Source | Clone number | Affinity (M) | Max. inhibition bioassay (%) (see example 2) |
|---|---|---|---|---|
| NT-M | Mouse | ADM/63 | $5.8 \times 10^{-9}$ | 45 |
| NT-M | Mouse | ADM/364 | $2.2 \times 10^{-8}$ | 48 |
| NT-M | Mouse | ADM/365 | $3.0 \times 10^{-8}$ | |
| NT-M | Mouse | ADM/366 | $1.7 \times 10^{-8}$ | |
| NT-M | Mouse | ADM/367 | $1.3 \times 10^{-8}$ | |
| NT-M | Mouse | ADM/368 | $1.9 \times 10^{-8}$ | |
| NT-M | Mouse | ADM/369 | $2.0 \times 10^{-8}$ | |
| NT-M | Mouse | ADM/370 | $1.6 \times 10^{-8}$ | |
| NT-M | Mouse | ADM/371 | $2.0 \times 10^{-8}$ | |
| NT-M | Mouse | ADM/372 | $2.5 \times 10^{-8}$ | |
| NT-M | Mouse | ADM/373 | $1.8 \times 10^{-8}$ | |
| NT-M | Mouse | ADM/377 | $1.5 \times 10^{-8}$ | |
| NT-M | Mouse | ADM/378 | $2.2 \times 10^{-8}$ | |
| NT-M | Mouse | ADM/379 | $1.6 \times 10^{-8}$ | |
| NT-M | Mouse | ADM/380 | $1.8 \times 10^{-8}$ | |
| NT-M | Mouse | ADM/381 | $2.4 \times 10^{-8}$ | |
| NT-M | Mouse | ADM/382 | $1.6 \times 10^{-8}$ | |
| NT-M | Mouse | ADM/383 | $1.8 \times 10^{-8}$ | |
| NT-M | Mouse | ADM/384 | $1.7 \times 10^{-8}$ | |
| NT-M | Mouse | ADM/385 | $1.7 \times 10^{-8}$ | |
| NT-M | Mouse | ADM/403 | $1.2 \times 10^{-8}$ | |
| NT-M | Mouse | ADM/395 | $1.2 \times 10^{-8}$ | |
| NT-M | Mouse | ADM/396 | $3.0 \times 10^{-8}$ | |
| NT-M | Mouse | ADM/397 | $1.5 \times 10^{-8}$ | |
| MR-M | Mouse | ADM/38 | $4.5 \times 10^{-10}$ | 68 |
| MR-M | Mouse | ADM/39 | $5.9 \times 10^{-9}$ | 72 |
| CT-M | Mouse | ADM/65 | $9.0 \times 10^{-9}$ | 100 |
| CT-M | Mouse | ADM/66 | $1.6 \times 10^{-8}$ | 100 |
| NT-H | Mouse | ADM/33 | $5.9 \times 10^{-8}$ | 38 |
| NT-H | Mouse | ADM/34 | $1.6 \times 10^{-8}$ | 22 |
| MR-H | Mouse | ADM/41 | $1.2 \times 10^{-8}$ | 67 |
| MR-H | Mouse | ADM/42 | $<1 \times 10^{-8}$ | |
| MR-H | Mouse | ADM/43 | $2.0 \times 10^{-9}$ | 73 |
| MR-H | Mouse | ADM/44 | $<1 \times 10^{-8}$ | |
| MR-CT-H | Mouse | ADM/2901 | | |
| MR-CT-H | Mouse | ADM/2902 | | |
| MR-CT-H | Mouse | ADM/2903 | | |
| CT-H | Mouse | ADM/15 | $<1 \times 10^{-8}$ | |
| CT-H | Mouse | ADM/16 | $1.1 \times 10^{-9}$ | 100 |
| CT-H | Mouse | ADM/17 | $3.7 \times 10^{-9}$ | 100 |
| CT-H | Mouse | ADM/18 | $<1 \times 10^{-8}$ | |
| hADM | Phage display | ADM/A7 | $<1 \times 10^{-8}$ | |
| hADM | Phage display | ADM/B7 | $<1 \times 10^{-8}$ | |
| hADM | Phage display | ADM/C7 | $<1 \times 10^{-8}$ | |
| hADM | Phage display | ADM/G3 | $<1 \times 10^{-8}$ | |
| hADM | Phage display | ADM/B6 | $<1 \times 10^{-8}$ | |
| hADM | Phage display | ADM/B11 | $<1 \times 10^{-8}$ | |
| hADM | Phage display | ADM/D8 | $<1 \times 10^{-8}$ | |
| hADM | Phage display | ADM/D11 | $<1 \times 10^{-8}$ | |
| hADM | Phage display | ADM/G12 | $<1 \times 10^{-8}$ | |

Generation of Antibody Fragments by Enzymatic Digestion:

The generation of Fab and $F(ab)_2$ fragments was done by enzymatic digestion of the murine full-length antibody NT-M. Antibody NT-M was digested using a) the pepsin-based $F(ab)_2$ Preparation Kit (Pierce 44988) and b) the papain-based Fab Preparation Kit (Pierce 44985). The fragmentation procedures were performed according to the instructions provided by the supplier. Digestion was carried out in case of $F(ab)_2$-fragmentation for 8 h at 37° C. The Fab-fragmentation digestion was carried out for 16 h, respectively.

Procedure for Fab Generation and Purification:

The immobilized papain was equilibrated by washing the resin with 0.5 ml of digestion buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample were added to the spin column tube containing the equilibrated immobilized Papain. Incubation time of the digestion reaction was done for 16 h on a tabletop rocker at 37° C. The column was centrifuged at 5000×g for 1 minute to separate digest from the immobilized Papain. Afterwards the resin was washed with 0.5 ml PBS and centrifuged at 5000×g for 1 minute. The wash fraction was added to the digested antibody that the total sample volume was 1.0 ml. The NAb Protein A Column was equilibrated with PBS and IgG elution buffer at room temperature. The column was centrifuged for 1 minute to remove storage solution (contains 0.02% sodium azide) and equilibrated by adding 2 ml of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments. (References: Coulter and Harris 1983. *J. Immunol. Meth.* 59, 199-203.; Lindner et al. 2010. *Cancer Res.* 70, 277-87; Kaufmann et al. 2010. *PNAS.* 107, 18950-5.; Chen et al. 2010. *PNAS.* 107, 14727-32; Uysal et al. 2009 *J. Exp. Med.* 206, 449-62; Thomas et al. 2009. *J. Exp. Med.* 206, 1913-27; Kong et al. 2009 *J. Cell Biol.* 185, 1275-840).

Procedure for Generation and Purification of $F(Ab')_2$ Fragments:

The immobilized Pepsin was equilibrated by washing the resin with 0.5 ml of digestion buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample where added to the spin column tube containing the equilibrated immobilized Pepsin. Incubation time of the digestion reaction was done for 16 h on a tabletop rocker at 37° C. The column was centrifuged at 5000×g for 1 minute to separate digest from the immobilized Papain. Afterwards the resin was washed with 0.5 mL PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 mL of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments. (References: Mariani et al. 1991. *Mol. Immunol.* 28: 69-77; Beale 1987. *Exp Comp Immunol* 11: 287-96; Ellerson et al. 1972. *FEBS Letters* 24(3): 318-22; Kerbel and Elliot 1983. *Meth Enzymol* 93: 113-147; Kulkarni et al. 1985. *Cancer Immunol Immunotherapy* 19:211-4; Lamoyi 1986. *Meth Enzymol* 121: 652-663; Parham et al. 1982. *J Immunol Meth* 53: 133-73; Raychaudhuri et al. 1985. *Mol Immunol* 22(9): 1009-19; Rousseaux et al. 1980. *Mol Immunol* 17: 469-82; Rousseaux et al. 1983. *J Immunol Meth* 64: 141-6; Wilson et al. 1991. *J Immunol Meth* 138: 111-9).

NT-H-Antibody Fragment Humanization:

The antibody fragment was humanized by the CDR-grafting method (Jones et al. 1986. *Nature* 321, 522-525). The following steps were done to achieve the humanized sequence: Total RNA was extracted from NT-H hybridomas using the Qiagen kit. For first-round RT-PCR the QIAGEN®

OneStep RT-PCR Kit (Cat No. 210210) was used. RT-PCR was performed with primer sets specific for the heavy and light chains. For each RNA sample, 12 individual heavy chain and 11 light chain RT-PCR reactions were set up using degenerate forward primer mixtures covering the leader sequences of variable regions. Reverse primers are located in the constant regions of heavy and light chains. No restriction sites were engineered into the primers. The reaction set up was as follows: 5×QIAGEN® OneStep RT-PCR Buffer 5.0 μl, dNTP Mix (containing 10 mM of each dNTP) 0.8 μl, Primer set 0.5 μl, QIAGEN® OneStep RT-PCR Enzyme Mix 0.8 μl, Template RNA 2.0 μl, RNase-free water to 20.0 μl, Total volume 20.0 μl PCR condition: Reverse transcription: 50° C., 30 min; Initial PCR activation: 95° C., 15 min Cycling: 20 cycles of 94° C., 25 sec; 54° C., 30 sec; 72° C., 30 sec; Final extension: 72° C., 10 min Second-round semi-nested PCR: The RT-PCR products from the first-round reactions were further amplified in the second-round PCR. 12 individual heavy chain and 11 light chain RT-PCR reactions were set up using semi-nested primer sets specific for antibody variable regions.

The reaction setup was as follows: 2×PCR mix 10 μl; Primer set 2 μl; First-round PCR product 8 μl; Total volume 20 μl; Hybridoma Antibody Cloning Report PCR condition: Initial denaturing of 5 min at 95° C.; 25 cycles of 95° C. for 25 sec, 57° C. for 30 sec, 68° C. for 30 sec; Final extension is 10 min 68° C.

After PCR is finished, run PCR reaction samples onto agarose gel to visualize DNA fragments amplified. After sequencing more than 15 cloned DNA fragments amplified by nested RT-PCR, several mouse antibody heavy and light chains have been cloned and appear correct. Protein sequence alignment and CDR analysis identifies one heavy chain and one light chain. After alignment with homologous human framework sequences, the resulting humanized sequence for the variable heavy chain is the following: see FIG. 5. As the amino acids on positions 26, and 55 in the variable heavy chain and amino acid on position 40 in the variable light are critical to the binding properties, they may be reverted to the murine original. The resulting candidates are depicted below. (Padlan 1991. *Mol. Immunol.* 28: 489-498; Harris and Bajorath 1995. *Protein Sci.* 4: 306-310).

Annotation for the antibody fragment sequences (SEQ ID No.: 7-13, 35 and 36): bold and underline are the CDR 1, 2, 3 chronologically arranged.

```
(AM-VH-C)
                                   SEQ ID No.: 6
QVQLQQSGAELMKPGASVKISCKATGYTFSRYWIEWVKQRPGHGLEWIG

EILPGSGSTNYNEKFKGKATITADTSSNTAYMQLSSLTSEDSAVYYCTE

GYEYDGFDYWGQGTTLTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VH1)
                                   SEQ ID No.: 7
QVQLVQSGAEVKKPGSSVKVSCKASGYTFSRYWISWVRQAPGQGLEWMG

RILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK
```

```
(AM-VH2-E40)
                                   SEQ ID No.: 8
QVQLVQSGAEVKKPGSSVKVSCKASGYTFSRYWIEWVRQAPGQGLEWMG

RILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VH3-T26-E55)
                                   SEQ ID No.: 9
QVQLVQSGAEVKKPGSSVKVSCKATGYTFSRYWISWVRQAPGQGLEWMG

EILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VH4-T26-E40-E55)
                                   SEQ ID No.: 10
QVQLVQSGAEVKKPGSSVKVSCKATGYTFSRYWIEWVRQAPGQGLEWMG

EILPGSGSTNYAQKFQGRVTITADESTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPK (AM-VL-C)
                                   SEQ ID No.: 11
DVLLSQTPLSLPVSLGDQATISCRSSQSIVYSNGNTYLEWYLQKPGQSP

KLLIYRVSNRFSGVPDRFSGSGSGTDFTLKISRVEAEDLGVYYCFQGSH

IPYTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC (AM-VL1)
                                   SEQ ID No.: 12
DVVMTQSPLSLPVTLGQPASISCRSSQSIVYSNGNTYLNWFQQRPGQSP

RRLIYRVSNRDSGVPDRFSGSGSGTDFTLKISRVEAEDVGVYYCFQGSH

IPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC (AM-VL2-E40)
                                   SEQ ID No.: 13
DVVMTQSPLSLPVTLGQPASISCRSSQSIVYSNGNTYLEWFQQRPGQSP

RRLIYRVSNRDSGVPDRFSGSGSGTDFTLKISRVEAEDVGVYYCFQGSH

IPYTFGQGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

SEQ ID No.: 35
QVQLVQSGAEVKKPGSSVKVSCKASGYTFSRYWIEWVRQAPGQGLEWIG

EILPGSGSTNYNQKFQGRVTITADTSTSTAYMELSSLRSEDTAVYYCTE

GYEYDGFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT
```

-continued

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK

SEQ ID No.: 36

DVVLTQSPLSLPVTLGQPASISCRSSQSIVYSNGNTYLEWYLQRPGQSP

RLLIYRVSNRFSGVPDRFSGSGSGTDFTLKISRVEAEDVGVYYCFQGSH

IPYTFGGGTKLEIKRTVAAPSVFIFPPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

Example 2—Effect of Selected Anti-ADM-Antibodies on Anti-ADM-Bioactivity

Figure 2:
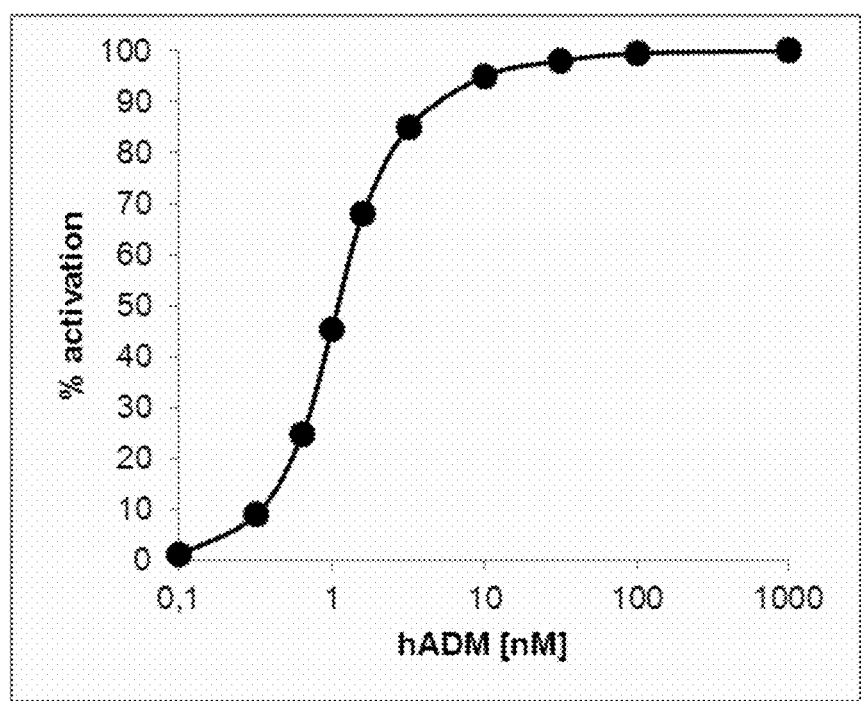
Figure 2:
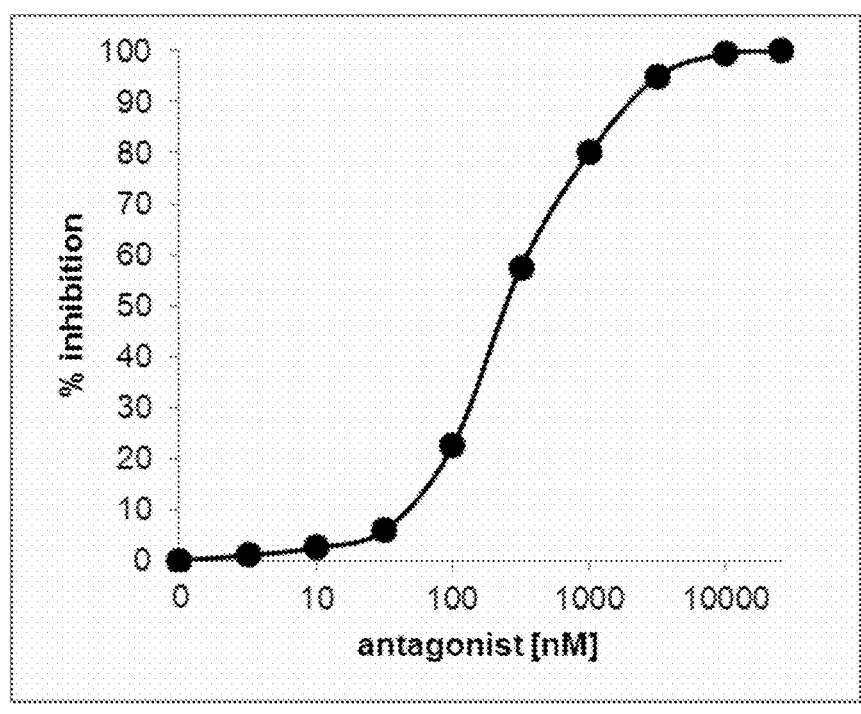
Figure 2:
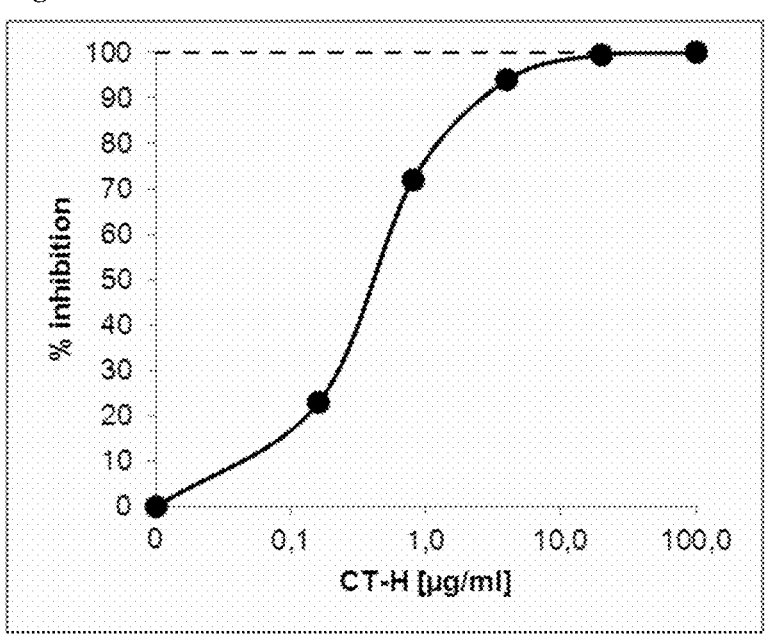
Figure 2:
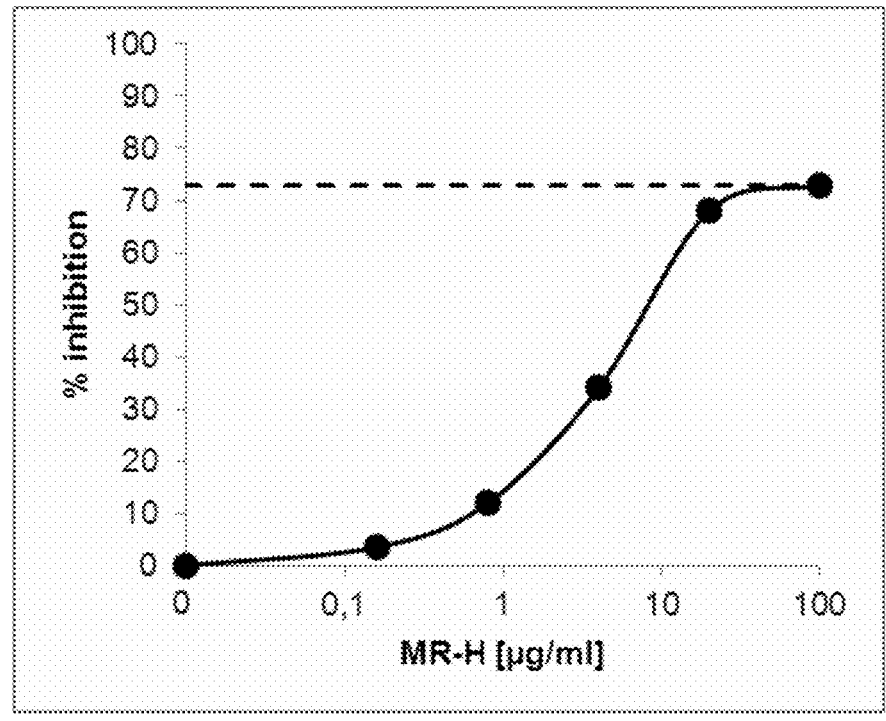
Figure 2:
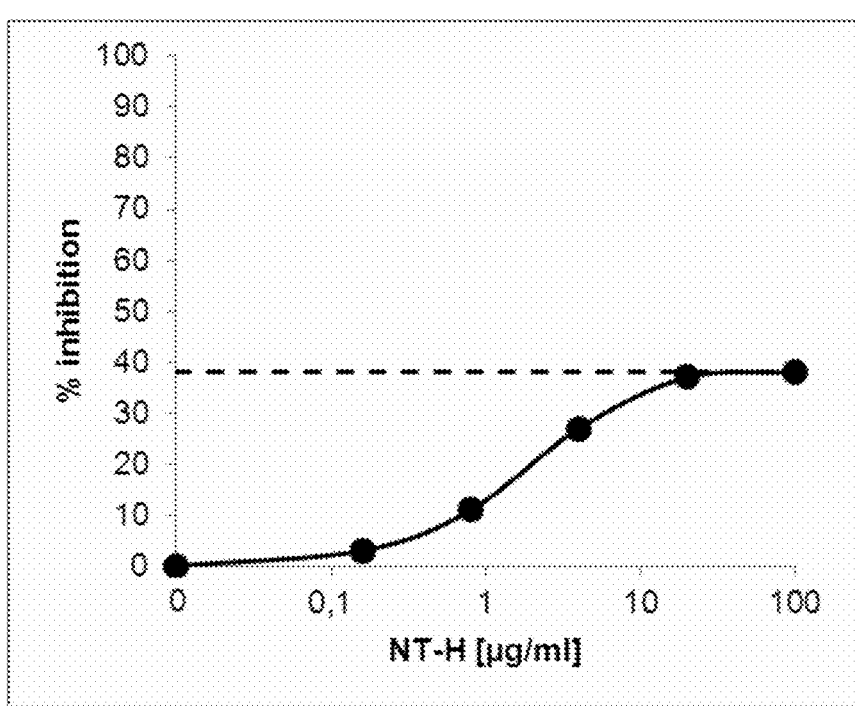
Figure 2:
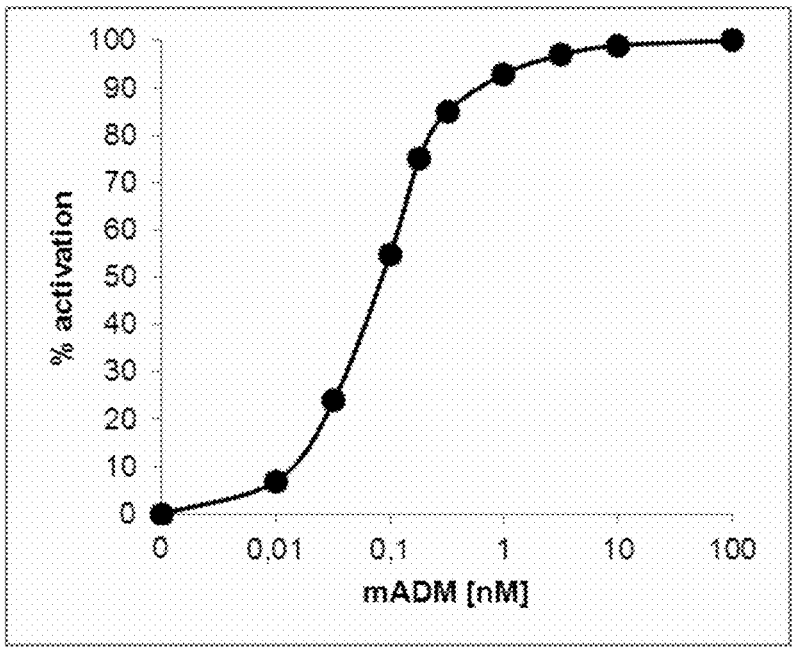
Figure 2:
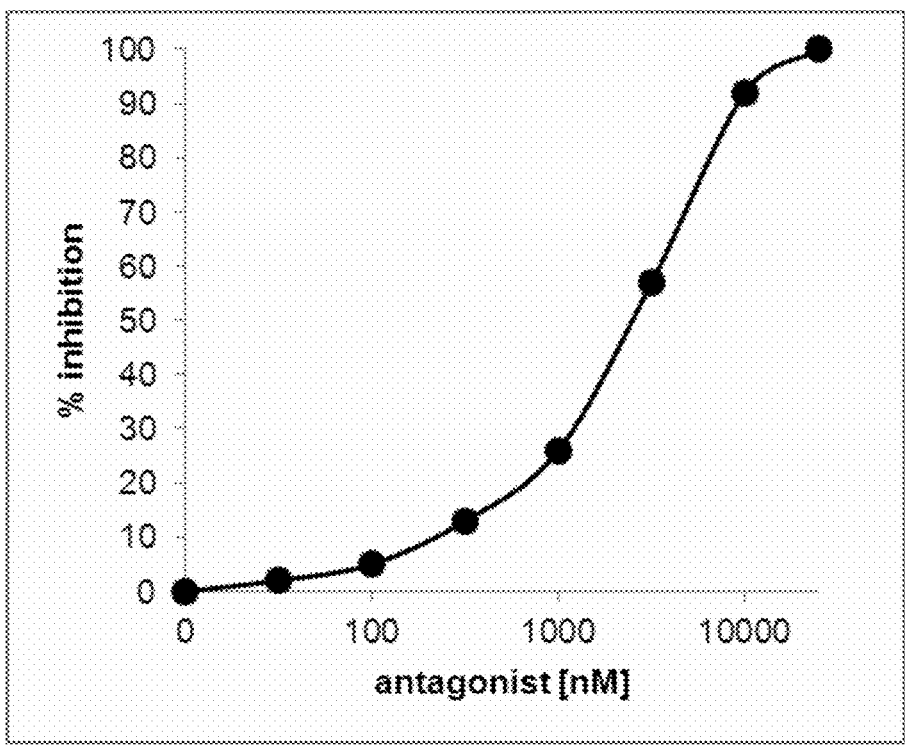
Figure 2:
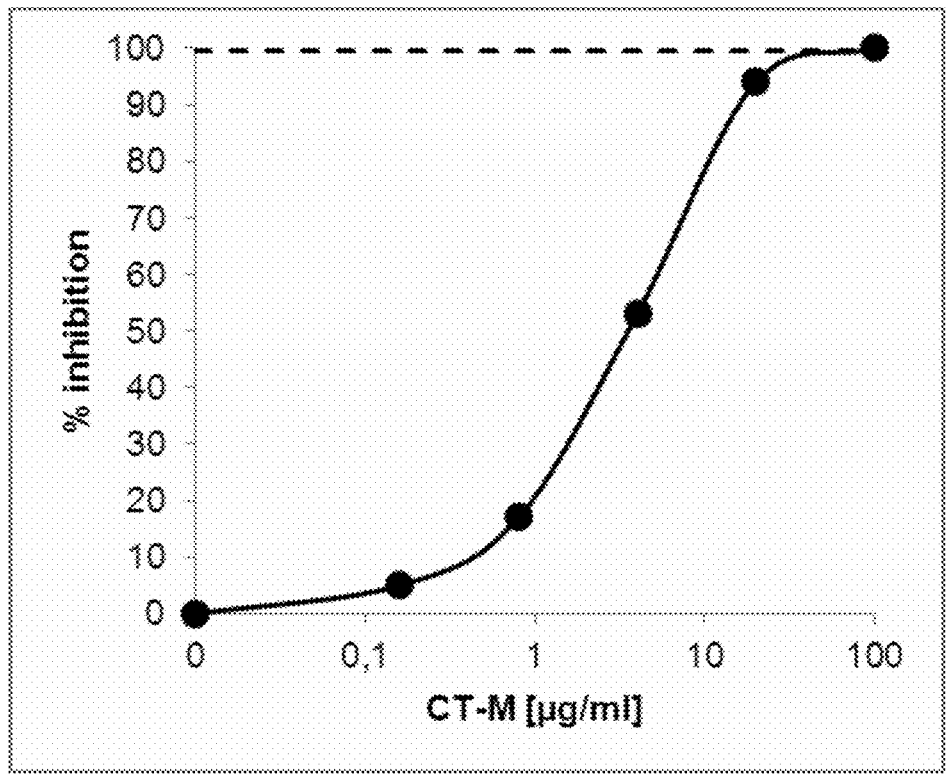
Figure 2:
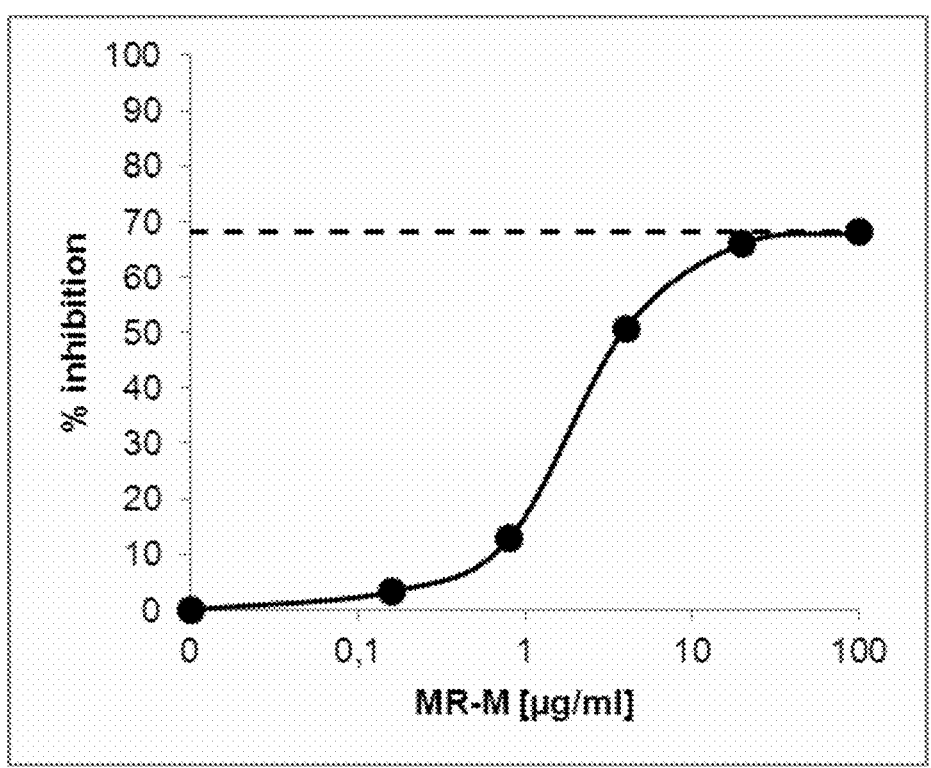
Figure 2:
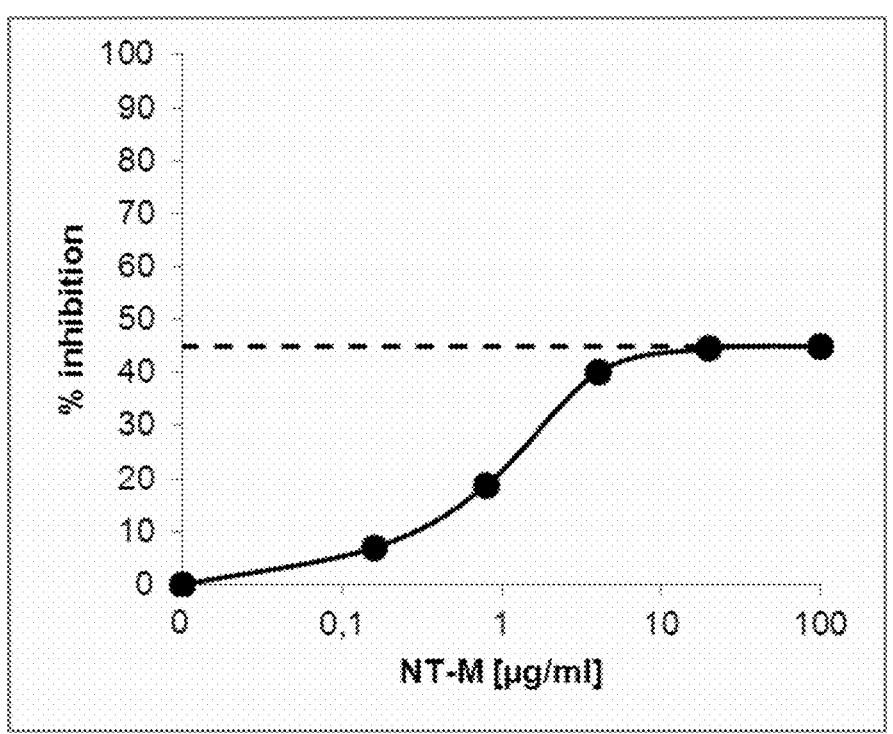
Figure 2:
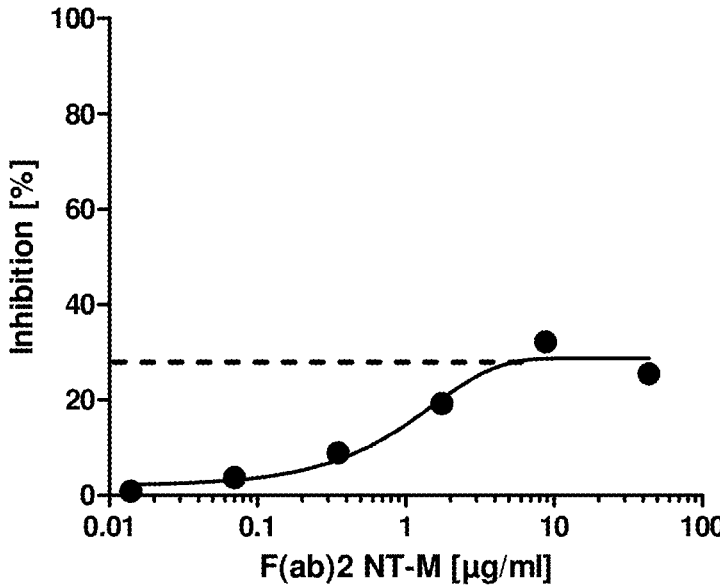
Figure 2:
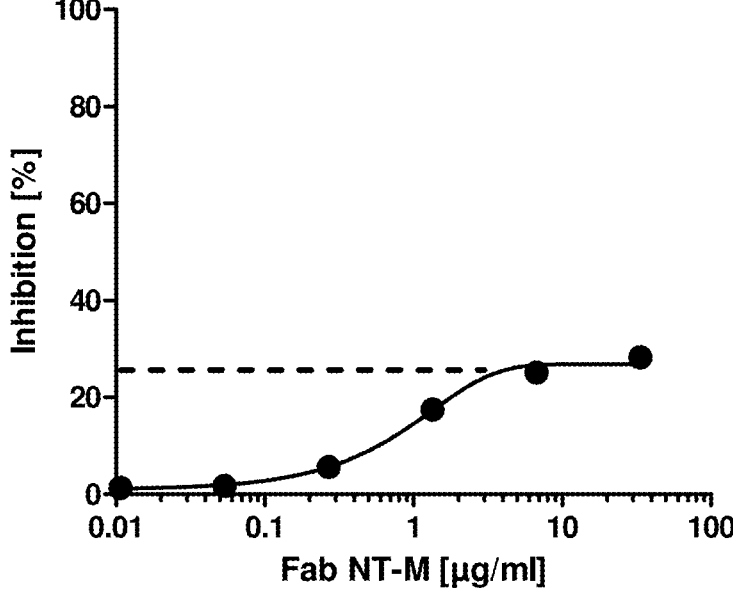

The effect of selected ADM-antibodies on ADM-bioactivity was tested in a human recombinant Adrenomedullin receptor cAMP functional assay (Adrenomedullin Bioassay). The following materials were used: Cell line CHO-K1, Adrenomedullin receptor (CRLR+RAMP3), Receptor Accession Number Cell line (CRLR: U17473; RAMP3: AJ001016). CHO-K1 cells expressing human recombinant adrenomedullin receptor (FAST-027C) grown prior to the test in media without antibiotic were detached by gentle flushing with PBS-EDTA (5 mM EDTA), recovered by centrifugation and resuspended in assay buffer (KRH: 5 mM KCl, 1.25 mM MgSO$_4$, 124 mM NaCl, 25 mM HEPES, 13.3 mM Glucose, 1.25 mM KH$_2$PO$_4$, 1.45 mM CaCl$_2$, 0.5 g/l BSA). Dose response curves were performed in parallel with the reference agonists (hADM or mADM).
Antagonist Test (96 Well):

For antagonist testing, 6 µl of the reference agonist (human (5.63 nM) or mouse (0.67 nM) adrenomedullin) was mixed with 6 µl of the test samples at different antagonist dilutions; or with 6 µl buffer. After incubation for 60 min at room temperature, 12 µl of cells (2,500 cells/well) were added. The plates were incubated for 30 min at room temperature. After addition of the lysis buffer, percentage of DeltaF will be estimated, according to the manufacturer specification, with the HTRF kit from Cis-Bio International (cat no 62AM2 PEB) hADM 22-52 was used as reference antagonist.
Antibodies Testing cAMP-HTRF Assay:

The anti-h-ADM antibodies (NT-H, MR-H, CT-H) were tested for antagonist activity in human recombinant adrenomedullin receptor (FAST-027C) cAMP functional assay in the presence of 5.63 nM Human ADM 1-52 (SEQ ID No. 20), at the following final antibody concentrations: 100 µg/ml, 20 µg/ml, 4 µg/ml, 0.8 µg/ml, 0.16 µg/ml. The anti-m-ADM antibodies (NT-M, MR-M, CT-M) were tested for antagonist activity in human recombinant adrenomedullin receptor (FAST-027C) cAMP functional assay in the presence of 0.67 nM Mouse ADM 1-50 (SEQ ID No. 22), at the following final antibody concentrations: 100 µg/ml, 20 µg/ml, 4 µg/ml, 0.8 µg/ml, 0.16 µg/ml. Data were plotted relative inhibition vs. antagonist concentration (see FIGS. 2 *a* to 2 *l*). The maximal inhibition by the individual antibody is given in table 3.

TABLE 3

| Maximal inhibition of ADM-antibodies | |
| --- | --- |
| Antibody | Maximal inhibition of ADM bioactivity (ADM-Bioassay) (%) |
| NT-H | 38 |
| MR-H | 73 |
| CT-H | 100 |
| NT-M FAB | 26 |
| NT-M FAB2 | 28 |
| NT-M | 45 |
| MR-M | 66 |
| CT-M | 100 |
| Non specific mouse IgG | 0 |

Example 3—Stabilization of hADM by the Anti-ADM Antibody

The stabilizing effect of human ADM by human ADM antibodies was tested using a hADM immunoassay. The technology used was a sandwich coated tube luminescence immunoassay, based on Acridinium ester labelling.

Labelled compound (tracer): 100 µg (100 µl) CT-H (1 mg/ml in PBS, pH 7.4, AdrenoMed AG Germany) was mixed with 10 µl Acridinium NHS-ester (1 mg/ml in acetonitrile, InVent GmbH, Germany) (EP 0353971) and incubated for 20 min at room temperature. Labelled CT-H was purified by Gel-filtration HPLC on Bio-Sil® SEC 400-5 (Bio-Rad Laboratories, Inc., USA) The purified CT-H was diluted in (300 mmol/L potassium phosphate, 100 mmol/L NaCl, 10 mmol/L Na-EDTA, 5 g/L Bovine Serum Albumin, pH 7.0). The final concentration was approx. 800.000 relative light units (RLU) of labelled compound (approx. 20 ng labeled antibody) per 200 µL. Acridiniumester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with MR-H (AdrenoMed AG, Germany) (1.5 µg MR-H/0.3 mL 100 mmol/L NaCl, 50 mmol/L TRIS/HCl, pH 7.8). After blocking with 5% bovine serum albumin, the tubes were washed with PBS, pH 7.4 and vacuum dried.

Figure 3:
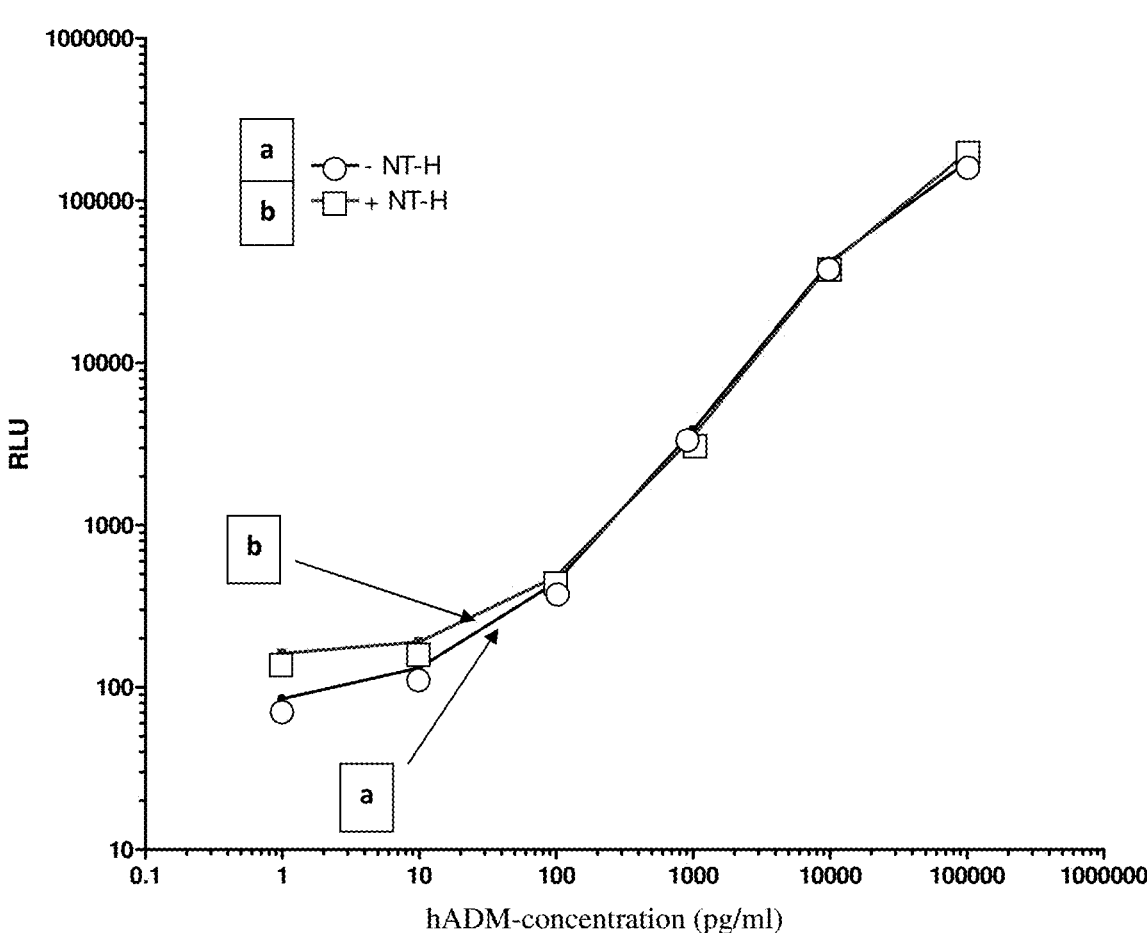

Calibration: The assay was calibrated, using dilutions of hADM (BACHEM AG, Switzerland) in 250 mmol/L NaCl, 2 g/L Triton X-100, 50 g/L Bovine Serum Albumin, 20 tabs/L Protease Inhibitor Cocktail (Roche Diagnostics AG, Switzerland).

hADM Immunoassay: 50 µl of sample (or calibrator) was pipetted into coated tubes, after adding labeled CT-H (200 µl), the tubes were incubated for 4 h at 4° C. Unbound tracer was removed by washing 5 times (each 1 ml) with washing solution (20 mM PBS, pH 7.4, 0.1% Triton X-100). Tube-bound chemiluminescence was measured by using the LB 953 (Berthold, Germany). FIG. 3 shows a typical hADM dose/signal curve. And an hADM dose signal curve in the presence of 100 µg/mL antibody NT-H. NT-H did not affect the described hADM immunoassay.

Stability of human Adrenomedullin: Human ADM was diluted in human Citrate plasma (final concentration 10 nM) and incubated at 24° C. At selected time points, the degradation of hADM was stopped by freezing at −20° C. The incubation was performed in absence and presence of NT-H (100 µg/ml). The remaining hADM was quantified by using the hADM immunoassay described above. FIG. 4 shows the stability of hADM in human plasma (citrate) in absence and in the presence of NT-H antibody. The half-life of hADM alone was 7.8 h and in the presence of NT-H, the half-life was 18.3 h. (2.3 times higher stability).

Example 4—Immunoassay for the Detection of ADM-Gly

ADM-Gly was quantified as based on Weber et al. (Weber et al. 2017. *JALM* 2(2): 222-233) for bioactive ADM with the following modifications: the tracer-antibody used for ADM-Gly detection, labelled with MACN-acridinium-NHS, was directed to the C-terminal glycine of ADM-Gly. The assay was calibrated with synthetic ADM-Gly. The limit of detection (LOD) was 10 pg/mL of ADM-Gly. Cross-reactivity of antibody directed to the C-terminal glycine of ADM with bio-ADM was in the range between 6 and 50% in a concentration dependent manner. All determined ADM-Gly concentrations were corrected for cross-reactivity as follows: For each ADM-Gly quantification additional quantification of bio-ADM in corresponding samples was performed using the Sphingotest® bio-ADM immunoassay. The corresponding bio-ADM values were used to determine the signal (RLU) generated with the antibody directed to C-terminal glycine of ADM on a bio-ADM calibration curve. The determined signal (RLU) was used to calculate the false-positive ADM-Gly concentration (pg/mL) using the ADM-Gly calibration curve. This concentration was subtracted from the initially determined ADM-Gly concentration. A typical standard curve is shown in FIG. 6.

Example 5—(In Vitro) Effect of NT- and MR-ADM-Antibodies on ADM-Gly to Bio-ADM Conversion a) Recombinant Human PAM The formation of bio-ADM from c-terminally glycinated 1-53 Adrenomedullin (ADM-Gly) by recombinant human PAM and the influence of the N-terminal anti-Adrenomedullin antibodies on the bio-ADM formation from ADM-Gly by PAM was investigated.

In a first step, 200 µl per well ADM-Gly (50 ng/mL) dissolved in buffer (300 mM potassium-phosphate, 100 mM NaCl, 10 mM Na-EDTA, 5 g/L BSA, pH 7.0) was added to microtiter plate wells that were precoated with an anti-MR-ADM antibody, and were incubated for 1 h at 22° C. under agitation (600 rpm). Unbound material was removed by washing. In a second step, varying concentrations (0-100 µg/mL) of either N-terminal- (HAM8101), C-terminal anti-Adrenomedullin antibody specifically blocking the glycinated C-terminus of ADM-Gly or an unspecific antibody (control antibody) was added to the wells (200 µl per well) for 1 h at 22° C. under agitation (600 rpm). The respective antibodies were diluted in buffer as described above. Unbound antibodies were removed by washing. Amidation reaction was initiated by addition of PAM reaction buffer (100 mM Tris-HCl, 5 µM CuSO$_4$, 2 mM L-Ascorbate, 50 µM amastatin and 200 µM leupeptin) containing 50 µg/mL of recombinant human PAM-containing protein solution (InVivo Biotech Services GmbH, Hennigsdorf). The amidation reaction was performed at 37° C. and was stopped by addition of EDTA (10 mM final concentration) at 0 minutes (t=0) and after 40 minutes (t=40). The plates were washed again and labelled anti-ADM antibody specific to the amidated C-Terminus of ADM) was added as tracer and incubated for 1 hour at 22° C. and 600 rpm. After a final washing step, the remaining chemiluminescence was measured for 1 s per well with a Centro LB 960 microtiter plate luminescence reader (Berthold Technologies). To evaluate the velocity of the enzyme PAM, the signal for bio-ADM measured at t=0 minutes was subtracted from the signal for bio-ADM at t=40 minutes for each antibody concentration. The signal (t40–t0) for each antibody-concentration was normalized to the signal (t40–t0) without antibody addition, which was set at 100%.

As shown in FIG. 7, the control antibody, having no specificity to Adrenomedullin, showed no influence on the activity of the PAM enzyme. The C-terminal anti-Adrenomedullin antibody specifically recognizing ADM-Gly inhibits the reaction of the PAM enzyme in a concentration-dependent manner, as it blocks the C-terminal glycine residue that represents the substrate for the PAM enzyme. Surprisingly, the N-terminal anti-ADM-antibody (HAM8101) has a significant accelerating effect on the conversion of ADM-Gly to bio-ADM catalyzed by PAM in a concentration dependent manner. The PAM-accelerating effect of HAM8101 was detected for concentrations up to 10 µg/mL. Concentrations of more than 10 µg/mL did not further increase the PAM activity. The PAM activity at a concentration of 10 µg/mL of HAM8101 was 233% when compared to the reaction without antibody addition.

b) Native Human PAM

In a further experiment we investigated the formation of bio-ADM from ADM-Gly by native human plasma PAM and the influence of N-terminal- and mid-regional anti-adrenomedullin antibodies.

For the testing of N-terminal anti-ADM antibody HAM8101 the experiment was set up as follows:

Human Li-Heparin plasma (pool of 3 specimen) was used as source of human native PAM. The amidation reaction was performed in a total volume of 120 µl at 37° C. 96 µl of plasma were spiked with either HAM8101 (375 µg/mL final concentration) or ADM-Gly (5 ng/mL final concentration) or with both. As control, equal volumes of 100 mM Tris-HCl, pH 7.5 were added to untreated plasma. The prepared samples were allowed to chill for 15 minutes at room temperature. The amidation reaction was started by addition of 24 µl of PAM-reaction buffer resulting in final concentrations of 2 mM L-Ascorbate and 5 µM CuSO4, respectively. The final concentrations of HAM8101 and ADM-Gly were 300 µg/mL and 4 ng/mL, respectively. The reaction was allowed to proceed for 90 minutes at 37° C. After 0 min, 30 min, 60 min and 90 min of incubation, the reaction was stopped by addition of 20 mM EDTA (final concentration). The concentration of bio-ADM in the reaction sample was quantified using the Sphingotest® bio-ADM immunoassay as described recently (Weber et al. 2017. *JALM* 2(2): 222-233).

For testing of mid-regional anti-ADM antibody in comparison to HAM8101 and four additional N-terminal anti-ADM antibodies the experiment was set-up as follows:

Human serum was used as source of human native PAM. Each sample (20 µl) was diluted two-fold in 100 mM Tris-HCl in duplicate. The amidation reaction was initiated by addition of 160 µl of NT-ADM antibodies (HAM8101, AK1373, AK1388, AK1398 or AK1434) or MR-ADM antibodies (ADM43, ADM38, ADM41, ADM2901, ADM2902 and ADM2903) containing PAM-reaction buffer (100 mM Tris-HCl, pH 7.5, 6.25 µM CuSO$_4$, 2.5 mM Ascorbate, 125 µg/mL Catalase, 62.5 µM Amastatin, 250 µM Leupeptin, and 36 ng/mL synthetic 1-53 Adrenomedullin-Gly as substrate). The final antibody concentrations were 100 µg/mL, respectively. Afterwards, 100 µl of each individual reaction of duplicated samples were combined and transferred into 20 µl of 200 mM EDTA to terminate the amidation reaction and thus to generate a t=0 minutes reaction time-point followed by incubation at 37° C. for 40 minutes. Afterwards the non-terminated reactions were stopped with 10 μl of 200 mM EDTA. To determine the PAM activity in NT-ADM antibody containing samples, bio-ADM was quantified in each reaction using the Sphingotest® bio-ADM immunoassay (Weber et al. 2017, supra). The MR-ADM antibody containing reaction was transferred to an alternative bio-ADM assay (description below). A control reaction without antibodies was measured in both bio-ADM assays. For each sample the difference between t=40 min and t=0 min bio-ADM concentration was calculated. PAM activity is described as ng bio-ADM formed per hour and L of sample and was normalized to the reaction without antibody addition, which was set as 100%.

Alternative bio-ADM assay: All components and conditions were as described by Weber et al., 2017 with an N-terminal anti-ADM antibody as solid-phase capture antibody instead of a mid-regional anti-ADM antibody.

No change in bio-ADM concentration was detected in samples without addition of exogenous ADM-Gly, neither in absence or in presence of HAM8101. When ADM-Gly was added to the sample, a linear formation of bio-ADM was detected within 90 minutes. When HAM8101 was present in the reaction in addition to ADM-Gly, a linear formation of bio-ADM was detected within 90 minutes that was increased by the factor of 4 after 90 minutes when compared to the reaction without HAM8101 (FIG. 8). All tested antibodies binding to the N-terminus of ADM increased the amidating activity, while HAM8101 showed the strongest influence (FIG. 9). All tested antibodies binding to the mid-regional part of ADM (either antibodies ADM38, ADM 41 and ADM43 directed to SEQ ID No. 15 with amino acids 21-32 of ADM or antibodies ADM2901, ADM2902 and ADM2903 directed to SEQ ID No. 49 with amino acids 27-39 of ADM) increased the amidating activity, while ADM43 showed the strongest influence. Moreover, the tested antibody ADM43 binding to MR-ADM increased the formation of bio-ADM significantly more than the NT-ADM antibodies. This clearly demonstrates, that the conversion of ADM-Gly to bio-ADM by human native PAM is significantly increased by N-terminal as well as mid-regional anti-ADM antibodies.

Example 6—Administration of NT-H in Healthy Humans and its In Vivo Effect on ADM-Gly to Bio-ADM Conversion The study was described in Geven et al. (Geven et al. 2017. *Intensive Care Med Exp* 5 (Suppl 2): 0427). Briefly, the study was conducted in healthy male subjects as a randomized, double-blind, placebo-controlled, study with single escalating doses of NT-H antibody (HAM8101) administered as intravenous (i.v.) infusion in 3 sequential groups of 8 healthy male subjects each (1st group 0.5 mg/kg, 2nd group 2 mg/kg, 3rd group 8 mg/kg) of healthy male subjects (n=6 active, n=2 placebo for each group). The main inclusion criteria were written informed consent, age 18-35 years, agreement to use a reliable way of contraception and a BMI between 18 and 30 kg/m². Subjects received a single i.v. dose of NT-H antibody (HAM8101) (0.5 mg/kg; 2 mg/kg; 8 mg/kg) or placebo by slow infusion over a 1-hour period in a research unit.

The baseline ADM-values in the 4 groups did not differ. Median ADM values were 7.1 pg/mL in the placebo group, 6.8 pg/mL in the first treatment group (0.5 mg/kg), 5.5 pg/mL in second treatment group (2 mg/kg) and 7.1 pg/mL in the third treatment group (8 mg/mL). The results show, that ADM-values rapidly increased within the first 1.5 hours after administration of NT-H antibody (HAM8101) in healthy human individuals, then reached a plateau and slowly declined (FIG. 10). Administration of NT-H antibody (HAM8101) was safe as the antibody did not influence heart rate, mean arterial pressure, peripheral oxygen saturation or temperature. Moreover, there were no significant differences between groups in routine haematological and biochemical safety laboratory measurements.

The formation of bio-ADM from ADM-Gly by recombinant human PAM enzyme and the invivo influence of the N-terminal anti-Adrenomedullin antibody HAM8101 using samples from healthy subjects that received HAM8101 was investigated by measuring the bio-ADM maturation activity (AMA).

Samples from n=3 subjects from each administration group before and 1 hour after administration of HAM8101 were used. Activity was determined as described for Serum samples in example 5b). The assay was calibrated using recombinant human PAM of known activity (InVivo Biotech Services GmbH, Hennigsdorf). Calibrators, controls and samples were treated in the same manner. The produced bio-ADM in the reaction-samples was quantified using the Sphingotest® bio-ADM assay (Weber et al., 2017). For each sample the difference of the t=40 min and t=0 min signal (RLUs, relative light units) was calculated and the signal (RLU(t40–t0 min)) of the calibrator was used to determine the AMA in tested serum samples. AMA is expressed as ng bio-ADM formed per hour and Liter of sample (ng/[h*L]).

FIGS. 11A and B show bio-ADM maturation activities (AMA) for each group before and 1, 4 and 24 hours after administration of HAM8101 as an average of activities from n=3 specimen. In all three groups AMA with ADM-Gly as substrate was increased after administration of the N-terminal anti-ADM antibody HAM8101 when compared to the activity before HAM8101 administration (FIG. 11A). While the difference in group 1 (0.5 mg/kg) was not significant in a one-way ANOVA, the differences in activity in group 2 (2 mg/kg) and group 3 (8 mg/kg) were significant (p<0.05 in group 2 and 3, respectively). In group 1 the AMA was increased by approximately 60%, 40% and 52% after 1 hour, 4 hours and 24 hours, respectively. In group 2 the AMA was increased by approximately 27%, 25% and 40% after 1 hour, 4 hours and 24 hours, respectively. In group 3 the AMA was increased by approximately 65%, 48% and 60% after 1 hour, 4 hours and 24 hours, respectively (FIG. 11 B). These results clearly demonstrate, that the conversion of ADM-Gly to bio-ADM by human native PAM is significantly increased by the presence of circulating N-terminal anti-ADM antibody HAM8101. To further demonstrate the enhanced conversion of ADM-Gly to bio-ADM by human native PAM we determined the bioADM and ADM-Gly levels in the samples described above. While the ratio of ADM-Gly/bio-ADM was above 1 in each group before administration of HAM8101, it surprisingly decreased to approximately 0.75 after 1 h in group 1, to 0.63 in group 2 and to 0.43 in group 3 (FIG. 12). Four hours after administration of HAM8101 the ratio further decreased to approximately 0.38, 0.25 and 0.38 in groups 1, 2 and 3 respectively. No further change of the ratio was detected in groups 1 and 2 after 24 hours, while a slight increase to approximately 0.5 was detected in group 3. These results clearly demonstrate, that the increased conversion of ADM-Gly to bio-ADM by human native PAM due to administration of HAM8101 shifts the ADM-Gly/bio-ADM ratio towards bio-ADM.

Example 7—Adrenomedullin and Outcome in
Sepsis and Septic Shock 1 (AdrenOSS-1) Study AdrenOSS-1 was a European prospective observational study. Twenty-four centers in five countries (France, Belgium, The Netherlands, Italy, and Germany) contributed to the trial achievement of 583 enrolled patients (recruited from June 2015 to May 2016). The study protocol was approved by the local ethics committees and was conducted in accordance with the Declaration of Helsinki. The study enrolled patients aged 18 years and older who were (1) admitted to the ICU for sepsis or septic shock or (2) transferred from another ICU in the state of sepsis and septic shock within less than 24 h after admission. Included patients were stratified by severe sepsis and septic shock based on definitions for sepsis and organ failure from 2001 (Levy et al. 2003. 2001 *SCCM/ESICM/ACCP/ATS/SIS International Sepsis Definitions Conference. Crit Care Med.* 31(4):1250-6). The term "sepsis" refers to the updated definition of Sepsis-3 (Singer et al. 2016 *The Third International Consensus Definitions for Sepsis and Septic Shock* (*Sepsis*-3). *JAMA.* 315(8):801-10). Patients were treated according to local practice, and treatments as well as procedures were registered. The primary endpoint was 28-day mortality. Secondary endpoints concerned organ failure (as defined by the Sequential Organ Failure Assessment [SOFA] score) and organ support, vasopressor/inotrope use, fluid balance, and use of renal replacement therapy (RRT).

Upon admission, demographics (age, sex), body mass index, presence of septic shock, type of ICU admission, organ dysfunction scores (SOFA, Acute Physiologic Assessment and Chronic Health Evaluation II [APACHE II]), origin of sepsis, pre-existing comorbidities (i.e., treated within the last year), past medical history, laboratory values, and organ support were recorded, and blood was drawn for measurement of bio-ADM and other markers. After patient enrollment, the following data were collected daily during the first week: SOFA score, antimicrobial therapies, fluid balance, ventilation status, Glasgow Coma Scale score, central venous pressure, need for RRT, invasive procedures for sepsis control, and vasopressor/inotrope treatment. Moreover, discharge status and mortality were recorded on day 28 after ICU admission. Blood for the central laboratory was sampled within 24 h after ICU admission and on day 2 (mean 47 h, SD 9 h) after the first sample. Samples were subsequently processed and stored at −80° C.

Bio-ADM was measured using a recently developed immunoassay as described in Weber et al. (Weber et al. 2017. *JALM* 2(2): 222-233). ADM-Gly was measured as described in example 4 in a randomly chosen subset of available samples (n=170). Bio-ADM and the ADM-Gly/bio-ADM ratio correlated significantly (r=0.25, p=0.0011) (FIG. 13).

In the patient population described above (patients from AdrenOSS-I with sepsis, severe sepsis or septic shock) the ratio of plasma ADM-Gly and bioADM on day 1 after admission was determined as described above. Using the ratio's median as a simple cut-off value of 3.01, the population was segmented in two groups (above and below 3.01) and the corresponding 28-day survival rates were depicted in a Kaplan-Meier-Plot (FIG. 14). Patients with an ADM-Gly/bio-ADM ratio below 3.01 on the day of admission had a high survival rate of 84.7% (95% CI: 77.4-92.7), whereas, when the ratio increased over 3.01, the survival rate was lowered to 71.8% (95% CI: 62.8-82). The two ADM-Gly/bio-ADM ratio groups could stratify the survival probability, and the HR was significantly higher when ADM-Gly/bio-ADM ratio above median was compared with the ratio group below median (HR=2.04).

Example 8—Comparison of ADM-Gly/Bio-ADM
Ratio in Healthy, Healthy-Treated and Critically Ill
Patients (Survivors and Non-Survivors)

Critically ill subjects were from the AdrenOSS-I cohort described in example 7. Healthy and healthy HAM8101 treated subjects were from the study cohort described in example 6 (Geven et al. 2017. *Intensive Care Med Exp* 5 (Suppl 2): 0427). Bio-ADM was determined as described by Weber et al., 2017. ADM-Gly was determined as described in example 4.

TABLE 4

| comparison of ADM-Gly/bio-ADM ratios | | | |
|---|---|---|---|
| | ADM-Gly/bioADM Ratio | Standard deviation | n Subjects |
| Critically ill (non-survivors) | 5.2 | 4.97 | 37 |
| Critically ill (survivors) | 3.9 | 3.67 | 133 |
| Healthy | 1.29 | 0.13 | 9 |
| Healthy HAM8101 treated (1 h) | 0.61 | 0.33 | 9 |
| Healthy HAM8101 treated (4 h) | 0.33 | 0.13 | 9 |

Description of Results

Critically ill patients who died within of 28 days after admission to ICU showed an ADM-Gly/bio-ADM ratio of 5.2. The ratio of critically ill subjects surviving 28 days after ICU admission had a surprisingly significantly lower ADM-Gly/bio-ADM ratio of 3.9 (p=0.0116). In comparison to critically ill subjects, healthy subject had a further significantly reduced ADM-Gly/bio-ADM ratio of 1.29 (p<0.05). Surprisingly, healthy subjects who received HAM8101 had a further significantly reduced ADM-Gly/bio-ADM ratio 1 h after HAM8101 administration (p=0.0002). Four hours after administration of HAM8101 the ratio further decreased to 0.33 (p=0.0354) showing a direct influence of HAM8101 on ADM-Gly to bio-ADM conversion rate here expressed as the ratio of ADM-Gly/bio-ADM.

Example 9—Comparison of
MR-proADM/Bio-ADM Ratio in Healthy,
Healthy-Treated and Critically Ill Patients
(Survivors and Non-Survivors)

The same patients as described in example 8 were also analysed for their MR-proADM/ADM-NH$_2$ ratio.

TABLE 5

| comparison of MR-proADM/bio-ADM ratios | | | |
|---|---|---|---|
| | MR-proADM/bio-ADM ratio | Standard deviation | n Subjects |
| Critically ill (non-survivors) | 293.2 | 178.8 | 36 |
| Critically ill (survivors) | 283.9 | 131.7 | 130 |

TABLE 5-continued comparison of MR-proADM/bio-ADM ratios

| | MR-proADM/bio-ADM ratio | Standard deviation | n Subjects |
|---|---|---|---|
| Healthy | 239.4 | 50.1 | 24 |
| Healthy HAM8101 treated (1 h) | 44.6 | 32.1 | 18 |
| Healthy HAM8101 treated (4 h) | 42.4 | 32.0 | 18 |

Description of Results

Critically ill patients who died within of 28 days after admission to ICU showed a MR-proADM/bio-ADM ratio of 293.2, whereas the ratio of critically ill subjects surviving 28 days after ICU admission had a lower ratio of 283.9. In comparison to critically ill subjects, healthy subject had a reduced MR-proADM/bio-ADM ratio of 239.4. Surprisingly, healthy subjects who received HAM8101 had a further significantly reduced MR-proADM/bio-ADM ratio 1 h after HAM8101 administration (p<0.0001). Four hours after administration of HAM8101 the ratio did not decrease any further.

Example 10—Influence of N-Terminal Anti-Adrenomedullin Antibodies and L-Ascorbate on the Velocity of Bio-ADM Formation from Exogenous ADM-Gly by PAM A serial antibody-dilution with concentrations of 0, 5, 10, 50, 100, 500 and 3000 µg/mL per well, respectively (in 20 µl) were pipetted into 96-well micro-titer plates. Then 160 µl PAM reaction buffer (100 mM Tris-HCl, 6.25 µM CuSO$_4$, 62.5 µM amastatin, 250 µM leupeptin, 36 ng/mL ADM-Gly)

with varying L-ascorbate concentrations was added to the wells and incubated for 15 min. Afterwards the reaction was started by addition of 20 µl of Li-Heparin plasma, containing native PAM Immediately after addition of plasma, 100 µl from each well were removed and inactivated by addition of EDTA (20 mM final concentration) to generate a t=0 minutes reaction point. Inactivated and non-inactivated samples were incubated for 40 minutes at 37° C. and the reaction in non-inactivated samples was stopped as described above. For quantification of produced ADM-NH$_2$ the Sphingotest® bio-ADM Kit (Weber et al. 2017) was utilized according to manufacturer's manual. The ADM maturation activity (AMA) was calculated according to equation 1 (DF=dilution factor of sample matrix).

$$AMA = \frac{[bio-ADM; t = 40 \text{ min}]\left(\frac{ng}{L}\right) - [bio-ADM; t = 0 \text{ min}]\left(\frac{ng}{L}\right) * 60 \text{ min} * DF}{40 \text{ min} * 1 \text{ h}}$$

Increasing concentrations of ascorbate in the range of 0.4-2 mM led to increasing ADM maturation activities (FIG. 15). The overall ascorbate dependency of the amidating reaction was not changed by addition of HAM8101, i.e., the activity optimum remained at 0.8-2 mM of ascorbate. However, the presence of HAM8101 in the amidation assay showed a concentration dependent positive effect on the amidation for each ascorbate concentration assayed. The presence of 100 µg/mL of HAM8101 in the amidation assay increased the bio-ADM formation of PAM by 40%. These results clearly demonstrate that a combination of N-terminal anti-ADM antibodies with ascorbate significantly enhance the activity of the PAM enzyme and the formation of bio-ADM in plasma.

SEQUENCES

```
SEQ ID No.: 1
GYTFSRYW

SEQ ID No.: 2
ILPGSGST

SEQ ID No.: 3
TEGYEYDGFDY

SEQ ID No.: 4
QSIVYSNGNTY

SEQUENCE "RVS" (not part of the Sequencing Listing):
RVS

SEQ ID No.: 5
FQGSHIPYT

SEQ ID No.: 6 (AM-VH-C)
QVQLQQSGAELMKPGASVKISCKATGYTFSRYWIEWVKQRPGHGLEWIGEILPGSGS
TNYNEKFKGKATITADTSSNTAYMQLSSLTSEDSAVYYCTEGYEYDGFDYWGQGTT
LTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPK

SEQ ID No.: 7 (AM-VH1)
QVQLVQSGAEVKKPGSSVKVSCKASGYTFSRYWISWVRQAPGQGLEWMGRILPGSG
STNYAQKFQGRVTITADESTSTAYMELSSLRSEDTAVYYCTEGYEYDGFDYWGQGT
TVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPK

SEQ ID No.: 8 (AM-VH2-E40)
QVQLVQSGAEVKKPGSSVKVSCKASGYTFSRYWIEWVRQAPGQGLEWMGRILPGSG
STNYAQKFQGRVTITADESTSTAYMELSSLRSEDTAVYYCTEGYEYDGFDYWGQGT
```

-continued

| SEQUENCES |
| --- |

```
TVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPK

SEQ ID No.: 9 (AM-VH3-T26-E55)
QVQLVQSGAEVKKPGSSVKVSCKATGYTFSRYWISWVRQAPGQGLEWMGEILPGSG
STNYAQKFQGRVTITADESTSTAYMELSSLRSEDTAVYYCTEGYEYDGFDYWGQGT
TVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPK

SEQ ID No.: 10 (AM-VH4-T26-E40-E55)
QVQLVQSGAEVKKPGSSVKVSCKATGYTFSRYWIEWVRQAPGQGLEWMGEILPGSG
STNYAQKFQGRVTITADESTSTAYMELSSLRSEDTAVYYCTEGYEYDGFDYWGQGT
TVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPK

SEQ ID No.: 11 (AM-VL-C)
DVLLSQTPLSLPVSLGDQATISCRSSQSIVYSNGNTYLEWYLQKPGQSPKLLIYRVSNR
FSGVPDRFSGSGSGTDFTLKISRVEAEDLGVYYCFQGSHIPYTFGGGTKLEIKRTVAAP
SVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

SEQ ID No.: 12 (AM-VL1)
DVVMTQSPLSLPVTLGQPASISCRSSQSIVYSNGNTYLNWFQQRPGQSPRRLIYRVSN
RDSGVPDRFSGSGSGTDFTLKISRVEAEDVGVYYCFQGSHIPYTFGQGTKLEIKRTVA
APSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No.: 13 (AM-VL2-E40)
DVVMTQSPLSLPVTLGQPASISCRSSQSIVYSNGNTYLEWFQQRPGQSPRRLIYRVSN
RDSGVPDRFSGSGSGTDFTLKISRVEAEDVGVYYCFQGSHIPYTFGQGTKLEIKRTVA
APSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID No.: 14 (human ADM 1-21)
YRQSMNNFQGLRSFGCRFGTC

SEQ ID No.: 15 (human ADM 21-32)
CTVQKLAHQIYQ

SEQ ID No.: 16 (human ADM C-42-52)
CAPRSKISPQGY-CONH₂
```

SEQ ID No.: 16 (human ADM C-42-52)
CAPRSKISPQGY-CONH$_2$

```
SEQ ID No.: 17 (murine ADM 1-19)
YRQSMNQGSRSNGCRFGTC

SEQ ID No.: 18 (murine ADM 19-31)
CTFQKLAHQIYQ

SEQ ID No.: 19 (murine ADM C-40-50)
```
CAPRNKISPQGY-CONH$_2$

SEQ ID No.: 20 (mature human Adrenomedullin (mature ADM); amidated ADM; bio-ADM):
amino acids 1-52 or amino acids 95-146 of pro-ADM
YRQSMNNFQGLRSFGCRFGTCTVQKLAHQIYQFTDKDKDNVAPRSKISPQGY-
CONH$_2$ SEQ ID No.: 21 (Adrenomedullin 1-52-Gly (ADM 1-52-Gly): amino acids 95-147 of
preproADM)
YRQSMN NFQGLRSFGC RFGTCTVQKL AHQIYQFTDK DKDNVAPRSK ISPQGYG SEQ ID No.: 22 (Murine ADM 1-50)
YRQSMNQGSRSNGCRFGTCTFQKLAHQIYQLTDKDKDGMAPRNKISPQGY-CONH$_2$ SEQ ID No.: 23 (1-42 of human ADM):
YRQSMNNFQGLRSFGCRFGTCTVQKLAHQIYQFTDKDKDNVA SEQ ID No.: 24 (aa 43-52 of human ADM)
PRSKISPQGY-NH$_2$ SEQ ID No.: 25 (aa 1-14 of human ADM)
YRQSMNNFQGLRSF SEQ ID No.: 26 (aa 1-10 of human ADM)
YRQSMNNFQG SEQ ID No.: 27 (aa 1-6 of human ADM)
YRQSMN

SEQUENCES

SEQ ID No.: 28 (aa 1-32 of human ADM)
YRQSMNNFQGLRSFGCRFGTCTVQKLAHQIYQ

SEQ ID No.: 29 (aa 1-40 murine ADM)
YRQSMNQGSRSNGCRFGTCTFQKLAHQIYQLTDKDKDGMA

SEQ ID No.: 30 (aa 1-31 murine ADM)
YRQSMNQGSRSNGCRFGTCTFQKLAHQIYQL

SEQ ID No.: 31 (proADM: 164 amino acids (22-185 of preproADM))
ARLDVASEF RKKWNKWALS RGKRELRMSS SYPTGLADVK AGPAQTLIRP
QDMKGASRSP EDSSPDAARI RVKRYRQSMN NFQGLRSFGC RFGTCTVQKL
AHQIYQFTDK DKDNVAPRSK ISPQGYGRRR RRSLPEAGPG RTLVSSKPQA
HGAPAPPSGS APHFL SEQ ID No.: 32 (Proadrenomedullin N-20 terminal peptide, PAMP: amino acids 22-41 of
preproADM)
ARLDVASEF RKKWNKWALS R SEQ ID No.: 33 (Midregional proAdrenomedullin, MR-proADM: amino acids 45-92 of
preproADM)
ELRMSS SYPTGLADVK AGPAQTLIRP QDMKGASRSP EDSSPDAARI RV SEQ ID No.: 34 (C-terminal proAdrenomedullin, CT-proADM: amino acids 148-185 of
preproADM)
RRR RRSLPEAGPG RTLVSSKPQA HGAPAPPSGS APHFL SEQ ID No.: 35 (heavy chain, HAM8101)
QVQLVQSGAEVKKPGSSVKVSCKASGYTFSRYWIEWVRQAPGQGLEWIGEILPGSGS
TNYNQKFQGRVTITADTSTSTAYMELSSLRSEDTAVYYCTEGYEYDGFDYWGQGTT
VTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVLD
SDGSFFLYSKLTVDKSRWQQGNVFScSVMHEALHNHYTQKSLSLSPGK SEQ ID No.: 36 (light chain, HAM 8101)
DVVLTQSPLSLPVTLGQPASISCRSSQSIVYSNGNTYLEWYLQRPGQSPRLLIYRVSNR
FSGVPDRFSGSGSGTDFTLKISRVEAEDVGVYYCFQGSHIPYTFGGGTKLEIKRTVAA
PSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC SEQ ID No.: 37-IGHV1-69*11
QVQLVQSGAEVKKPGSSVKVSCKASGGTFSSYAISWVRQAPGQGLEWMGRIIPILGT
ANYAQKFQGRVTITADESTSTAYMELSSLRSEDTAVYYCARYYYYYGMDVWGQGT
TVTVSS SEQ ID No. 38: -HB3
QVQLQQSGAELMKPGASVKISCKATGYTFSRYWIEWVKQRPGHGLEWIGEILPGSGS
TNYNEKFKGKATITADTSSNTAYMQLSSLTSEDSAVYYCTEGYEYDGFDYWGQGTT
LTVSS SEQ ID NO: 39-Prepro-PAM isoform 1 AS 1-973
         10        20        30        40        50
MAGRVPSLLV LLVFPSSCLA FRSPLSVFKR FKETTRPFSN ECLGTTRPVV 60        70        80        90       100
PIDSSDFALD IRMPGVTPKQ SDTYFCMSMR IPVDEEAFVI DFKPRASMDT 110       120       130       140       150
VHHMLLFGCN MPSSTGSYWF CDEGTCTDKA NILYAWARNA PPTRLPKGVG 160       170       180       190       200
FRVGGETGSK YFVLQVHYGD ISAFRDNNKD CSGVSLHLTR LPQPLIAGMY 210       220       230       240       250
LMMSVDTVIP AGEKVVNSDI SCHYKNYPMH VFAYRVHTHH LGKVVSGYRV 260       270       280       290       300
RNGQWTLIGR QSPQLPQAFY PVGHPVDVSF GDLLAARCVF TGEGRTEATH 310       320       330       340       350
IGGTSSDEMC NLYIMYYMEA KHAVSFMTCT QNVAPDMFRT IPPEANIPIP 360       370       380       390       400

-continued

---

| SEQUENCES |
|---|

VKSDMVMMHE HHKETEYKDK IPLLQQPKRE EEEVLDQGDF YSLLSKLLGE

```
        410        420        430        440        450
REDVVHVHKY NPTEKAESES DLVAEIANVV QKKDLGRSDA REGAEHERGN 460        470        480        490        500
AILVRDRIHK FHRLVSTLRP PESRVFSLQQ PPPGEGTWEP EHTGDFHMEE 510        520        530        540        550
ALDWPGVYLL PGQVSGVALD PKNNLVIFHR GDHVWDGNSF DSKFVYQQIG 560        570        580        590        600
LGPIEEDTIL VIDPNNAAVL QSSGKNLFYL PHGLSIDKDG NYWVTDVALH 610        620        630        640        650
QVFKLDPNNK EGPVLILGRS MQPGSDQNHF CQPTDVAVDP GTGAIYVSDG 660        670        680        690        700
YCNSRIVQFS PSGKFITQWG EESSGSSPLP GQFTVPHSLA LVPLLGQLCV 710        720        730        740        750
ADRENGRIQC FKTDTKEFVR EIKHSSFGRN VFAISYIPGL LFAVNGKPHF 760        770        780        790        800
GDQEPVQGFV MNFSNGEIID IFKPVRKHFD MPHDIVASED GTVYIGDAHT 810        820        830        840        850
NTVWKFTLTE KLEHRSVKKA GIEVQEIKEA EAVVETKMEN KPTSSELQKM 860        870        880        890        900
QEKQKLIKEP GSGVPVVLIT TLLVIPVVVL LAIAIFIRWK KSRAFGDSEH 910        920        930        940        950
KLETSSGRVL GRFRGKGSGG LNLGNFFASR KGYSRKGFDR LSTEGSDQEK 960        970
EDDGSESEEE YSAPLPALAP SSS
```

SEQ ID NO: 40-Prepro-PAM isoform 2 AS 1-868
```
        10         20         30         40         50
MAGRVPSLLV LLVFPSSCLA FRSPLSVFKR FKETTRPFSN ECLGTTRPVV 60         70         80         90        100
PIDSSDFALD IRMPGVTPKQ SDTYFCMSMR IPVDEEAFVI DFKPRASMDT 110        120        130        140        150
VHHMLLFGCN MPSSTGSYWF CDEGTCTDKA NILYAWARNA PPTRLPKGVG 160        170        180        190        200
FRVGGETGSK YFVLQVHYGD ISAFRDNNKD CSGVSLHLTR LPQPLIAGMY 210        220        230        240        250
LMMSVDTVIP AGEKVVNSDI SCHYKNYPMH VFAYRVHTHH LGKVVSGYRV 260        270        280        290        300
RNGQWTLIGR QSPQLPQAFY PVGHPVDVSF GDLLAARCVF TGEGRTEATH 310        320        330        340        350
IGGTSSDEMC NLYIMYYMEA KHAVSFMTCT QNVAPDMFRT IPPEANIPIP 360        370        380        390        400
VKSDMVMMHE HHKETEYKDK IPLLQQPKRE EEEVLDQDFH MEEALDWPGV 410        420        430        440        450
YLLPGQVSGV ALDPKNNLVI FHRGDHVWDG NSFDSKFVYQ QIGLGPIEED 460        470        480        490        500
TILVIDPNNA AVLQSSGKNL FYLPHGLSID KDGNYWVTDV ALHQVFKLDP 510        520        530        540        550
NNKEGPVLIL GRSMQPGSDQ NHFCQPTDVA VDPGTGAIYV SDGYCNSRIV 560        570        580        590        600
QFSPSGKFIT QWGEESSGSS PLPGQFTVPH SLALVPLLGQ LCVADRENGR 610        620        630        640        650
IQCFKTDTKE FVREIKHSSF GRNVFAISYI PGLLFAVNGK PHFGDQEPVQ
```

-continued

| SEQUENCES |
| --- |

```
       660        670        680        690        700
GFVMNFSNGE IIDIFKPVRK HFDMPHDIVA SEDGTVYIGD AHTNTVWKFT 710        720        730        740        750
LTEKLEHRSV KKAGIEVQEI KEAEAVVETK MENKPTSSEL QKMQEKQKLI 760        770        780        790        800
KEPGSGVPVV LITTLLVIPV VVLLAIAIFI RWKKSRAFGD SEHKLETSSG 810        820        830        840        850
RVLGRFRGKG SGGLNLGNFF ASRKGYSRKG FDRLSTEGSD QEKEDDGSES

860
EEEYSAPLPA LAPSSS

SEQ ID No.: 41-Prepro-PAM isoform 3 AS (amino acids 829-896 of SEQ ID No. 1 missing)
        10         20         30         40         50
MAGRVPSLLV LLVFPSSCLA FRSPLSVFKR FKETTRPFSN ECLGTTRPVV 60         70         80         90        100
PIDSSDFALD IRMPGVTPKQ SDTYFCMSMR IPVDEEAFVI DFKPRASMDT 110        120        130        140        150
VHHMLLFGCN MPSSTGSYWF CDEGTCTDKA NILYAWARNA PPTRLPKGVG 160        170        180        190        200
FRVGGETGSK YFVLQVHYGD ISAFRDNNKD CSGVSLHLTR LPQPLIAGMY 210        220        230        240        250
LMMSVDTVIP AGEKVVNSDI SCHYKNYPMH VFAYRVHTHH LGKVVSGYRV 260        270        280        290        300
RNGQWTLIGR QSPQLPQAFY PVGHPVDVSF GDLLAARCVF TGEGRTEATH 310        320        330        340        350
IGGTSSDEMC NLYIMYYMEA KHAVSFMTCT QNVAPDMFRT IPPEANIPIP 360        370        380        390        400
VKSDMVMMHE HHKETEYKDK IPLLQQPKRE EEEVLDQGDF YSLLSKLLGE 410        420        430        440        450
REDVVHVHKY NPTEKAESES DLVAEIANVV QKKDLGRSDA REGAEHERGN 460        470        480        490        500
AILVRDRIHK FHRLVSTLRP PESRVFSLQQ PPPGEGTWEP EHTGDFHMEE 510        520        530        540        550
ALDWPGVYLL PGQVSGVALD PKNNLVIFHR GDHVWDGNSF DSKFVYQQIG 560        570        580        590        600
LGPIEEDTIL VIDPNNAAVL QSSGKNLFYL PHGLSIDKDG NYWVTDVALH 610        620        630        640        650
QVFKLDPNNK EGPVLILGRS MQPGSDQNHF CQPTDVAVDP GTGAIYVSDG 660        670        680        690        700
YCNSRIVQFS PSGKFITQWG EESSGSSPLP GQFTVPHSLA LVPLLGQLCV 710        720        730        740        750
ADRENGRIQC FKTDTKEFVR EIKHSSFGRN VFAISYIPGL LFAVNGKPHF 760        770        780        790        800
GDQEPVQGFV MNFSNGEIID IFKPVRKHFD MPHDIVASED GTVYIGDAHT 810        820        830        840        850
NTVWKFTLTE KLEHRSVKKA GIEVQEIKDS EHKLETSSGR VLGRFRGKGS 860        870        880        890        900
GGLNLGNFFA SRKGYSRKGF DRLSTEGSDQ EKEDDGSESE EEYSAPLPAL

905
APSSS

SEQ ID No. 42-Prepro-PAM isoform 4 (amino acids 829-914 of SEQ ID No. 1 missing)
        10         20         30         40         50
MAGRVPSLLV LLVFPSSCLA FRSPLSVFKR FKETTRPFSN ECLGTTRPVV
```

-continued

---
SEQUENCES
---

```
        60         70         80         90        100
PIDSSDFALD IRMPGVTPKQ SDTYFCMSMR IPVDEEAFVI DFKPRASMDT 110        120        130        140        150
VHHMLLFGCN MPSSTGSYWF CDEGTCTDKA NILYAWARNA PPTRLPKGVG 160        170        180        190        200
FRVGGETGSK YFVLQVHYGD ISAFRDNNKD CSGVSLHLTR LPQPLIAGMY 210        220        230        240        250
LMMSVDTVIP AGEKVVNSDI SCHYKNYPMH VFAYRVHTHH LGKVVSGYRV 260        270        280        290        300
RNGQWTLIGR QSPOLPOAFY PVGHPVDVSF GDLLAARCVE TGEGRTEATH 310        320        330        340        350
IGGTSSDEMC NLYIMYYMEA KHAVSFMTCT QNVAPDMFRT IPPEANIPIP 360        370        380        390        400
VKSDMVMMHE HHKETEYKDK IPLLQQPKRE EEEVLDQGDF YSLLSKLLGE 410        420        430        440        450
REDVVHVHKY NPTEKAESES DLVABIANVV QKKDLGRSDA REGAEHERGN 460        470        480        490        500
AILVRDRIHK FHRLVSTLRP PESRVFSLQQ PPPGEGTWEP EHTGDFHMEE 510        520        530        540        550
ALDWPGVYLL PGQVSGVALD PKNNLVIFHR GDHVWDGNSF DSKEVYQQIG 560        570        580        590        600
LGPIEEDTIL VIDPNNAAVL QSSGKNLFYL PHGLSIDKDG NYWVTDVALH 610        620        630        640        650
QVEKLDPNNK EGPVLILGRS MQPGSDQNHF CQPTDVAVDP GTGAIYVSDG 660        670        680        690        700
YCNSRIVQFS PSGKFITOWG EESSGSSPLP GQFTVPHSLA LVPLLGQLCV 710        720        730        740        750
ADRENGRIQC FKTDTKEFVR EIKHSSFGRN VFAISYIPGL LFAVNGKPHE 760        770        780        790        800
GDQEPVQGFV MNFSNGEIID IFKPVRKHFD MPHDIVASED GTVYIGDAHT 810        820        830        840        850
NTVWKFTLTE KLEHRSVKKA GIEVQEIKGK GSGGLNLGNF FASRKGYSRK 860        870        880
GFDRLSTEGS DQEKEDDGSE SEEEYSAPLP ALAPSSS

SEQ ID No. 43-Prepro-PAM Isoform 5 (Isoform 1 with an additional aa in position 896)
        10         20         30         40         50
MAGRVPSLLV LLVFPSSCLA FRSPLSVFKR FKETTRPFSN ECLGTTRPVV 60         70         80         90        100
PIDSSDFALD IRMPGVTPKQ SDTYFCMSMR IPVDEEAFVI DFKPRASMDT 110        120        130        140        150
VHHMLLFGCN MPSSTGSYWF CDEGTCTDKA NILYAWARNA PPTRLPKGVG 160        170        180        190        200
FRVGGETGSK YFVLQVHYGD ISAFRDNNKD CSGVSLHLTR LPQPLIAGMY 210        220        230        240        250
LMMSVDTVIP AGEKVVNSDI SCHYKNYPMH VFAYRVHTHH LGKVVSGYRV 260        270        280        290        300
RNGQWTLIGR QSPQLPQAFY PVGHPVDVSF GDLLAARCVE TGEGRTEATH 310        320        330        340        350
IGGTSSDEMC NLYIMYYMEA KHAVSFMTCT QNVAPDMFRT IPPEANIPIP 360        370        380        390        400
VKSDMVMMHE HHKETEYKDK IPLLQQPKRE EEEVLDQGDF YSLLSKLLGE
```

-continued

| SEQUENCES |
|---|

```
        410        420        430        440        450
REDVVHVHKY NPTEKAESES DLVABIANVV QKKDLGRSDA REGAEHERGN 460        470        480        490        500
AILVRDRIHK FHRLVSTLRP PESRVFSLQQ PPPGEGTWEP EHTGDFHMEE 510        520        530        540        550
ALDWPGVYLL PGQVSGVALD PKNNLVIFHR GDHVWDGNSF DSKFVYQQIG 560        570        580        590        600
LGPIEEDTIL VIDPNNAAVL QSSGKNLFYL PHGLSIDKDG NYWVTDVALH 610        620        630        640        650
QVFKLDPNNK EGPVLILGRS MQPGSDONHF CQPTDVAVDP GTGAIYVSDG 660        670        680        690        700
YCNSRIVQFS PSGKFITOWG EESSGSSPLP GQFTVPHSLA LVPLLGQLCV 710        720        730        740        750
ADRENGRIQC FKTDTKEFVR EIKHSSFGRN VFAISYIPGL LFAVNGKPHE 760        770        780        790        800
GDQEPVQGFV MNFSNGEIID IFKPVRKHFD MPHDIVASED GTVYIGDAHT 810        820        830        840        850
NTVWKFTLTE KLEHRSVKKA GIEVQEIKEA EAVVETKMEN KPTSSELQKM 860        870        880        890        900
QEKQKLIKEP GSGVPVVLIT TLLVIPVVVL LAIAIFIRWK KSRAFGADSE 910        920        930        940        950
HKLETSSGRV LGRFRGKGSG GLNLGNFFAS RKGYSRKGFD RLSTEGSDQE 960        970
KEDDGSESEE EYSAPLPALA PSSS

SEQ ID No. 44-Prepro-PAM Isoform 6 (amino acids 897-914 of SEQ ID No. 1 missing)
         10         20         30         40         50
MAGRVPSLLV LLVFPSSCLA FRSPLSVFKR FKETTRPFSN ECLGTTRPVV 60         70         80         90        100
PIDSSDFALD IRMPGVTPKQ SDTYFCMSMR IPVDEEAFVI DFKPRASMDT 110        120        130        140        150
VHHMLLFGCN MPSSTGSYWF CDEGTCTDKA NILYAWARNA PPTRLPKGVG 160        170        180        190        200
FRVGGETGSK YFVLQVHYGD ISAFRDNNKD CSGVSLHLTR LPQPLIAGMY 210        220        230        240        250
LMMSVDTVIP AGEKVVNSDI SCHYKNYPMH VFAYRVHTHH LGKVVSGYRV 260        270        280        290        300
RNGQWTLIGR QSPQLPQAFY PVGHPVDVSF GDLLAARCVF TGEGRTEATH 310        320        330        340        350
IGGISSDEMC NLYIMYYMEA KHAVSFMTCT QNVAPDMERT IPPEANIPIP 360        370        380        390        400
VKSDMVMMHE HHKETEYKDK IPLLQQPKRE EEEVLDQGDF YSLLSKLLGE 410        420        430        440        450
REDVVHVHKY NPTEKAESES DLVAEIANVV QKKDLGRSDA REGAEHERGN 460        470        480        490        500
AILVRDRIHK FHRLVSTLRP PESRVFSLQQ PPPGEGTWEP EHTGDFHMEE 510        520        530        540        550
ALDWPGVYLL PGQVSGVALD PKNNLVIFHR GDHVWDGNSF DSKEVYQQIG 560        570        580        590        600
LGPIEEDTIL VIDPNNAAVL QSSGKNLFYL PHGLSIDKDG NYWVTDVALH 610        620        630        640        650
QVFKLDPNNK EGPVLILGRS MQPGSDONHF CQPTDVAVDP GTGAIYVSDG 660        670        680        690        700
```

| SEQUENCES |
| --- |

```
YCNSRIVQFS PSGKFITQWG EESSGSSPLP GQFTVPHSLA LVPLLGQLCV 710        720        730        740        750
ADRENGRIQC FKTDTKEFVR EIKHSSFGRN VFAISYIPGL LFAVNGKPHE 760        770        780        790        800
GDQEPVQGFV MNFSNGEIID IFKPVRKHED MPHDIVASED GTVYIGDAHT 810        820        830        840        850
NTVWKFTLTE KLEHRSVKKA GIEVQEIKEA EAVVETKMEN KPTSSELQKM 860        870        880        890        900
QEKQKLIKEP GSGVPVVLIT TLLVIPVVVL LAIAIFIRWK KSRAFGGKGS 910        920        930        940        950
GGLNLGNFFA SRKGYSRKGF DRLSTEGSDQ EKEDDGSESE EEYSAPLPAL

APSSS

SEQ ID No. 45-PHM subunit of PAM
          10         20         30         40         50
FKETTRPFSN ECLGTTRPVV PIDSSDFALD IRMPGVTPKQ SDTYFCMSMR 60         70         80         90        100
IPVDEEAFVI DFKPRASMDT VHHMLLFGCN MPSSTGSYWF CDEGTCTDKA 110        120        130        140        150
NILYAWARNA PPTRLPKGVG FRVGGETGSK YFVLQVHYGD ISAFRDNNKD 160        170        180        190        200
CSGVSLHLTR LPQPLIAGMY LMMSVDTVIP AGEKVVNSDI SCHYKNYPMH 210        220        230        240        250
VFAYRVHTHH LGKVVSGYRV RNGQWTLIGR QSPOLPQAFY PVGHPVDVSF 260        270        280        290        300
GDLLAARCVF TGEGRTEATH IGGTSSDEMC NLYIMYYMEA KHAVSFMTCT 310        320        330        340        350
QNVAPDMFRT IPPEANIPIP VKSDMVMMHE HHKETEYKDK IPLLQQPKRE 360        370        380        390        400
EEEVLDQGDF YSLLSKLLGE REDVVHVHKY NPTEKAESES DLVAEIANVV 410        420        430        440        450
QKKDLGRSDA REGAEHERGN AILVRDRIHK FHRLVSTLRP PESRVFSLQQ

460
PPPGEGTWEP EHTG

SEQ ID No. 46-PAL subunit of PAM
          10         20         30         40         50
DFHMEEALDW PGVYLLPGQV SGVALDPKNN LVIFHRGDHV WDGNSFDSKF 60         70         80         90        100
VYQQIGLGPI EEDTILVIDP NNAAVLQSSG KNLFYLPHGL SIDKDGNYWV 110        120        130        140        150
TDVALHQVFK LDPNNKEGPV LILGRSMQPG SDQNHFCQPT DVAVDPGTGA 160        170        180        190        200
IYVSDGYCNS RIVQFSPSGK FITQWGEESS GSSPLPGQFT VPHSLALVPL 210        220        230        240        250
LGQLCVADRE NGRIQCFKTD TKEFVREIKH SSFGRNVFAI SYIPGLLFAV 260        270        280        290        300
NGKPHFGDQE PVQGFVMNFS NGEIIDIFKP VRKHFDMPHD IVASEDGTVY 310        320
IGDAHTNTVW KFTLTEKLEH RSV SEQ ID No. 47-Sequence of recombinant human PAM
          10         20         30         40         50
SPLSVFKRFK ETTRPFSNEC LGTTRPVVPI DSSDFALDIR MPGVTPKQSD 60         70         80         90        100
```

| SEQUENCES |
|---|

```
TYFCMSMRIP VDEEAFVIDF KPRASMDTVH HMLLFGCNMP SSTGSYWFCD 110        120        130        140        150
EGTCTDKANI LYAWARNAPP TRLPKGVGFR VGGETGSKYF VLQVHYGDIS 160        170        180        190        200
AFRDNNKDCS GVSLHLTRLP QPLIAGMYLM MSVDTVIPAG EKVVNSDISC 210        220        230        240        250
HYKNYPMHVF AYRVHTHHLG KVVSGYRVRN GOWTLIGRQS PQLPQAFYPV 260        270        280        290        300
GHPVDVSFGD LLAARCVFTG EGRTEATHIG GTSSDEMCNL YIMYYMEAKH 310        320        330        340        350
AVSFMTCTQN VAPDMFRTIP PEANIPIPVK SDMVMMHEHH KETEYKDKIP 360        370        380        390        400
LLQQPKREEE EVLDQGDFYS LLSKLLGERE DVVHVHKYNP TEKAESESDL 410        420        430        440        450
VAEIANVVQK KDLGRSDARE GAEHERGNAI LVRDRIHKFH RLVSTLRPPE 460        470        480        490        500
SRVFSLQQPP PGEGTWEPEH TGDFHMEEAL DWPGVYLLPG QVSGVALDPK 510        520        530        540        550
NNLVIFHRGD HVWDGNSFDS KFVYQQIGLG PIEEDTILVI DPNNAAVLQS 560        570        580        590        600
SGKNLFYLPH GLSIDKDGNY WVTDVALHQV FKLDPNNKEG PVLILGRSMQ 610        620        630        640        650
PGSDQNHFCQ PTDVAVDPGT GAIYVSDGYC NSRIVQFSPS GKFITQWGEE 660        670        680        690        700
SSGSSPLPGQ FTVPHSLALV PLLGQLCVAD RENGRIQCFK TDTKEFVREI 710        720        730        740        750
KHSSFGRNVF AISYIPGLLF AVNGKPHFGD QEPVQGFVMN FSNGEIIDIF 760        770        780        790        800
KPVRKHFDMP HDIVASEDGT VYIGDAHTNT VWKFTLTEKL EHRSVKKAGI

810
EVQEIKEAEA VVGS

SEQ ID No. 48-MR-ADM 21-42
CTVQKLAHQIYQFTDKDKDNVA

SEQ ID No. 49-MR-ADM 27-39
AHQIYQFTDKDKD
```

| SEQUENCE LISTING |
|---|

```
<160> NUMBER OF SEQ ID NOS: 49

<210> SEQ ID NO 1
<211> LENGTH: 8
<212> TYPE: PRT
<213> ORGANISM: Homo sapiens

<400> SEQUENCE: 1

Gly Tyr Thr Phe Ser Arg Tyr Trp
1               5

<210> SEQ ID NO 2
<211> LENGTH: 8
<212> TYPE: PRT
<213> ORGANISM: Homo sapiens
```

```
<400> SEQUENCE: 2

Ile Leu Pro Gly Ser Gly Ser Thr
1               5

<210> SEQ ID NO 3
<211> LENGTH: 11
<212> TYPE: PRT
<213> ORGANISM: Homo sapiens

<400> SEQUENCE: 3

Thr Glu Gly Tyr Glu Tyr Asp Gly Phe Asp Tyr
1               5                   10

<210> SEQ ID NO 4
<211> LENGTH: 11
<212> TYPE: PRT
<213> ORGANISM: Homo sapiens

<400> SEQUENCE: 4

Gln Ser Ile Val Tyr Ser Asn Gly Asn Thr Tyr
1               5                   10

<210> SEQ ID NO 5
<211> LENGTH: 9
<212> TYPE: PRT
<213> ORGANISM: Homo sapiens

<400> SEQUENCE: 5

Phe Gln Gly Ser His Ile Pro Tyr Thr
1               5

<210> SEQ ID NO 6
<211> LENGTH: 219
<212> TYPE: PRT
<213> ORGANISM: Homo sapiens

<400> SEQUENCE: 6

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

Ser Ser Gly Leu Tyr Ser Leu Ser Ser Val Val Thr Val Pro Ser Ser
          180                 185                 190

Ser Leu Gly Thr Gln Thr Tyr Ile Cys Asn Val Asn His Lys Pro Ser
      195                 200                 205

Asn Thr Lys Val Asp Lys Arg Val Glu Pro Lys
    210                 215

<210> SEQ ID NO 7
<211> LENGTH: 219
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
          20                  25                  30

Trp Ile Ser Trp Val Arg Gln Ala Pro Gly Gln Gly Leu Glu Trp Met
      35                  40                  45

Gly Arg Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
              100                 105                 110

Thr Val Thr Val Ser Ser Ala Ser Thr Lys Gly Pro Ser Val Phe Pro
          115                 120                 125

Leu Ala Pro Ser Ser Lys Ser Thr Ser Gly Gly Thr Ala Ala Leu Gly
      130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
          180                 185                 190

Ser Leu Gly Thr Gln Thr Tyr Ile Cys Asn Val Asn His Lys Pro Ser
      195                 200                 205

Asn Thr Lys Val Asp Lys Arg Val Glu Pro Lys
    210                 215

<210> SEQ ID NO 8
<211> LENGTH: 219
<212> TYPE: PRT
<213> ORGANISM: Homo sapiens

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
          20                  25                  30

Trp Ile Glu Trp Val Arg Gln Ala Pro Gly Gln Gly Leu Glu Trp Met
      35                  40                  45

Gly Arg Ile Leu Pro Gly Ser Gly Ser Thr Asn Tyr Ala Gln Lys Phe
    50                  55                  60

-continued

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys
    210                 215
```

```
<210> SEQ ID NO 9
<211> LENGTH: 219
<212> TYPE: PRT
<213> ORGANISM: Homo sapiens

<400> SEQUENCE: 9
```

```
Gln Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Ser Arg Tyr
                20                  25                  30

Trp Ile Ser Trp Val Arg Gln Ala Pro Gly Gln Gly Leu Glu Trp Met
            35                  40                  45

Gly Glu Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys
    210                 215
```

```
<210> SEQ ID NO 10
<211> LENGTH: 219
<212> TYPE: PRT
<213> ORGANISM: Homo sapiens

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Ser Arg Tyr
                20                  25                  30

Trp Ile Glu Trp Val Arg Gln Ala Pro Gly Gln Gly Leu Glu Trp Met
            35                  40                  45

Gly Glu Ile Leu Pro Gly Ser Gly Ser Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys
    210                 215

<210> SEQ ID NO 11
<211> LENGTH: 219
<212> TYPE: PRT
<213> ORGANISM: Homo sapiens

<400> SEQUENCE: 11

Asp Val Leu Leu Ser Gln Thr Pro Leu Ser Leu Pro Val Ser Leu Gly
1               5                   10                  15

Asp Gln Ala Thr Ile Ser Cys Arg Ser Ser Gln Ser Ile Val Tyr Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Tyr Thr Phe Gly Gly Gly Thr Lys Leu Glu Ile Lys
            100                 105                 110
```

-continued

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 12
<211> LENGTH: 219
<212> TYPE: PRT
<213> ORGANISM: Homo sapiens

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Ser
                20                  25                  30

Asn Gly Asn Thr Tyr Leu Asn Trp Phe Gln Gln Arg Pro Gly Gln Ser
        35                  40                  45

Pro Arg Arg Leu Ile Tyr Arg Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 13
<211> LENGTH: 219
<212> TYPE: PRT
<213> ORGANISM: Homo sapiens

<400> SEQUENCE: 13
```

-continued

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Arg Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

```
<210> SEQ ID NO 14
<211> LENGTH: 21
<212> TYPE: PRT
<213> ORGANISM: Homo sapiens

<400> SEQUENCE: 14

Tyr Arg Gln Ser Met Asn Asn Phe Gln Gly Leu Arg Ser Phe Gly Cys
1               5                   10                  15

Arg Phe Gly Thr Cys
            20
```

```
<210> SEQ ID NO 15
<211> LENGTH: 12
<212> TYPE: PRT
<213> ORGANISM: Homo sapiens

<400> SEQUENCE: 15

Cys Thr Val Gln Lys Leu Ala His Gln Ile Tyr Gln
1               5                   10
```

```
<210> SEQ ID NO 16
<211> LENGTH: 12
<212> TYPE: PRT
<213> ORGANISM: Homo sapiens

<400> SEQUENCE: 16

Cys Ala Pro Arg Ser Lys Ile Ser Pro Gln Gly Tyr
1               5                   10
```

<210> SEQ ID NO 17
<211> LENGTH: 19
<212> TYPE: PRT
<213> ORGANISM: Mus musculus

<400> SEQUENCE: 17

Tyr Arg Gln Ser Met Asn Gln Gly Ser Arg Ser Asn Gly Cys Arg Phe
1               5                   10                  15

Gly Thr Cys

<210> SEQ ID NO 18
<211> LENGTH: 12
<212> TYPE: PRT
<213> ORGANISM: Mus musculus

<400> SEQUENCE: 18

Cys Thr Phe Gln Lys Leu Ala His Gln Ile Tyr Gln
1               5                   10

<210> SEQ ID NO 19
<211> LENGTH: 12
<212> TYPE: PRT
<213> ORGANISM: Mus musculus

<400> SEQUENCE: 19

Cys Ala Pro Arg Asn Lys Ile Ser Pro Gln Gly Tyr
1               5                   10

<210> SEQ ID NO 20
<211> LENGTH: 52
<212> TYPE: PRT
<213> ORGANISM: Homo sapiens

<400> SEQUENCE: 20

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
        50

<210> SEQ ID NO 21
<211> LENGTH: 53
<212> TYPE: PRT
<213> ORGANISM: Homo sapiens

<400> SEQUENCE: 21

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr Gly
        50

<210> SEQ ID NO 22
<211> LENGTH: 50
<212> TYPE: PRT

-continued

```
<213> ORGANISM: Mus musculus

<400> SEQUENCE: 22

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu Thr
            20                  25                  30

Asp Lys Asp Lys Asp Gly Met Ala Pro Arg Asn Lys Ile Ser Pro Gln
        35                  40                  45

Gly Tyr
    50

<210> SEQ ID NO 23
<211> LENGTH: 42
<212> TYPE: PRT
<213> ORGANISM: Homo sapiens

<400> SEQUENCE: 23

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala
        35                  40

<210> SEQ ID NO 24
<211> LENGTH: 10
<212> TYPE: PRT
<213> ORGANISM: Homo sapiens

<400> SEQUENCE: 24

Pro Arg Ser Lys Ile Ser Pro Gln Gly Tyr
1               5                   10

<210> SEQ ID NO 25
<211> LENGTH: 14
<212> TYPE: PRT
<213> ORGANISM: Homo sapiens

<400> SEQUENCE: 25

Tyr Arg Gln Ser Met Asn Asn Phe Gln Gly Leu Arg Ser Phe
1               5                   10

<210> SEQ ID NO 26
<211> LENGTH: 10
<212> TYPE: PRT
<213> ORGANISM: Homo sapiens

<400> SEQUENCE: 26

Tyr Arg Gln Ser Met Asn Asn Phe Gln Gly
1               5                   10

<210> SEQ ID NO 27
<211> LENGTH: 6
<212> TYPE: PRT
<213> ORGANISM: Homo sapiens

<400> SEQUENCE: 27

Tyr Arg Gln Ser Met Asn
1               5

<210> SEQ ID NO 28
```

```
<211> LENGTH: 32
<212> TYPE: PRT
<213> ORGANISM: Homo sapiens

<400> SEQUENCE: 28

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

<210> SEQ ID NO 29
<211> LENGTH: 40
<212> TYPE: PRT
<213> ORGANISM: Mus musculus

<400> SEQUENCE: 29

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu Thr
            20                  25                  30

Asp Lys Asp Lys Asp Gly Met Ala
        35                  40

<210> SEQ ID NO 30
<211> LENGTH: 31
<212> TYPE: PRT
<213> ORGANISM: Mus musculus

<400> SEQUENCE: 30

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu
            20                  25                  30

<210> SEQ ID NO 31
<211> LENGTH: 164
<212> TYPE: PRT
<213> ORGANISM: Homo sapiens

<400> SEQUENCE: 31

Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
            20                  25                  30

Thr Gly Leu Ala Asp Val Lys Ala Gly Pro Ala Gln Thr Leu Ile Arg
        35                  40                  45

Pro Gln Asp Met Lys Gly Ala Ser Arg Ser Pro Glu Asp Ser Ser Pro
    50                  55                  60

Asp Ala Ala Arg Ile Arg Val Lys Arg Tyr Arg Gln Ser Met Asn Asn
65                  70                  75                  80

Phe Gln Gly Leu Arg Ser Phe Gly Cys Arg Phe Gly Thr Cys Thr Val
                85                  90                  95

Gln Lys Leu Ala His Gln Ile Tyr Gln Phe Thr Asp Lys Asp Lys Asp
                100                 105                 110

Asn Val Ala Pro Arg Ser Lys Ile Ser Pro Gln Gly Tyr Gly Arg Arg
            115                 120                 125

Arg Arg Arg Ser Leu Pro Glu Ala Gly Pro Gly Arg Thr Leu Val Ser
        130                 135                 140

Ser Lys Pro Gln Ala His Gly Ala Pro Ala Pro Pro Ser Gly Ser Ala
```

-continued

```
145              150              155              160
Pro His Phe Leu

<210> SEQ ID NO 32
<211> LENGTH: 20
<212> TYPE: PRT
<213> ORGANISM: Homo sapiens

<400> SEQUENCE: 32

Ala Arg Leu Asp Val Ala Ser Glu Phe Arg Lys Lys Trp Asn Lys Trp
1               5                   10                  15

Ala Leu Ser Arg
            20

<210> SEQ ID NO 33
<211> LENGTH: 48
<212> TYPE: PRT
<213> ORGANISM: Homo sapiens

<400> SEQUENCE: 33

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
                20                  25                  30

Ser Arg Ser Pro Glu Asp Ser Ser Pro Asp Ala Ala Arg Ile Arg Val
            35                  40                  45

<210> SEQ ID NO 34
<211> LENGTH: 38
<212> TYPE: PRT
<213> ORGANISM: Homo sapiens

<400> SEQUENCE: 34

Arg Arg Arg Arg Arg Ser Leu Pro Glu Ala Gly Pro Gly Arg Thr Leu
1               5                   10                  15

Val Ser Ser Lys Pro Gln Ala His Gly Ala Pro Ala Pro Pro Ser Gly
                20                  25                  30

Ser Ala Pro His Phe Leu
            35

<210> SEQ ID NO 35
<211> LENGTH: 448
<212> TYPE: PRT
<213> ORGANISM: Homo sapiens

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
                20                  25                  30

Trp Ile Glu Trp Val Arg Gln Ala Pro Gly Gln Gly Leu Glu Trp Ile
            35                  40                  45

Gly Glu Ile Leu Pro Gly Ser Gly Ser Thr Asn Tyr Asn Gln Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
```

-continued

```
              100            105            110
Thr Val Thr Val Ser Ser Ala Ser Thr Lys Gly Pro Ser Val Phe Pro
         115            120            125

Leu Ala Pro Ser Ser Lys Ser Thr Ser Gly Gly Thr Ala Ala Leu Gly
    130            135            140

Cys Leu Val Lys Asp Tyr Phe Pro Glu Pro Val Thr Val Ser Trp Asn
145            150            155            160

Ser Gly Ala Leu Thr Ser Gly Val His Thr Phe Pro Ala Val Leu Gln
             165            170            175

Ser Ser Gly Leu Tyr Ser Leu Ser Ser Val Val Thr Val Pro Ser Ser
         180            185            190

Ser Leu Gly Thr Gln Thr Tyr Ile Cys Asn Val Asn His Lys Pro Ser
         195            200            205

Asn Thr Lys Val Asp Lys Lys Val Glu Pro Lys Ser Cys Asp Lys Thr
    210            215            220

His Thr Cys Pro Pro Cys Pro Ala Pro Glu Leu Leu Gly Gly Pro Ser
225            230            235            240

Val Phe Leu Phe Pro Pro Lys Pro Lys Asp Thr Leu Met Ile Ser Arg
             245            250            255

Thr Pro Glu Val Thr Cys Val Val Val Asp Val Ser His Glu Asp Pro
         260            265            270

Glu Val Lys Phe Asn Trp Tyr Val Asp Gly Val Glu Val His Asn Ala
         275            280            285

Lys Thr Lys Pro Arg Glu Glu Gln Tyr Asn Ser Thr Tyr Arg Val Val
    290            295            300

Ser Val Leu Thr Val Leu His Gln Asp Trp Leu Asn Gly Lys Glu Tyr
305            310            315            320

Lys Cys Lys Val Ser Asn Lys Ala Leu Pro Ala Pro Ile Glu Lys Thr
             325            330            335

Ile Ser Lys Ala Lys Gly Gln Pro Arg Glu Pro Gln Val Tyr Thr Leu
         340            345            350

Pro Pro Ser Arg Asp Glu Leu Thr Lys Asn Gln Val Ser Leu Thr Cys
         355            360            365

Leu Val Lys Gly Phe Tyr Pro Ser Asp Ile Ala Val Glu Trp Glu Ser
    370            375            380

Asn Gly Gln Pro Glu Asn Asn Tyr Lys Thr Thr Pro Pro Val Leu Asp
385            390            395            400

Ser Asp Gly Ser Phe Phe Leu Tyr Ser Lys Leu Thr Val Asp Lys Ser
             405            410            415

Arg Trp Gln Gln Gly Asn Val Phe Ser Cys Ser Val Met His Glu Ala
             420            425            430

Leu His Asn His Tyr Thr Gln Lys Ser Leu Ser Leu Ser Pro Gly Lys
         435            440            445
```

```
<210> SEQ ID NO 36
<211> LENGTH: 219
<212> TYPE: PRT
<213> ORGANISM: Homo sapiens

<400> SEQUENCE: 36

Asp Val Val Leu Thr Gln Ser Pro Leu Ser Leu Pro Val Thr Leu Gly
1               5              10              15

Gln Pro Ala Ser Ile Ser Cys Arg Ser Ser Gln Ser Ile Val Tyr Ser
         20              25              30
```

-continued

Asn Gly Asn Thr Tyr Leu Glu Trp Tyr Leu Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 37
<211> LENGTH: 118
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser
        115

<210> SEQ ID NO 38
<211> LENGTH: 118
<212> TYPE: PRT
<213> ORGANISM: Homo sapiens

<400> SEQUENCE: 38

Gln Val Gln Leu Gln Gln Ser Gly Ala Glu Leu Met Lys Pro Gly Ala
1               5                   10                  15

```
Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Leu Thr Val Ser Ser
        115

<210> SEQ ID NO 39
<211> LENGTH: 973
<212> TYPE: PRT
<213> ORGANISM: Homo sapiens

<400> SEQUENCE: 39

Met Ala Gly Arg Val Pro Ser Leu Leu Val Leu Leu Val Phe Pro Ser
1               5                   10                  15

Ser Cys Leu Ala Phe Arg Ser Pro Leu Ser Val Phe Lys Arg Phe Lys
            20                  25                  30

Glu Thr Thr Arg Pro Phe Ser Asn Glu Cys Leu Gly Thr Thr Arg Pro
        35                  40                  45

Val Val Pro Ile Asp Ser Ser Asp Phe Ala Leu Asp Ile Arg Met Pro
    50                  55                  60

Gly Val Thr Pro Lys Gln Ser Asp Thr Tyr Phe Cys Met Ser Met Arg
65                  70                  75                  80

Ile Pro Val Asp Glu Glu Ala Phe Val Ile Asp Phe Lys Pro Arg Ala
                85                  90                  95

Ser Met Asp Thr Val His His Met Leu Leu Phe Gly Cys Asn Met Pro
            100                 105                 110

Ser Ser Thr Gly Ser Tyr Trp Phe Cys Asp Glu Gly Thr Cys Thr Asp
        115                 120                 125

Lys Ala Asn Ile Leu Tyr Ala Trp Ala Arg Asn Ala Pro Pro Thr Arg
    130                 135                 140

Leu Pro Lys Gly Val Gly Phe Arg Val Gly Gly Glu Thr Gly Ser Lys
145                 150                 155                 160

Tyr Phe Val Leu Gln Val His Tyr Gly Asp Ile Ser Ala Phe Arg Asp
                165                 170                 175

Asn Asn Lys Asp Cys Ser Gly Val Ser Leu His Leu Thr Arg Leu Pro
            180                 185                 190

Gln Pro Leu Ile Ala Gly Met Tyr Leu Met Met Ser Val Asp Thr Val
        195                 200                 205

Ile Pro Ala Gly Glu Lys Val Val Asn Ser Asp Ile Ser Cys His Tyr
    210                 215                 220

Lys Asn Tyr Pro Met His Val Phe Ala Tyr Arg Val His Thr His His
225                 230                 235                 240

Leu Gly Lys Val Val Ser Gly Tyr Arg Val Arg Asn Gly Gln Trp Thr
                245                 250                 255

Leu Ile Gly Arg Gln Ser Pro Gln Leu Pro Gln Ala Phe Tyr Pro Val
            260                 265                 270
```

```
Gly His Pro Val Asp Val Ser Phe Gly Asp Leu Leu Ala Ala Arg Cys
        275             280             285

Val Phe Thr Gly Glu Gly Arg Thr Glu Ala Thr His Ile Gly Gly Thr
    290             295             300

Ser Ser Asp Glu Met Cys Asn Leu Tyr Ile Met Tyr Tyr Met Glu Ala
305             310             315             320

Lys His Ala Val Ser Phe Met Thr Cys Thr Gln Asn Val Ala Pro Asp
            325             330             335

Met Phe Arg Thr Ile Pro Pro Glu Ala Asn Ile Pro Ile Pro Val Lys
            340             345             350

Ser Asp Met Val Met Met His Glu His His Lys Glu Thr Glu Tyr Lys
            355             360             365

Asp Lys Ile Pro Leu Leu Gln Gln Pro Lys Arg Glu Glu Glu Glu Val
    370             375             380

Leu Asp Gln Gly Asp Phe Tyr Ser Leu Leu Ser Lys Leu Leu Gly Glu
385             390             395             400

Arg Glu Asp Val Val His Val His Lys Tyr Asn Pro Thr Glu Lys Ala
            405             410             415

Glu Ser Glu Ser Asp Leu Val Ala Glu Ile Ala Asn Val Val Gln Lys
            420             425             430

Lys Asp Leu Gly Arg Ser Asp Ala Arg Glu Gly Ala Glu His Glu Arg
            435             440             445

Gly Asn Ala Ile Leu Val Arg Asp Arg Ile His Lys Phe His Arg Leu
    450             455             460

Val Ser Thr Leu Arg Pro Pro Glu Ser Arg Val Phe Ser Leu Gln Gln
465             470             475             480

Pro Pro Pro Gly Glu Gly Thr Trp Glu Pro Glu His Thr Gly Asp Phe
            485             490             495

His Met Glu Glu Ala Leu Asp Trp Pro Gly Val Tyr Leu Leu Pro Gly
            500             505             510

Gln Val Ser Gly Val Ala Leu Asp Pro Lys Asn Asn Leu Val Ile Phe
            515             520             525

His Arg Gly Asp His Val Trp Asp Gly Asn Ser Phe Asp Ser Lys Phe
    530             535             540

Val Tyr Gln Gln Ile Gly Leu Gly Pro Ile Glu Glu Asp Thr Ile Leu
545             550             555             560

Val Ile Asp Pro Asn Asn Ala Ala Val Leu Gln Ser Ser Gly Lys Asn
            565             570             575

Leu Phe Tyr Leu Pro His Gly Leu Ser Ile Asp Lys Asp Gly Asn Tyr
            580             585             590

Trp Val Thr Asp Val Ala Leu His Gln Val Phe Lys Leu Asp Pro Asn
            595             600             605

Asn Lys Glu Gly Pro Val Leu Ile Leu Gly Arg Ser Met Gln Pro Gly
    610             615             620

Ser Asp Gln Asn His Phe Cys Gln Pro Thr Asp Val Ala Val Asp Pro
625             630             635             640

Gly Thr Gly Ala Ile Tyr Val Ser Asp Gly Tyr Cys Asn Ser Arg Ile
            645             650             655

Val Gln Phe Ser Pro Ser Gly Lys Phe Ile Thr Gln Trp Gly Glu Glu
            660             665             670

Ser Ser Gly Ser Ser Pro Leu Pro Gly Gln Phe Thr Val Pro His Ser
            675             680             685
```

```
Leu Ala Leu Val Pro Leu Leu Gly Gln Leu Cys Val Ala Asp Arg Glu
    690             695             700

Asn Gly Arg Ile Gln Cys Phe Lys Thr Asp Thr Lys Glu Phe Val Arg
705             710             715             720

Glu Ile Lys His Ser Ser Phe Gly Arg Asn Val Phe Ala Ile Ser Tyr
            725             730             735

Ile Pro Gly Leu Leu Phe Ala Val Asn Gly Lys Pro His Phe Gly Asp
            740             745             750

Gln Glu Pro Val Gln Gly Phe Val Met Asn Phe Ser Asn Gly Glu Ile
            755             760             765

Ile Asp Ile Phe Lys Pro Val Arg Lys His Phe Asp Met Pro His Asp
    770             775             780

Ile Val Ala Ser Glu Asp Gly Thr Val Tyr Ile Gly Asp Ala His Thr
785             790             795             800

Asn Thr Val Trp Lys Phe Thr Leu Thr Glu Lys Leu Glu His Arg Ser
            805             810             815

Val Lys Lys Ala Gly Ile Glu Val Gln Glu Ile Lys Glu Ala Glu Ala
            820             825             830

Val Val Glu Thr Lys Met Glu Asn Lys Pro Thr Ser Ser Glu Leu Gln
            835             840             845

Lys Met Gln Glu Lys Gln Lys Leu Ile Lys Glu Pro Gly Ser Gly Val
    850             855             860

Pro Val Val Leu Ile Thr Thr Leu Leu Val Ile Pro Val Val Val Leu
865             870             875             880

Leu Ala Ile Ala Ile Phe Ile Arg Trp Lys Lys Ser Arg Ala Phe Gly
            885             890             895

Asp Ser Glu His Lys Leu Glu Thr Ser Ser Gly Arg Val Leu Gly Arg
            900             905             910

Phe Arg Gly Lys Gly Ser Gly Gly Leu Asn Leu Gly Asn Phe Phe Ala
            915             920             925

Ser Arg Lys Gly Tyr Ser Arg Lys Gly Phe Asp Arg Leu Ser Thr Glu
    930             935             940

Gly Ser Asp Gln Glu Lys Glu Asp Asp Gly Ser Glu Ser Glu Glu Glu
945             950             955             960

Tyr Ser Ala Pro Leu Pro Ala Leu Ala Pro Ser Ser Ser
            965             970
```

```
<210> SEQ ID NO 40
<211> LENGTH: 866
<212> TYPE: PRT
<213> ORGANISM: Homo sapiens

<400> SEQUENCE: 40
```

```
Met Ala Gly Arg Val Pro Ser Leu Leu Val Leu Leu Val Phe Pro Ser
1               5               10              15

Ser Cys Leu Ala Phe Arg Ser Pro Leu Ser Val Phe Lys Arg Phe Lys
            20              25              30

Glu Thr Thr Arg Pro Phe Ser Asn Glu Cys Leu Gly Thr Thr Arg Pro
            35              40              45

Val Val Pro Ile Asp Ser Ser Asp Phe Ala Leu Asp Ile Arg Met Pro
    50              55              60

Gly Val Thr Pro Lys Gln Ser Asp Thr Tyr Phe Cys Met Ser Met Arg
65              70              75              80

Ile Pro Val Asp Glu Glu Ala Phe Val Ile Asp Phe Lys Pro Arg Ala
            85              90              95
```

-continued

```
Ser Met Asp Thr Val His His Met Leu Leu Phe Gly Cys Asn Met Pro
            100             105             110

Ser Ser Thr Gly Ser Tyr Trp Phe Cys Asp Glu Gly Thr Cys Thr Asp
            115             120             125

Lys Ala Asn Ile Leu Tyr Ala Trp Ala Arg Asn Ala Pro Pro Thr Arg
            130             135             140

Leu Pro Lys Gly Val Gly Phe Arg Val Gly Gly Glu Thr Gly Ser Lys
145             150             155             160

Tyr Phe Val Leu Gln Val His Tyr Gly Asp Ile Ser Ala Phe Arg Asp
                165             170             175

Asn Asn Lys Asp Cys Ser Gly Val Ser Leu His Leu Thr Arg Leu Pro
            180             185             190

Gln Pro Leu Ile Ala Gly Met Tyr Leu Met Met Ser Val Asp Thr Val
            195             200             205

Ile Pro Ala Gly Glu Lys Val Val Asn Ser Asp Ile Ser Cys His Tyr
    210             215             220

Lys Asn Tyr Pro Met His Val Phe Ala Tyr Arg Val His Thr His His
225             230             235             240

Leu Gly Lys Val Val Ser Gly Tyr Arg Val Arg Asn Gly Gln Trp Thr
                245             250             255

Leu Ile Gly Arg Gln Ser Pro Gln Leu Pro Gln Ala Phe Tyr Pro Val
                260             265             270

Gly His Pro Val Asp Val Ser Phe Gly Asp Leu Leu Ala Ala Arg Cys
            275             280             285

Val Phe Thr Gly Glu Gly Arg Thr Glu Ala Thr His Ile Gly Gly Thr
    290             295             300

Ser Ser Asp Glu Met Cys Asn Leu Tyr Ile Met Tyr Tyr Met Glu Ala
305             310             315             320

Lys His Ala Val Ser Phe Met Thr Cys Thr Gln Asn Val Ala Pro Asp
            325             330             335

Met Phe Arg Thr Ile Pro Pro Glu Ala Asn Ile Pro Ile Pro Val Lys
            340             345             350

Ser Asp Met Val Met Met His Glu His His Lys Glu Thr Glu Tyr Lys
            355             360             365

Asp Lys Ile Pro Leu Leu Gln Gln Pro Lys Arg Glu Glu Glu Glu Val
    370             375             380

Leu Asp Gln Asp Phe His Met Glu Glu Ala Leu Asp Trp Pro Gly Val
385             390             395             400

Tyr Leu Leu Pro Gly Gln Val Ser Gly Val Ala Leu Asp Pro Lys Asn
                405             410             415

Asn Leu Val Ile Phe His Arg Gly Asp His Val Trp Asp Gly Asn Ser
            420             425             430

Phe Asp Ser Lys Phe Val Tyr Gln Gln Ile Gly Leu Gly Pro Ile Glu
            435             440             445

Glu Asp Thr Ile Leu Val Ile Asp Pro Asn Asn Ala Ala Val Leu Gln
    450             455             460

Ser Ser Gly Lys Asn Leu Phe Tyr Leu Pro His Gly Leu Ser Ile Asp
465             470             475             480

Lys Asp Gly Asn Tyr Trp Val Thr Asp Val Ala Leu His Gln Val Phe
                485             490             495

Lys Leu Asp Pro Asn Asn Lys Glu Gly Pro Val Leu Ile Leu Gly Arg
            500             505             510
```

```
Ser Met Gln Pro Gly Ser Asp Gln Asn His Phe Cys Gln Pro Thr Asp
        515                 520                 525

Val Ala Val Asp Pro Gly Thr Gly Ala Ile Tyr Val Ser Asp Gly Tyr
        530                 535                 540

Cys Asn Ser Arg Ile Val Gln Phe Ser Pro Ser Gly Lys Phe Ile Thr
545                 550                 555                 560

Gln Trp Gly Glu Glu Ser Ser Gly Ser Ser Pro Leu Pro Gly Gln Phe
                565                 570                 575

Thr Val Pro His Ser Leu Ala Leu Val Pro Leu Leu Gly Gln Leu Cys
            580                 585                 590

Val Ala Asp Arg Glu Asn Gly Arg Ile Gln Cys Phe Lys Thr Asp Thr
            595                 600                 605

Lys Glu Phe Val Arg Glu Ile Lys His Ser Ser Phe Gly Arg Asn Val
        610                 615                 620

Phe Ala Ile Ser Tyr Ile Pro Gly Leu Leu Phe Ala Val Asn Gly Lys
625                 630                 635                 640

Pro His Phe Gly Asp Gln Glu Pro Val Gln Gly Phe Val Met Asn Phe
                645                 650                 655

Ser Asn Gly Glu Ile Ile Asp Ile Phe Lys Pro Val Arg Lys His Phe
                660                 665                 670

Asp Met Pro His Asp Ile Val Ala Ser Glu Asp Gly Thr Val Tyr Ile
        675                 680                 685

Gly Asp Ala His Thr Asn Thr Val Trp Lys Phe Thr Leu Thr Glu Lys
        690                 695                 700

Leu Glu His Arg Ser Val Lys Lys Ala Gly Ile Glu Val Gln Glu Ile
705                 710                 715                 720

Lys Glu Ala Glu Ala Val Val Glu Thr Lys Met Glu Asn Lys Pro Thr
                725                 730                 735

Ser Ser Glu Leu Gln Lys Met Gln Glu Lys Gln Lys Leu Ile Lys Glu
                740                 745                 750

Pro Gly Ser Gly Val Pro Val Val Leu Ile Thr Thr Leu Leu Val Ile
        755                 760                 765

Pro Val Val Val Leu Leu Ala Ile Ala Ile Phe Ile Arg Trp Lys Lys
        770                 775                 780

Ser Arg Ala Phe Gly Asp Ser Glu His Lys Leu Glu Thr Ser Ser Gly
785                 790                 795                 800

Arg Val Leu Gly Arg Phe Arg Gly Lys Gly Ser Gly Gly Leu Asn Leu
                805                 810                 815

Gly Asn Phe Phe Ala Ser Arg Lys Gly Tyr Ser Arg Lys Gly Phe Asp
                820                 825                 830

Arg Leu Ser Thr Glu Gly Ser Asp Gln Glu Lys Glu Asp Asp Gly Ser
            835                 840                 845

Glu Ser Glu Glu Glu Tyr Ser Ala Pro Leu Pro Ala Leu Ala Pro Ser
        850                 855                 860

Ser Ser
865

<210> SEQ ID NO 41
<211> LENGTH: 905
<212> TYPE: PRT
<213> ORGANISM: Homo sapiens

<400> SEQUENCE: 41

Met Ala Gly Arg Val Pro Ser Leu Leu Val Leu Leu Val Phe Pro Ser
1                   5                   10                  15
```

-continued

```
Ser Cys Leu Ala Phe Arg Ser Pro Leu Ser Val Phe Lys Arg Phe Lys
        20              25              30

Glu Thr Thr Arg Pro Phe Ser Asn Glu Cys Leu Gly Thr Thr Arg Pro
        35              40              45

Val Val Pro Ile Asp Ser Ser Asp Phe Ala Leu Asp Ile Arg Met Pro
    50              55              60

Gly Val Thr Pro Lys Gln Ser Asp Thr Tyr Phe Cys Met Ser Met Arg
65              70              75              80

Ile Pro Val Asp Glu Glu Ala Phe Val Ile Asp Phe Lys Pro Arg Ala
                85              90              95

Ser Met Asp Thr Val His His Met Leu Leu Phe Gly Cys Asn Met Pro
            100             105             110

Ser Ser Thr Gly Ser Tyr Trp Phe Cys Asp Glu Gly Thr Cys Thr Asp
            115             120             125

Lys Ala Asn Ile Leu Tyr Ala Trp Ala Arg Asn Ala Pro Pro Thr Arg
    130             135             140

Leu Pro Lys Gly Val Gly Phe Arg Val Gly Gly Glu Thr Gly Ser Lys
145             150             155             160

Tyr Phe Val Leu Gln Val His Tyr Gly Asp Ile Ser Ala Phe Arg Asp
                165             170             175

Asn Asn Lys Asp Cys Ser Gly Val Ser Leu His Leu Thr Arg Leu Pro
            180             185             190

Gln Pro Leu Ile Ala Gly Met Tyr Leu Met Met Ser Val Asp Thr Val
            195             200             205

Ile Pro Ala Gly Glu Lys Val Val Asn Ser Asp Ile Ser Cys His Tyr
    210             215             220

Lys Asn Tyr Pro Met His Val Phe Ala Tyr Arg Val His Thr His His
225             230             235             240

Leu Gly Lys Val Val Ser Gly Tyr Arg Val Arg Asn Gly Gln Trp Thr
            245             250             255

Leu Ile Gly Arg Gln Ser Pro Gln Leu Pro Gln Ala Phe Tyr Pro Val
            260             265             270

Gly His Pro Val Asp Val Ser Phe Gly Asp Leu Leu Ala Ala Arg Cys
            275             280             285

Val Phe Thr Gly Glu Gly Arg Thr Glu Ala Thr His Ile Gly Gly Thr
    290             295             300

Ser Ser Asp Glu Met Cys Asn Leu Tyr Ile Met Tyr Tyr Met Glu Ala
305             310             315             320

Lys His Ala Val Ser Phe Met Thr Cys Thr Gln Asn Val Ala Pro Asp
            325             330             335

Met Phe Arg Thr Ile Pro Pro Glu Ala Asn Ile Pro Ile Pro Val Lys
            340             345             350

Ser Asp Met Val Met Met His Glu His His Lys Glu Thr Glu Tyr Lys
            355             360             365

Asp Lys Ile Pro Leu Leu Gln Gln Pro Lys Arg Glu Glu Glu Glu Val
    370             375             380

Leu Asp Gln Gly Asp Phe Tyr Ser Leu Leu Ser Lys Leu Leu Gly Glu
385             390             395             400

Arg Glu Asp Val Val His Val His Lys Tyr Asn Pro Thr Glu Lys Ala
                405             410             415

Glu Ser Glu Ser Asp Leu Val Ala Glu Ile Ala Asn Val Val Gln Lys
            420             425             430
```

```
Lys Asp Leu Gly Arg Ser Asp Ala Arg Glu Gly Ala Glu His Glu Arg
        435                 440                 445

Gly Asn Ala Ile Leu Val Arg Asp Arg Ile His Lys Phe His Arg Leu
        450                 455                 460

Val Ser Thr Leu Arg Pro Pro Glu Ser Arg Val Phe Ser Leu Gln Gln
465                 470                 475                 480

Pro Pro Pro Gly Glu Gly Thr Trp Glu Pro Glu His Thr Gly Asp Phe
                485                 490                 495

His Met Glu Glu Ala Leu Asp Trp Pro Gly Val Tyr Leu Leu Pro Gly
                500                 505                 510

Gln Val Ser Gly Val Ala Leu Asp Pro Lys Asn Asn Leu Val Ile Phe
        515                 520                 525

His Arg Gly Asp His Val Trp Asp Gly Asn Ser Phe Asp Ser Lys Phe
        530                 535                 540

Val Tyr Gln Gln Ile Gly Leu Gly Pro Ile Glu Glu Asp Thr Ile Leu
545                 550                 555                 560

Val Ile Asp Pro Asn Asn Ala Ala Val Leu Gln Ser Ser Gly Lys Asn
                565                 570                 575

Leu Phe Tyr Leu Pro His Gly Leu Ser Ile Asp Lys Asp Gly Asn Tyr
                580                 585                 590

Trp Val Thr Asp Val Ala Leu His Gln Val Phe Lys Leu Asp Pro Asn
        595                 600                 605

Asn Lys Glu Gly Pro Val Leu Ile Leu Gly Arg Ser Met Gln Pro Gly
        610                 615                 620

Ser Asp Gln Asn His Phe Cys Gln Pro Thr Asp Val Ala Val Asp Pro
625                 630                 635                 640

Gly Thr Gly Ala Ile Tyr Val Ser Asp Gly Tyr Cys Asn Ser Arg Ile
                645                 650                 655

Val Gln Phe Ser Pro Ser Gly Lys Phe Ile Thr Gln Trp Gly Glu Glu
                660                 665                 670

Ser Ser Gly Ser Ser Pro Leu Pro Gly Gln Phe Thr Val Pro His Ser
        675                 680                 685

Leu Ala Leu Val Pro Leu Leu Gly Gln Leu Cys Val Ala Asp Arg Glu
        690                 695                 700

Asn Gly Arg Ile Gln Cys Phe Lys Thr Asp Thr Lys Glu Phe Val Arg
705                 710                 715                 720

Glu Ile Lys His Ser Ser Phe Gly Arg Asn Val Phe Ala Ile Ser Tyr
                725                 730                 735

Ile Pro Gly Leu Leu Phe Ala Val Asn Gly Lys Pro His Phe Gly Asp
                740                 745                 750

Gln Glu Pro Val Gln Gly Phe Val Met Asn Phe Ser Asn Gly Glu Ile
        755                 760                 765

Ile Asp Ile Phe Lys Pro Val Arg Lys His Phe Asp Met Pro His Asp
        770                 775                 780

Ile Val Ala Ser Glu Asp Gly Thr Val Tyr Ile Gly Asp Ala His Thr
785                 790                 795                 800

Asn Thr Val Trp Lys Phe Thr Leu Thr Glu Lys Leu Glu His Arg Ser
                805                 810                 815

Val Lys Lys Ala Gly Ile Glu Val Gln Glu Ile Lys Asp Ser Glu His
                820                 825                 830

Lys Leu Glu Thr Ser Ser Gly Arg Val Leu Gly Arg Phe Arg Gly Lys
        835                 840                 845

Gly Ser Gly Gly Leu Asn Leu Gly Asn Phe Phe Ala Ser Arg Lys Gly
```

```
          850                    855                    860

Tyr Ser Arg Lys Gly Phe Asp Arg Leu Ser Thr Glu Gly Ser Asp Gln
865                    870                    875                    880

Glu Lys Glu Asp Asp Gly Ser Glu Ser Glu Glu Glu Tyr Ser Ala Pro
                    885                    890                    895

Leu Pro Ala Leu Ala Pro Ser Ser Ser
                    900                    905

<210> SEQ ID NO 42
<211> LENGTH: 887
<212> TYPE: PRT
<213> ORGANISM: Homo sapiens

<400> SEQUENCE: 42

Met Ala Gly Arg Val Pro Ser Leu Leu Val Leu Leu Val Phe Pro Ser
1                    5                    10                    15

Ser Cys Leu Ala Phe Arg Ser Pro Leu Ser Val Phe Lys Arg Phe Lys
                    20                    25                    30

Glu Thr Thr Arg Pro Phe Ser Asn Glu Cys Leu Gly Thr Thr Arg Pro
                    35                    40                    45

Val Val Pro Ile Asp Ser Ser Asp Phe Ala Leu Asp Ile Arg Met Pro
          50                    55                    60

Gly Val Thr Pro Lys Gln Ser Asp Thr Tyr Phe Cys Met Ser Met Arg
65                    70                    75                    80

Ile Pro Val Asp Glu Glu Ala Phe Val Ile Asp Phe Lys Pro Arg Ala
                    85                    90                    95

Ser Met Asp Thr Val His His Met Leu Leu Phe Gly Cys Asn Met Pro
                    100                    105                    110

Ser Ser Thr Gly Ser Tyr Trp Phe Cys Asp Glu Gly Thr Cys Thr Asp
                    115                    120                    125

Lys Ala Asn Ile Leu Tyr Ala Trp Ala Arg Asn Ala Pro Pro Thr Arg
          130                    135                    140

Leu Pro Lys Gly Val Gly Phe Arg Val Gly Gly Glu Thr Gly Ser Lys
145                    150                    155                    160

Tyr Phe Val Leu Gln Val His Tyr Gly Asp Ile Ser Ala Phe Arg Asp
                    165                    170                    175

Asn Asn Lys Asp Cys Ser Gly Val Ser Leu His Leu Thr Arg Leu Pro
                    180                    185                    190

Gln Pro Leu Ile Ala Gly Met Tyr Leu Met Met Ser Val Asp Thr Val
                    195                    200                    205

Ile Pro Ala Gly Glu Lys Val Val Asn Ser Asp Ile Ser Cys His Tyr
          210                    215                    220

Lys Asn Tyr Pro Met His Val Phe Ala Tyr Arg Val His Thr His His
225                    230                    235                    240

Leu Gly Lys Val Val Ser Gly Tyr Arg Val Arg Asn Gly Gln Trp Thr
                    245                    250                    255

Leu Ile Gly Arg Gln Ser Pro Gln Leu Pro Gln Ala Phe Tyr Pro Val
                    260                    265                    270

Gly His Pro Val Asp Val Ser Phe Gly Asp Leu Leu Ala Ala Arg Cys
                    275                    280                    285

Val Phe Thr Gly Glu Gly Arg Thr Glu Ala Thr His Ile Gly Gly Thr
          290                    295                    300

Ser Ser Asp Glu Met Cys Asn Leu Tyr Ile Met Tyr Tyr Met Glu Ala
305                    310                    315                    320
```

```
Lys His Ala Val Ser Phe Met Thr Cys Thr Gln Asn Val Ala Pro Asp
            325                 330                 335

Met Phe Arg Thr Ile Pro Pro Glu Ala Asn Ile Pro Ile Pro Val Lys
            340                 345                 350

Ser Asp Met Val Met Met His Glu His His Lys Glu Thr Glu Tyr Lys
            355                 360                 365

Asp Lys Ile Pro Leu Leu Gln Gln Pro Lys Arg Glu Glu Glu Glu Val
        370                 375                 380

Leu Asp Gln Gly Asp Phe Tyr Ser Leu Leu Ser Lys Leu Leu Gly Glu
    385                 390                 395                 400

Arg Glu Asp Val Val His Val His Lys Tyr Asn Pro Thr Glu Lys Ala
                405                 410                 415

Glu Ser Glu Ser Asp Leu Val Ala Glu Ile Ala Asn Val Val Gln Lys
            420                 425                 430

Lys Asp Leu Gly Arg Ser Asp Ala Arg Glu Gly Ala Glu His Glu Arg
            435                 440                 445

Gly Asn Ala Ile Leu Val Arg Asp Arg Ile His Lys Phe His Arg Leu
        450                 455                 460

Val Ser Thr Leu Arg Pro Pro Glu Ser Arg Val Phe Ser Leu Gln Gln
    465                 470                 475                 480

Pro Pro Pro Gly Glu Gly Thr Trp Glu Pro Glu His Thr Gly Asp Phe
                485                 490                 495

His Met Glu Glu Ala Leu Asp Trp Pro Gly Val Tyr Leu Leu Pro Gly
            500                 505                 510

Gln Val Ser Gly Val Ala Leu Asp Pro Lys Asn Asn Leu Val Ile Phe
            515                 520                 525

His Arg Gly Asp His Val Trp Asp Gly Asn Ser Phe Asp Ser Lys Phe
        530                 535                 540

Val Tyr Gln Gln Ile Gly Leu Gly Pro Ile Glu Glu Asp Thr Ile Leu
    545                 550                 555                 560

Val Ile Asp Pro Asn Asn Ala Ala Val Leu Gln Ser Ser Gly Lys Asn
                565                 570                 575

Leu Phe Tyr Leu Pro His Gly Leu Ser Ile Asp Lys Asp Gly Asn Tyr
            580                 585                 590

Trp Val Thr Asp Val Ala Leu His Gln Val Phe Lys Leu Asp Pro Asn
            595                 600                 605

Asn Lys Glu Gly Pro Val Leu Ile Leu Gly Arg Ser Met Gln Pro Gly
        610                 615                 620

Ser Asp Gln Asn His Phe Cys Gln Pro Thr Asp Val Ala Val Asp Pro
    625                 630                 635                 640

Gly Thr Gly Ala Ile Tyr Val Ser Asp Gly Tyr Cys Asn Ser Arg Ile
                645                 650                 655

Val Gln Phe Ser Pro Ser Gly Lys Phe Ile Thr Gln Trp Gly Glu Glu
            660                 665                 670

Ser Ser Gly Ser Ser Pro Leu Pro Gly Gln Phe Thr Val Pro His Ser
            675                 680                 685

Leu Ala Leu Val Pro Leu Leu Gly Gln Leu Cys Val Ala Asp Arg Glu
        690                 695                 700

Asn Gly Arg Ile Gln Cys Phe Lys Thr Asp Thr Lys Glu Phe Val Arg
    705                 710                 715                 720

Glu Ile Lys His Ser Ser Phe Gly Arg Asn Val Phe Ala Ile Ser Tyr
                725                 730                 735

Ile Pro Gly Leu Leu Phe Ala Val Asn Gly Lys Pro His Phe Gly Asp
```

```
                740                 745                 750

Gln Glu Pro Val Gln Gly Phe Val Met Asn Phe Ser Asn Gly Glu Ile
                755                 760                 765

Ile Asp Ile Phe Lys Pro Val Arg Lys His Phe Asp Met Pro His Asp
                770                 775                 780

Ile Val Ala Ser Glu Asp Gly Thr Val Tyr Ile Gly Asp Ala His Thr
785                 790                 795                 800

Asn Thr Val Trp Lys Phe Thr Leu Thr Glu Lys Leu Glu His Arg Ser
                805                 810                 815

Val Lys Lys Ala Gly Ile Glu Val Gln Glu Ile Lys Gly Lys Gly Ser
                820                 825                 830

Gly Gly Leu Asn Leu Gly Asn Phe Phe Ala Ser Arg Lys Gly Tyr Ser
                835                 840                 845

Arg Lys Gly Phe Asp Arg Leu Ser Thr Glu Gly Ser Asp Gln Glu Lys
                850                 855                 860

Glu Asp Asp Gly Ser Glu Ser Glu Glu Glu Tyr Ser Ala Pro Leu Pro
865                 870                 875                 880

Ala Leu Ala Pro Ser Ser Ser
                885

<210> SEQ ID NO 43
<211> LENGTH: 974
<212> TYPE: PRT
<213> ORGANISM: Homo sapiens

<400> SEQUENCE: 43

Met Ala Gly Arg Val Pro Ser Leu Leu Val Leu Leu Val Phe Pro Ser
1                   5                   10                  15

Ser Cys Leu Ala Phe Arg Ser Pro Leu Ser Val Phe Lys Arg Phe Lys
                20                  25                  30

Glu Thr Thr Arg Pro Phe Ser Asn Glu Cys Leu Gly Thr Thr Arg Pro
                35                  40                  45

Val Val Pro Ile Asp Ser Ser Asp Phe Ala Leu Asp Ile Arg Met Pro
                50                  55                  60

Gly Val Thr Pro Lys Gln Ser Asp Thr Tyr Phe Cys Met Ser Met Arg
65                  70                  75                  80

Ile Pro Val Asp Glu Glu Ala Phe Val Ile Asp Phe Lys Pro Arg Ala
                85                  90                  95

Ser Met Asp Thr Val His His Met Leu Leu Phe Gly Cys Asn Met Pro
                100                 105                 110

Ser Ser Thr Gly Ser Tyr Trp Phe Cys Asp Glu Gly Thr Cys Thr Asp
                115                 120                 125

Lys Ala Asn Ile Leu Tyr Ala Trp Ala Arg Asn Ala Pro Pro Thr Arg
                130                 135                 140

Leu Pro Lys Gly Val Gly Phe Arg Val Gly Gly Glu Thr Gly Ser Lys
145                 150                 155                 160

Tyr Phe Val Leu Gln Val His Tyr Gly Asp Ile Ser Ala Phe Arg Asp
                165                 170                 175

Asn Asn Lys Asp Cys Ser Gly Val Ser Leu His Leu Thr Arg Leu Pro
                180                 185                 190

Gln Pro Leu Ile Ala Gly Met Tyr Leu Met Met Ser Val Asp Thr Val
                195                 200                 205

Ile Pro Ala Gly Glu Lys Val Val Asn Ser Asp Ile Ser Cys His Tyr
                210                 215                 220
```

-continued

```
Lys Asn Tyr Pro Met His Val Phe Ala Tyr Arg Val His Thr His His
225             230             235             240

Leu Gly Lys Val Val Ser Gly Tyr Arg Val Arg Asn Gly Gln Trp Thr
            245             250             255

Leu Ile Gly Arg Gln Ser Pro Gln Leu Pro Gln Ala Phe Tyr Pro Val
            260             265             270

Gly His Pro Val Asp Val Ser Phe Gly Asp Leu Leu Ala Ala Arg Cys
            275             280             285

Val Phe Thr Gly Glu Gly Arg Thr Glu Ala Thr His Ile Gly Gly Thr
    290             295             300

Ser Ser Asp Glu Met Cys Asn Leu Tyr Ile Met Tyr Tyr Met Glu Ala
305             310             315             320

Lys His Ala Val Ser Phe Met Thr Cys Thr Gln Asn Val Ala Pro Asp
            325             330             335

Met Phe Arg Thr Ile Pro Pro Glu Ala Asn Ile Pro Ile Pro Val Lys
            340             345             350

Ser Asp Met Val Met Met His Glu His His Lys Glu Thr Glu Tyr Lys
            355             360             365

Asp Lys Ile Pro Leu Leu Gln Gln Pro Lys Arg Glu Glu Gly Glu Val
    370             375             380

Leu Asp Gln Gly Asp Phe Tyr Ser Leu Leu Ser Lys Leu Leu Gly Glu
385             390             395             400

Arg Glu Asp Val Val His Val His Lys Tyr Asn Pro Thr Glu Lys Ala
            405             410             415

Glu Ser Glu Ser Asp Leu Val Ala Glu Ile Ala Asn Val Val Gln Lys
            420             425             430

Lys Asp Leu Gly Arg Ser Asp Ala Arg Glu Gly Ala Glu His Glu Arg
            435             440             445

Gly Asn Ala Ile Leu Val Arg Asp Arg Ile His Lys Phe His Arg Leu
    450             455             460

Val Ser Thr Leu Arg Pro Pro Glu Ser Arg Val Phe Ser Leu Gln Gln
465             470             475             480

Pro Pro Pro Gly Glu Gly Thr Trp Glu Pro Glu His Thr Gly Asp Phe
            485             490             495

His Met Glu Glu Ala Leu Asp Trp Pro Gly Val Tyr Leu Leu Pro Gly
            500             505             510

Gln Val Ser Gly Val Ala Leu Asp Pro Lys Asn Asn Leu Val Ile Phe
            515             520             525

His Arg Gly Asp His Val Trp Asp Gly Asn Ser Phe Asp Ser Lys Phe
    530             535             540

Val Tyr Gln Gln Ile Gly Leu Gly Pro Ile Glu Glu Asp Thr Ile Leu
545             550             555             560

Val Ile Asp Pro Asn Asn Ala Ala Val Leu Gln Ser Ser Gly Lys Asn
            565             570             575

Leu Phe Tyr Leu Pro His Gly Leu Ser Ile Asp Lys Asp Gly Asn Tyr
            580             585             590

Trp Val Thr Asp Val Ala Leu His Gln Val Phe Lys Leu Asp Pro Asn
            595             600             605

Asn Lys Glu Gly Pro Val Leu Ile Leu Gly Arg Ser Met Gln Pro Gly
    610             615             620

Ser Asp Gln Asn His Phe Cys Gln Pro Thr Asp Val Ala Val Asp Pro
625             630             635             640

Gly Thr Gly Ala Ile Tyr Val Ser Asp Gly Tyr Cys Asn Ser Arg Ile
```

-continued

```
                   645               650               655

Val Gln Phe Ser Pro Ser Gly Lys Phe Ile Thr Gln Trp Gly Glu Glu
            660               665               670

Ser Ser Gly Ser Ser Pro Leu Pro Gly Gln Phe Thr Val Pro His Ser
            675               680               685

Leu Ala Leu Val Pro Leu Leu Gly Gln Leu Cys Val Ala Asp Arg Glu
        690               695               700

Asn Gly Arg Ile Gln Cys Phe Lys Thr Asp Thr Lys Glu Phe Val Arg
705               710               715               720

Glu Ile Lys His Ser Ser Phe Gly Arg Asn Val Phe Ala Ile Ser Tyr
                725               730               735

Ile Pro Gly Leu Leu Phe Ala Val Asn Gly Lys Pro His Phe Gly Asp
            740               745               750

Gln Glu Pro Val Gln Gly Phe Val Met Asn Phe Ser Asn Gly Glu Ile
            755               760               765

Ile Asp Ile Phe Lys Pro Val Arg Lys His Phe Asp Met Pro His Asp
        770               775               780

Ile Val Ala Ser Glu Asp Gly Thr Val Tyr Ile Gly Asp Ala His Thr
785               790               795               800

Asn Thr Val Trp Lys Phe Thr Leu Thr Glu Lys Leu Glu His Arg Ser
                805               810               815

Val Lys Lys Ala Gly Ile Glu Val Gln Glu Ile Lys Glu Ala Glu Ala
            820               825               830

Val Val Glu Thr Lys Met Glu Asn Lys Pro Thr Ser Ser Glu Leu Gln
            835               840               845

Lys Met Gln Glu Lys Gln Lys Leu Ile Lys Glu Pro Gly Ser Gly Val
        850               855               860

Pro Val Val Leu Ile Thr Thr Leu Leu Val Ile Pro Val Val Val Leu
865               870               875               880

Leu Ala Ile Ala Ile Phe Ile Arg Trp Lys Lys Ser Arg Ala Phe Gly
                885               890               895

Ala Asp Ser Glu His Lys Leu Glu Thr Ser Ser Gly Arg Val Leu Gly
            900               905               910

Arg Phe Arg Gly Lys Gly Ser Gly Gly Leu Asn Leu Gly Asn Phe Phe
            915               920               925

Ala Ser Arg Lys Gly Tyr Ser Arg Lys Gly Phe Asp Arg Leu Ser Thr
        930               935               940

Glu Gly Ser Asp Gln Glu Lys Glu Asp Asp Gly Ser Glu Ser Glu Glu
945               950               955               960

Glu Tyr Ser Ala Pro Leu Pro Ala Leu Ala Pro Ser Ser Ser
                965               970
```

<210> SEQ ID NO 44
<211> LENGTH: 955
<212> TYPE: PRT
<213> ORGANISM: Homo sapiens

<400> SEQUENCE: 44

```
Met Ala Gly Arg Val Pro Ser Leu Leu Val Leu Leu Val Phe Pro Ser
1               5               10              15

Ser Cys Leu Ala Phe Arg Ser Pro Leu Ser Val Phe Lys Arg Phe Lys
            20              25              30

Glu Thr Thr Arg Pro Phe Ser Asn Glu Cys Leu Gly Thr Thr Arg Pro
        35              40              45
```

-continued

```
Val Val Pro Ile Asp Ser Ser Asp Phe Ala Leu Asp Ile Arg Met Pro
    50              55                  60

Gly Val Thr Pro Lys Gln Ser Asp Thr Tyr Phe Cys Met Ser Met Arg
65              70                  75                  80

Ile Pro Val Asp Glu Glu Ala Phe Val Ile Asp Phe Lys Pro Arg Ala
                85                  90                  95

Ser Met Asp Thr Val His His Met Leu Leu Phe Gly Cys Asn Met Pro
            100             105                 110

Ser Ser Thr Gly Ser Tyr Trp Phe Cys Asp Glu Gly Thr Cys Thr Asp
            115             120                 125

Lys Ala Asn Ile Leu Tyr Ala Trp Ala Arg Asn Ala Pro Pro Thr Arg
    130             135                 140

Leu Pro Lys Gly Val Gly Phe Arg Val Gly Gly Glu Thr Gly Ser Lys
145             150                 155                 160

Tyr Phe Val Leu Gln Val His Tyr Gly Asp Ile Ser Ala Phe Arg Asp
                165                 170                 175

Asn Asn Lys Asp Cys Ser Gly Val Ser Leu His Leu Thr Arg Leu Pro
            180             185                 190

Gln Pro Leu Ile Ala Gly Met Tyr Leu Met Met Ser Val Asp Thr Val
            195             200                 205

Ile Pro Ala Gly Glu Lys Val Val Asn Ser Asp Ile Ser Cys His Tyr
    210             215                 220

Lys Asn Tyr Pro Met His Val Phe Ala Tyr Arg Val His Thr His His
225             230                 235                 240

Leu Gly Lys Val Val Ser Gly Tyr Arg Val Arg Asn Gly Gln Trp Thr
            245             250                 255

Leu Ile Gly Arg Gln Ser Pro Gln Leu Pro Gln Ala Phe Tyr Pro Val
            260             265                 270

Gly His Pro Val Asp Val Ser Phe Gly Asp Leu Leu Ala Ala Arg Cys
            275             280                 285

Val Phe Thr Gly Glu Gly Arg Thr Glu Ala Thr His Ile Gly Gly Thr
    290             295                 300

Ser Ser Asp Glu Met Cys Asn Leu Tyr Ile Met Tyr Tyr Met Glu Ala
305             310                 315                 320

Lys His Ala Val Ser Phe Met Thr Cys Thr Gln Asn Val Ala Pro Asp
            325             330                 335

Met Phe Arg Thr Ile Pro Pro Glu Ala Asn Ile Pro Ile Pro Val Lys
            340             345                 350

Ser Asp Met Val Met Met His Glu His His Lys Glu Thr Glu Tyr Lys
            355             360                 365

Asp Lys Ile Pro Leu Leu Gln Gln Pro Lys Arg Glu Glu Glu Glu Val
    370             375                 380

Leu Asp Gln Gly Asp Phe Tyr Ser Leu Leu Ser Lys Leu Leu Gly Glu
385             390                 395                 400

Arg Glu Asp Val Val His Val His Lys Tyr Asn Pro Thr Glu Lys Ala
                405                 410                 415

Glu Ser Glu Ser Asp Leu Val Ala Glu Ile Ala Asn Val Val Gln Lys
            420             425                 430

Lys Asp Leu Gly Arg Ser Asp Ala Arg Glu Gly Ala Glu His Glu Arg
            435             440                 445

Gly Asn Ala Ile Leu Val Arg Asp Arg Ile His Lys Phe His Arg Leu
    450             455                 460

Val Ser Thr Leu Arg Pro Pro Glu Ser Arg Val Phe Ser Leu Gln Gln
```

```
465                    470                    475                    480
Pro Pro Pro Gly Glu Gly Thr Trp Glu Pro Glu His Thr Gly Asp Phe
            485              490              495

His Met Glu Glu Ala Leu Asp Trp Pro Gly Val Tyr Leu Leu Pro Gly
            500              505              510

Gln Val Ser Gly Val Ala Leu Asp Pro Lys Asn Asn Leu Val Ile Phe
            515              520              525

His Arg Gly Asp His Val Trp Asp Gly Asn Ser Phe Asp Ser Lys Phe
            530              535              540

Val Tyr Gln Gln Ile Gly Leu Gly Pro Ile Glu Glu Asp Thr Ile Leu
545              550              555              560

Val Ile Asp Pro Asn Asn Ala Ala Val Leu Gln Ser Ser Gly Lys Asn
            565              570              575

Leu Phe Tyr Leu Pro His Gly Leu Ser Ile Asp Lys Asp Gly Asn Tyr
            580              585              590

Trp Val Thr Asp Val Ala Leu His Gln Val Phe Lys Leu Asp Pro Asn
            595              600              605

Asn Lys Glu Gly Pro Val Leu Ile Leu Gly Arg Ser Met Gln Pro Gly
            610              615              620

Ser Asp Gln Asn His Phe Cys Gln Pro Thr Asp Val Ala Val Asp Pro
625              630              635              640

Gly Thr Gly Ala Ile Tyr Val Ser Asp Gly Tyr Cys Asn Ser Arg Ile
            645              650              655

Val Gln Phe Ser Pro Ser Gly Lys Phe Ile Thr Gln Trp Gly Glu Glu
            660              665              670

Ser Ser Gly Ser Ser Pro Leu Pro Gly Gln Phe Thr Val Pro His Ser
            675              680              685

Leu Ala Leu Val Pro Leu Leu Gly Gln Leu Cys Val Ala Asp Arg Glu
            690              695              700

Asn Gly Arg Ile Gln Cys Phe Lys Thr Asp Thr Lys Glu Phe Val Arg
705              710              715              720

Glu Ile Lys His Ser Ser Phe Gly Arg Asn Val Phe Ala Ile Ser Tyr
            725              730              735

Ile Pro Gly Leu Leu Phe Ala Val Asn Gly Lys Pro His Phe Gly Asp
            740              745              750

Gln Glu Pro Val Gln Gly Phe Val Met Asn Phe Ser Asn Gly Glu Ile
            755              760              765

Ile Asp Ile Phe Lys Pro Val Arg Lys His Phe Asp Met Pro His Asp
            770              775              780

Ile Val Ala Ser Glu Asp Gly Thr Val Tyr Ile Gly Asp Ala His Thr
785              790              795              800

Asn Thr Val Trp Lys Phe Thr Leu Thr Glu Lys Leu Glu His Arg Ser
            805              810              815

Val Lys Lys Ala Gly Ile Glu Val Gln Glu Ile Lys Glu Ala Glu Ala
            820              825              830

Val Val Glu Thr Lys Met Glu Asn Lys Pro Thr Ser Ser Glu Leu Gln
            835              840              845

Lys Met Gln Glu Lys Gln Lys Leu Ile Lys Glu Pro Gly Ser Gly Val
            850              855              860

Pro Val Val Leu Ile Thr Thr Leu Leu Val Ile Pro Val Val Val Leu
865              870              875              880

Leu Ala Ile Ala Ile Phe Ile Arg Trp Lys Lys Ser Arg Ala Phe Gly
            885              890              895
```

```
Gly Lys Gly Ser Gly Gly Leu Asn Leu Gly Asn Phe Phe Ala Ser Arg
        900                 905                 910

Lys Gly Tyr Ser Arg Lys Gly Phe Asp Arg Leu Ser Thr Glu Gly Ser
        915                 920                 925

Asp Gln Glu Lys Glu Asp Asp Gly Ser Glu Ser Glu Glu Glu Tyr Ser
    930                 935                 940

Ala Pro Leu Pro Ala Leu Ala Pro Ser Ser Ser
945                 950                 955
```

```
<210> SEQ ID NO 45
<211> LENGTH: 464
<212> TYPE: PRT
<213> ORGANISM: Homo sapiens

<400> SEQUENCE: 45
```

```
Phe Lys Glu Thr Thr Arg Pro Phe Ser Asn Glu Cys Leu Gly Thr Thr
1               5                   10                  15

Arg Pro Val Val Pro Ile Asp Ser Ser Asp Phe Ala Leu Asp Ile Arg
            20                  25                  30

Met Pro Gly Val Thr Pro Lys Gln Ser Asp Thr Tyr Phe Cys Met Ser
        35                  40                  45

Met Arg Ile Pro Val Asp Glu Glu Ala Phe Val Ile Asp Phe Lys Pro
    50                  55                  60

Arg Ala Ser Met Asp Thr Val His His Met Leu Leu Phe Gly Cys Asn
65                  70                  75                  80

Met Pro Ser Ser Thr Gly Ser Tyr Trp Phe Cys Asp Glu Gly Thr Cys
                85                  90                  95

Thr Asp Lys Ala Asn Ile Leu Tyr Ala Trp Ala Arg Asn Ala Pro Pro
            100                 105                 110

Thr Arg Leu Pro Lys Gly Val Gly Phe Arg Val Gly Gly Glu Thr Gly
        115                 120                 125

Ser Lys Tyr Phe Val Leu Gln Val His Tyr Gly Asp Ile Ser Ala Phe
    130                 135                 140

Arg Asp Asn Asn Lys Asp Cys Ser Gly Val Ser Leu His Leu Thr Arg
145                 150                 155                 160

Leu Pro Gln Pro Leu Ile Ala Gly Met Tyr Leu Met Met Ser Val Asp
            165                 170                 175

Thr Val Ile Pro Ala Gly Glu Lys Val Val Asn Ser Asp Ile Ser Cys
            180                 185                 190

His Tyr Lys Asn Tyr Pro Met His Val Phe Ala Tyr Arg Val His Thr
        195                 200                 205

His His Leu Gly Lys Val Val Ser Gly Tyr Arg Val Arg Asn Gly Gln
    210                 215                 220

Trp Thr Leu Ile Gly Arg Gln Ser Pro Gln Leu Pro Gln Ala Phe Tyr
225                 230                 235                 240

Pro Val Gly His Pro Val Asp Val Ser Phe Gly Asp Leu Leu Ala Ala
            245                 250                 255

Arg Cys Val Phe Thr Gly Glu Gly Arg Thr Glu Ala Thr His Ile Gly
            260                 265                 270

Gly Thr Ser Ser Asp Glu Met Cys Asn Leu Tyr Ile Met Tyr Tyr Met
        275                 280                 285

Glu Ala Lys His Ala Val Ser Phe Met Thr Cys Thr Gln Asn Val Ala
    290                 295                 300

Pro Asp Met Phe Arg Thr Ile Pro Pro Glu Ala Asn Ile Pro Ile Pro
```

-continued

```
305                 310                 315                 320

Val Lys Ser Asp Met Val Met Met His Glu His His Lys Glu Thr Glu
                325                 330                 335

Tyr Lys Asp Lys Ile Pro Leu Leu Gln Gln Pro Lys Arg Glu Glu Glu
                340                 345                 350

Glu Val Leu Asp Gln Gly Asp Phe Tyr Ser Leu Leu Ser Lys Leu Leu
                355                 360                 365

Gly Glu Arg Glu Asp Val Val His Val His Lys Tyr Asn Pro Thr Glu
            370                 375                 380

Lys Ala Glu Ser Glu Ser Asp Leu Val Ala Glu Ile Ala Asn Val Val
385                 390                 395                 400

Gln Lys Lys Asp Leu Gly Arg Ser Asp Ala Arg Glu Gly Ala Glu His
                405                 410                 415

Glu Arg Gly Asn Ala Ile Leu Val Arg Asp Arg Ile His Lys Phe His
                420                 425                 430

Arg Leu Val Ser Thr Leu Arg Pro Pro Glu Ser Arg Val Phe Ser Leu
                435                 440                 445

Gln Gln Pro Pro Pro Gly Glu Gly Thr Trp Glu Pro Glu His Thr Gly
                450                 455                 460

<210> SEQ ID NO 46
<211> LENGTH: 323
<212> TYPE: PRT
<213> ORGANISM: Homo sapiens

<400> SEQUENCE: 46

Asp Phe His Met Glu Glu Ala Leu Asp Trp Pro Gly Val Tyr Leu Leu
1               5                   10                  15

Pro Gly Gln Val Ser Gly Val Ala Leu Asp Pro Lys Asn Asn Leu Val
                20                  25                  30

Ile Phe His Arg Gly Asp His Val Trp Asp Gly Asn Ser Phe Asp Ser
            35                  40                  45

Lys Phe Val Tyr Gln Gln Ile Gly Leu Gly Pro Ile Glu Glu Asp Thr
        50                  55                  60

Ile Leu Val Ile Asp Pro Asn Asn Ala Ala Val Leu Gln Ser Ser Gly
65                  70                  75                  80

Lys Asn Leu Phe Tyr Leu Pro His Gly Leu Ser Ile Asp Lys Asp Gly
                85                  90                  95

Asn Tyr Trp Val Thr Asp Val Ala Leu His Gln Val Phe Lys Leu Asp
                100                 105                 110

Pro Asn Asn Lys Glu Gly Pro Val Leu Ile Leu Gly Arg Ser Met Gln
            115                 120                 125

Pro Gly Ser Asp Gln Asn His Phe Cys Gln Pro Thr Asp Val Ala Val
        130                 135                 140

Asp Pro Gly Thr Gly Ala Ile Tyr Val Ser Asp Gly Tyr Cys Asn Ser
145                 150                 155                 160

Arg Ile Val Gln Phe Ser Pro Ser Gly Lys Phe Ile Thr Gln Trp Gly
                165                 170                 175

Glu Glu Ser Ser Gly Ser Ser Pro Leu Pro Gly Gln Phe Thr Val Pro
            180                 185                 190

His Ser Leu Ala Leu Val Pro Leu Leu Gly Gln Leu Cys Val Ala Asp
            195                 200                 205

Arg Glu Asn Gly Arg Ile Gln Cys Phe Lys Thr Asp Thr Lys Glu Phe
        210                 215                 220
```

```
Val Arg Glu Ile Lys His Ser Ser Phe Gly Arg Asn Val Phe Ala Ile
225             230             235             240

Ser Tyr Ile Pro Gly Leu Leu Phe Ala Val Asn Gly Lys Pro His Phe
            245             250             255

Gly Asp Gln Glu Pro Val Gln Gly Phe Val Met Asn Phe Ser Asn Gly
            260             265             270

Glu Ile Ile Asp Ile Phe Lys Pro Val Arg Lys His Phe Asp Met Pro
        275             280             285

His Asp Ile Val Ala Ser Glu Asp Gly Thr Val Tyr Ile Gly Asp Ala
    290             295             300

His Thr Asn Thr Val Trp Lys Phe Thr Leu Thr Glu Lys Leu Glu His
305             310             315             320

Arg Ser Val

<210> SEQ ID NO 47
<211> LENGTH: 814
<212> TYPE: PRT
<213> ORGANISM: Homo sapiens

<400> SEQUENCE: 47

Ser Pro Leu Ser Val Phe Lys Arg Phe Lys Glu Thr Thr Arg Pro Phe
1               5               10              15

Ser Asn Glu Cys Leu Gly Thr Thr Arg Pro Val Val Pro Ile Asp Ser
            20              25              30

Ser Asp Phe Ala Leu Asp Ile Arg Met Pro Gly Val Thr Pro Lys Gln
            35              40              45

Ser Asp Thr Tyr Phe Cys Met Ser Met Arg Ile Pro Val Asp Glu Glu
        50              55              60

Ala Phe Val Ile Asp Phe Lys Pro Arg Ala Ser Met Asp Thr Val His
65              70              75              80

His Met Leu Leu Phe Gly Cys Asn Met Pro Ser Ser Thr Gly Ser Tyr
            85              90              95

Trp Phe Cys Asp Glu Gly Thr Cys Thr Asp Lys Ala Asn Ile Leu Tyr
            100             105             110

Ala Trp Ala Arg Asn Ala Pro Pro Thr Arg Leu Pro Lys Gly Val Gly
        115             120             125

Phe Arg Val Gly Gly Glu Thr Gly Ser Lys Tyr Phe Val Leu Gln Val
    130             135             140

His Tyr Gly Asp Ile Ser Ala Phe Arg Asp Asn Asn Lys Asp Cys Ser
145             150             155             160

Gly Val Ser Leu His Leu Thr Arg Leu Pro Gln Pro Leu Ile Ala Gly
            165             170             175

Met Tyr Leu Met Met Ser Val Asp Thr Val Ile Pro Ala Gly Glu Lys
            180             185             190

Val Val Asn Ser Asp Ile Ser Cys His Tyr Lys Asn Tyr Pro Met His
        195             200             205

Val Phe Ala Tyr Arg Val His Thr His His Leu Gly Lys Val Val Ser
    210             215             220

Gly Tyr Arg Val Arg Asn Gly Gln Trp Thr Leu Ile Gly Arg Gln Ser
225             230             235             240

Pro Gln Leu Pro Gln Ala Phe Tyr Pro Val Gly His Pro Val Asp Val
            245             250             255

Ser Phe Gly Asp Leu Leu Ala Ala Arg Cys Val Phe Thr Gly Glu Gly
            260             265             270
```

-continued

```
Arg Thr Glu Ala Thr His Ile Gly Gly Thr Ser Ser Asp Glu Met Cys
        275                 280                 285

Asn Leu Tyr Ile Met Tyr Tyr Met Glu Ala Lys His Ala Val Ser Phe
        290                 295                 300

Met Thr Cys Thr Gln Asn Val Ala Pro Asp Met Phe Arg Thr Ile Pro
305                 310                 315                 320

Pro Glu Ala Asn Ile Pro Ile Pro Val Lys Ser Asp Met Val Met Met
                325                 330                 335

His Glu His His Lys Glu Thr Glu Tyr Lys Asp Lys Ile Pro Leu Leu
                340                 345                 350

Gln Gln Pro Lys Arg Glu Glu Glu Val Leu Asp Gln Gly Asp Phe
        355                 360                 365

Tyr Ser Leu Leu Ser Lys Leu Leu Gly Glu Arg Glu Asp Val Val His
        370                 375                 380

Val His Lys Tyr Asn Pro Thr Glu Lys Ala Glu Ser Glu Ser Asp Leu
385                 390                 395                 400

Val Ala Glu Ile Ala Asn Val Val Gln Lys Lys Asp Leu Gly Arg Ser
                405                 410                 415

Asp Ala Arg Glu Gly Ala Glu His Glu Arg Gly Asn Ala Ile Leu Val
                420                 425                 430

Arg Asp Arg Ile His Lys Phe His Arg Leu Val Ser Thr Leu Arg Pro
        435                 440                 445

Pro Glu Ser Arg Val Phe Ser Leu Gln Gln Pro Pro Pro Gly Glu Gly
        450                 455                 460

Thr Trp Glu Pro Glu His Thr Gly Asp Phe His Met Glu Glu Ala Leu
465                 470                 475                 480

Asp Trp Pro Gly Val Tyr Leu Leu Pro Gly Gln Val Ser Gly Val Ala
                485                 490                 495

Leu Asp Pro Lys Asn Asn Leu Val Ile Phe His Arg Gly Asp His Val
                500                 505                 510

Trp Asp Gly Asn Ser Phe Asp Ser Lys Phe Val Tyr Gln Gln Ile Gly
        515                 520                 525

Leu Gly Pro Ile Glu Glu Asp Thr Ile Leu Val Ile Asp Pro Asn Asn
        530                 535                 540

Ala Ala Val Leu Gln Ser Ser Gly Lys Asn Leu Phe Tyr Leu Pro His
545                 550                 555                 560

Gly Leu Ser Ile Asp Lys Asp Gly Asn Tyr Trp Val Thr Asp Val Ala
                565                 570                 575

Leu His Gln Val Phe Lys Leu Asp Pro Asn Asn Lys Glu Gly Pro Val
                580                 585                 590

Leu Ile Leu Gly Arg Ser Met Gln Pro Gly Ser Asp Gln Asn His Phe
        595                 600                 605

Cys Gln Pro Thr Asp Val Ala Val Asp Pro Gly Thr Gly Ala Ile Tyr
        610                 615                 620

Val Ser Asp Gly Tyr Cys Asn Ser Arg Ile Val Gln Phe Ser Pro Ser
625                 630                 635                 640

Gly Lys Phe Ile Thr Gln Trp Gly Glu Glu Ser Ser Gly Ser Ser Pro
                645                 650                 655

Leu Pro Gly Gln Phe Thr Val Pro His Ser Leu Ala Leu Val Pro Leu
        660                 665                 670

Leu Gly Gln Leu Cys Val Ala Asp Arg Glu Asn Gly Arg Ile Gln Cys
        675                 680                 685

Phe Lys Thr Asp Thr Lys Glu Phe Val Arg Glu Ile Lys His Ser Ser
```

-continued

```
          690                   695                   700

Phe Gly Arg Asn Val Phe Ala Ile Ser Tyr Ile Pro Gly Leu Leu Phe
705                   710                   715                   720

Ala Val Asn Gly Lys Pro His Phe Gly Asp Gln Glu Pro Val Gln Gly
                  725                   730                   735

Phe Val Met Asn Phe Ser Asn Gly Glu Ile Ile Asp Ile Phe Lys Pro
                  740                   745                   750

Val Arg Lys His Phe Asp Met Pro His Asp Ile Val Ala Ser Glu Asp
              755                   760                   765

Gly Thr Val Tyr Ile Gly Asp Ala His Thr Asn Thr Val Trp Lys Phe
          770                   775                   780

Thr Leu Thr Glu Lys Leu Glu His Arg Ser Val Lys Lys Ala Gly Ile
785                   790                   795                   800

Glu Val Gln Glu Ile Lys Glu Ala Glu Ala Val Val Gly Ser
                  805                   810

<210> SEQ ID NO 48
<211> LENGTH: 22
<212> TYPE: PRT
<213> ORGANISM: Homo sapiens

<400> SEQUENCE: 48

Cys Thr Val Gln Lys Leu Ala His Gln Ile Tyr Gln Phe Thr Asp Lys
1               5                   10                  15

Asp Lys Asp Asn Val Ala
            20

<210> SEQ ID NO 49
<211> LENGTH: 13
<212> TYPE: PRT
<213> ORGANISM: Homo sapiens

<400> SEQUENCE: 49

Ala His Gln Ile Tyr Gln Phe Thr Asp Lys Asp Lys Asp
1               5                   10
```

The invention claimed is:

1. A method of treatment comprising:
treating a patient that is critically ill and suffering from an acute disease or condition selected from the group consisting of: severe infections, shock, acute heart failure, myocardial infarction, stroke, and organ dysfunction by administering an anti-adrenomedullin (ADM) antibody or anti-ADM antibody fragment or anti-ADM non-Ig scaffold to said patient,
wherein said anti-adrenomedullin (ADM) antibody or anti-ADM antibody fragment or anti-ADM non-Ig scaffold is administered in an amount sufficient to result in accelerating conversion of ADM-Gly to ADM-NH$_2$ of circulating ADM-Gly in said patient,
wherein said patient has a ratio of pro-Adrenomedullin or a fragment thereof to ADM-NH$_2$ (SEQ ID No. 20) above a predetermined threshold in a sample of bodily fluid taken from said patient prior to administration of said anti-adrenomedullin (ADM) antibody or anti-ADM antibody fragment or anti-ADM non-Ig scaffold,
wherein said pro-Adrenomedullin or fragment thereof is selected from the group consisting of PAMP (SEQ ID No. 32), MR-proADM (SEQ ID No. 33), ADM-Gly (SEQ ID No. 21) and CT-proADM (SEQ ID No. 34), and wherein said anti-ADM antibody or anti-ADM fragment or anti-ADM non-Ig scaffold binds to the N-terminal and/or mid-regional part (aa 1-42) of ADM-Gly and/or ADM-NH$_2$:
YRQSMNNFQGLRSFGCRFGTCTVQKLAHQIYQ
FTDKDKDNVA (SEQ ID No. 23), and
wherein the heavy chain of said anti-adrenomedullin (ADM) antibody or anti-ADM antibody fragment or anti-ADM non-Ig scaffold comprises:

```
                                   SEQ ID No.: 1
        GYTFSRYW,

SEQ ID No.: 2
        ILPGSGST, and

SEQ ID No.: 3
        TEGYEYDGFDY
``` and wherein the light chain of said anti-adrenomedullin (ADM) antibody or anti-ADM antibody fragment or anti-ADM non-Ig scaffold comprises:

```
                              SEQ ID No.: 4
QSIVYSNGNTY,

SEQUENCE: RVS, and
                              SEQ ID No.: 5
FQGSHIPYT.
```

2. The method according to claim 1 wherein said anti-ADM antibody or anti-ADM fragment or anti-ADM non-Ig scaffold binds to the N-terminal part (amino acids 1-21) of ADM-Gly and/or ADM-NH₂: YRQSMNNFQGLRSFGCRFGTC (SEQ ID No. 14).

3. The method according to claim 1 wherein said anti-ADM antibody or anti-ADM antibody fragment or anti-ADM non-Ig scaffold recognizes and binds to the N-terminal end (amino acid 1) of ADM-Gly and/or ADM-NH₂.

4. The method according to claim 1 wherein said anti-ADM antibody or anti-ADM fragment or anti-ADM non-Ig scaffold binds to the mid-regional part (amino acids 21-42) of ADM-Gly and/or ADM-NH₂: CTVQKLAHQIYQFTDKDKDNVA (SEQ ID No. 48).

5. The method according to claim 4 wherein said anti-ADM antibody or anti-ADM fragment or anti-ADM non-Ig scaffold binds to the mid-regional part (amino acids 21-32) of ADM-Gly and/or ADM-NH₂: CTVQKLAHQIYQ (SEQ ID No.: 15).

6. The method according to claim 1 wherein said anti-ADM antibody or anti-ADM fragment or anti-ADM non-Ig scaffold binds to the mid-regional part (amino acids 21-42) of ADM-Gly and/or ADM-NH₂: CTVQKLAHQIYQFTDKDKDNVA (SEQ ID No. 48).

7. The method according to claim 6 wherein said anti-ADM antibody or anti-ADM fragment or anti-ADM non-Ig scaffold binds to the mid-regional part (amino acids 21-32) of ADM-Gly and/or ADM-NH₂: CTVQKLAHQIYQ (SEQ ID No.: 15).

8. The method according to claim 6 wherein said anti-ADM antibody or anti-ADM fragment or anti-ADM non-Ig scaffold binds to the mid-regional part (amino acids 27-39) of ADM-Gly and/or ADM-NH₂: AHQIYQFTDKDKD (SEQ ID No.: 49).

9. The method according to claim 1 wherein the sample additionally comprises a predetermined level of pro-Adrenomedullin or a fragment thereof consisting of the group of PAMP (SEQ ID No. 32), MR-proADM (SEQ ID No. 33), ADM-Gly (SEQ ID No. 21) CT-proADM (SEQ ID No. 34) and ADM-NH₂ (SEQ ID No. 20).

10. The method according to claim 1 wherein the ADM-Gly/ADM-NH₂ ratio in said sample is above 1.

11. The method of claim 10 wherein the ADM-Gly/ADM-NH₂ ratio is above 1.5.

12. The method of claim 10 wherein the ADM-Gly/ADM-NH₂ ratio is above 2.5.

13. The method according to claim 1 wherein the sample of bodily fluid of said patient is selected from the group of blood, serum, plasma, urine, cerebrospinal fluid (CSF), and saliva.

14. The method according to claim 13 wherein said sample is selected from the group comprising human citrate plasma, heparin plasma and EDTA plasma.

15. The method according to claim 1 additionally requiring measuring the ratio of pro-Adrenomedullin or a fragment thereof and ADM-NH₂ with an immunoassay, and wherein said pro-Adrenomedullin or fragment thereof is selected from the group consisting of PAMP (SEQ ID No.

32), MR-proADM (SEQ ID No. 33), ADM-Gly (SEQ ID No. 21) and CT-proADM (SEQ ID No. 34).

16. The method according to claim 15 wherein said immunoassay is a sandwich immunoassay.

17. The method of claim 16 wherein said immunoassay is a fully automated assay.

18. The method according to claim 1 wherein the immunoassay sensitivity of said assay for the detection of ADM-NH₂ is able to quantify ADM-NH₂ of healthy subjects and is <70 pg/ml.

19. The method of claim 18 wherein the assay sensitivity of said assay for the detection of ADM-NH₂ is <40 pg/ml.

20. The method of claim 18 wherein the assay sensitivity of said assay for the detection of ADM-NH₂ is <10 pg/ml.

21. The method according to claim 1 wherein the immunoassay sensitivity for ADM-Gly is 20 pg/ml.

22. The method of claim 21 wherein the assay sensitivity of said assay for ADM-Gly is 15 pg/ml.

23. The method of claim 21 wherein the assay sensitivity of said assay for ADM-Gly is 10 pg/ml.

24. The method according to claim 1 wherein the level of pro-Adrenomedullin or a fragment thereof and ADM-NH₂ (SEQ ID No. 20) is determined by using one binder to said pro-Adrenomedullin or a fragment thereof and a second binder to ADM-NH₂ (SEQ ID No. 20), and wherein said proAdrenomedullin or a fragment thereof is selected from the group consisting of PAMP (SEQ ID No. 32), MR-proADM (SEQ ID No. 33), ADM-Gly (SEQ ID No. 21) and CT-proADM (SEQ ID No. 34).

25. The method of claim 1 wherein said severe infection is selected from the group consisting of meningitis, systemic inflammatory response syndrome (SIRS), and sepsis.

26. The method of claim 1 wherein said shock is septic shock or cardiogenic shock.

27. The method of claim 1 wherein said acute heart failure is acute decompensated heart failure, or chronic heart failure with worsening signs and symptoms.

28. The method of claim 1 wherein said organ dysfunction is kidney dysfunction, liver dysfunction, heart dysfunction, or lung dysfunction.

29. A method for the therapy of a patient, comprising:

administering to said patient an anti-adrenomedullin (ADM) antibody or anti-ADM antibody fragment or anti-ADM non-Ig scaffold, wherein said anti-ADM antibody or anti-ADM fragment or anti-ADM non-Ig scaffold binds to the N-terminal and/or mid-regional part (amino acids 1-42) of ADM-Gly and/or ADM-NH₂: YRQSMNNFQGLRSFGCRFGTCTVQKLAHQIYQFT DKDKDNVA (SEQ ID No. 23), wherein the heavy chain of said anti-adrenomedullin (ADM) antibody or anti-ADM antibody fragment or anti-ADM non-Ig scaffold comprises:

```
                              SEQ ID No.: 1
GYTFSRYW,

SEQ ID No.: 2
ILPGSGST, and

SEQ ID No.: 3
TEGYEYDGFDY
``` and wherein the light chain of said anti-adrenomedullin (ADM) antibody or anti-ADM antibody fragment or anti-ADM non-Ig scaffold comprises:

```
                              SEQ ID No.: 4
QSIVYSNGNTY,

SEQUENCE: RVS, and
                                              5
                              SEQ ID No.: 5
FQGSHIPYT
``` wherein a level of peptidylglycine alpha-amidating monooxygenase (PAM) and/or its isoforms and/or fragments thereof is below a predetermined threshold in a sample of bodily fluid taken from said patient before administering an anti-adrenomedullin (ADM) antibody or anti-ADM antibody fragment or anti-ADM non-Ig scaffold, and wherein said patient is suffering from an acute disease or condition selected from the group consisting of: severe infections, shock, acute heart failure, myocardial infarction, stroke, and organ dysfunction.

30. The method according to claim 29, wherein said level of PAM and/or its isoforms and/or fragments thereof is the total concentration of PAM and/or its isoforms and/or fragments thereof having at least 12 amino acids or the activity of PAM and/or its isoforms and/or fragments thereof comprising the sequences SEQ ID No. 39, SEQ ID No. 40, SEQ ID No. 41, SEQ ID No. 42, SEQ ID No. 43, SEQ ID No. 44, SEQ ID No. 45, SEQ ID No. 46 and SEQ ID No. 47.

31. A method comprising:

administering to said patient an anti-Adrenomedullin (ADM) antibody or anti-ADM antibody fragment or anti-ADM non-Ig scaffold in combination with L-ascorbic acid, wherein the heavy chain of said anti-adrenomedullin (ADM) antibody or anti-ADM antibody fragment or anti-ADM non-Ig scaffold comprises:

```
                              SEQ ID No.: 1
GYTFSRYW,

SEQ ID No.: 2
ILPGSGST, and

SEQ ID No.: 3
TEGYEYDGFDY
``` and wherein the light chain of said anti-adrenomedullin (ADM) antibody or anti-ADM antibody fragment or anti-ADM non-Ig scaffold comprises:

```
                              SEQ ID No.: 4
QSIVYSNGNTY,

SEQUENCE: RVS, and
                              SEQ ID No.: 5
FQGSHIPYT;
``` wherein said patient is suffering from an acute disease or condition selected from the group consisting of: severe infections, shock, acute heart failure, myocardial infarction, stroke, and organ dysfunction, and wherein at least one of a, b, c, d, or e is satisfied:

a. stabilizing the systemic circulation of said patient who is suffering from an acute disease or acute condition, wherein said patient is in need of stabilizing the systemic circulation, wherein said patient exhibits a heart rate of >100 beats/min and/or <65 mm Hg mean arterial pressure, and wherein stabilizing the systemic circulation means increasing the mean arterial pressure over 65 mmHg, b. preventing a heart rate increase to >100 beats/min and/or a mean arterial pressure decrease to <65 mm Hg in patients having an acute disease or acute condition, c. preventing or reducing organ dysfunction or preventing organ failure in said patient suffering from a chronic and/or acute disease or acute condition, and wherein said organ is selected from the group consisting of heart, kidney, liver, lungs, pancreas, small intestines and spleen, d. achieving therapy or prevention of SIRS, meningitis, sepsis, or shock, in said patient, e. reducing mortality risk in a patient with SIRS, meningitis, sepsis, or shock;

wherein said anti-ADM antibody or anti-ADM fragment or anti-ADM non-Ig scaffold binds to the N-terminal and/or mid-regional part (amino acids 1-42) of ADM-Gly and/or ADM-NH$_2$: YRQSMNNFQGLRSFGCRFGTCTVQKLAHQIYQ FTDKDKDNVA (SEQ ID No. 23);

and optionally wherein said L-ascorbic acid is a single enantiomer, a mixture of enantiomers, a mixture of diastereomers or a pharmaceutically acceptable salt, solvate, hydrate or prodrug thereof; and wherein said patient has a ratio of pro-adrenomedullin or a fragment thereof to ADM-NH$_2$ (SEQ ID No. 20) above a predetermined threshold in a sample of bodily fluid taken from the patient prior to administration of the anti-Adrenomedullin (ADM) antibody or anti-ADM antibody fragment or anti-ADM non-Ig scaffold in combination with L-ascorbic acid.

\*　\*　\*　\*　\*